(12) United States Patent
Le et al.

(10) Patent No.: US 10,058,843 B2
(45) Date of Patent: Aug. 28, 2018

(54) MULTIFUNCTIONAL SORBENT MATERIALS AND USES THEREOF

(71) Applicants: Van So Le, Gymea (AU); Minh Khoi Le, Gymea (AU)

(72) Inventors: Van So Le, Gymea (AU); Minh Khoi Le, Gymea (AU)

(73) Assignees: Van So Le, Gymea (AU); Minh Khoi Le, Gymea (AU)

( * ) Notice: Subject to any disclaimer, the term of this patent is extended or adjusted under 35 U.S.C. 154(b) by 319 days.

(21) Appl. No.: 15/022,998

(22) PCT Filed: Sep. 19, 2014

(86) PCT No.: PCT/AU2014/000920
§ 371 (c)(1),
(2) Date: Mar. 18, 2016

(87) PCT Pub. No.: WO2015/039170
PCT Pub. Date: Mar. 26, 2015

(65) Prior Publication Data
US 2016/0228849 A1   Aug. 11, 2016

(30) Foreign Application Priority Data
Sep. 20, 2013 (AU) ................. 2013903629

(51) Int. Cl.
| | | |
|---|---|---|
| *B01J 20/22* | (2006.01) | |
| *B01D 15/38* | (2006.01) | |
| *B01J 41/08* | (2017.01) | |
| *B01J 20/28* | (2006.01) | |
| *B01J 20/32* | (2006.01) | |
| *B01J 20/34* | (2006.01) | |
| *G21F 9/12* | (2006.01) | |
| *B01J 20/30* | (2006.01) | |
| *C07F 7/21* | (2006.01) | |
| *C07F 7/28* | (2006.01) | |

(52) U.S. Cl.
CPC .......... *B01J 20/22* (2013.01); *B01D 15/3828* (2013.01); *B01J 20/28004* (2013.01); *B01J 20/28042* (2013.01); *B01J 20/28057* (2013.01); *B01J 20/28078* (2013.01); *B01J 20/28092* (2013.01); *B01J 20/3085* (2013.01); *B01J 20/3204* (2013.01); *B01J 20/3257* (2013.01); *B01J 20/3425* (2013.01); *B01J 20/3475* (2013.01); *B01J 41/08* (2013.01); *C07F 7/21* (2013.01); *C07F 7/28* (2013.01); *G21F 9/12* (2013.01)

(58) Field of Classification Search
None
See application file for complete search history.

(56) References Cited

U.S. PATENT DOCUMENTS

| | | |
|---|---|---|
| 5,681,974 A | 10/1997 | Hasegawa et al. |
| 6,326,326 B1 | 12/2001 | Feng et al. |
| 7,129,386 B2 | 10/2006 | Li |
| 7,144,930 B2 | 12/2006 | Meyer et al. |
| 7,329,386 B2 | 2/2008 | Kobayashi et al. |
| 2002/0077388 A1 | 6/2002 | Meyer et al. |
| 2009/0274634 A1 | 11/2009 | Collins et al. |
| 2011/0059845 A1 | 3/2011 | Fryxell et al. |
| 2016/0077068 A1 | 3/2016 | Schulz |

FOREIGN PATENT DOCUMENTS

| | | |
|---|---|---|
| EP | 1 997 850 A2 | 12/2008 |
| WO | WO 02/094410 | 11/2002 |
| WO | WO 2010/105938 A1 | 9/2010 |

OTHER PUBLICATIONS

International Search Report and Written Opinion for PCT/AU2014/000920, dated Nov. 24, 2014, 6 pages.

Van So Le, $^{99m}$"Tc Generator Development: Up-to-Date $^{99m}$Tc Recovery Technologies for Increasing the Effectiveness of $^{99}$Mo Utilisation", *Science and Technology of Nuclear Installations* (Hindawi Publishing Corporation), 2014, Article ID 345252, 41 pages.

Le Van So et. al., "Synthesis, characterization and application of zirconium and titanium inorganic polymer sorbents for the preparation of chromatographic $^{99m}$Tc and $^{188}$Re generators," IAEA's coordinated research project 3$^{rd}$ research coordination meeting, Oct. 8-12, 2007, Daejeon, Korea, 20 pages.

*Primary Examiner* — Clinton A Brooks
(74) *Attorney, Agent, or Firm* — Dority & Manning, P.A.

(57) ABSTRACT

The invention relates to a method for producing a sorbent material, comprising firstly providing a porous silica substrate, said substrate comprising a plurality of silanol groups on a surface thereof then reacting said silanol groups with either a silicon compound of formula $R_nSi(OR')_{4-n}$, where R is an alkyl group and n is 0 or 1, or an aminoalkyl silane of formula $R''_mR_nSi(OR')_{4-n-m}$ having at least two hydrolysable groups attached to silicon, where R" is an aminoalkyl group, m is 1 or 2 and n is 0 or 1s or a compound of formula $M(OR')_4$, or a mixture of any two or more of the preceding compounds, hydrolyzing the product, men reacting hydroxyl groups formed with one or more reagents, wherein each reagent is independently selected from the group consisting of an aminoalkyl silane having at least two hydrolysable groups attached to the silicon and a compound of formula $M(OR')_4$, and finally hydrolyzing the product, wherein each OR' independently is a hydrolysable group and each M independently is Zr, Ti, Hf, Sn, Th, Pb or Ge. There is also described a sorbent material and use of a sorbent material for purifying, separating and concentrating processes.

27 Claims, 12 Drawing Sheets

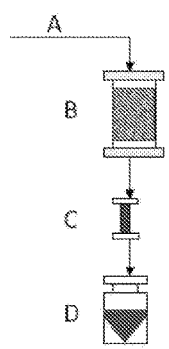
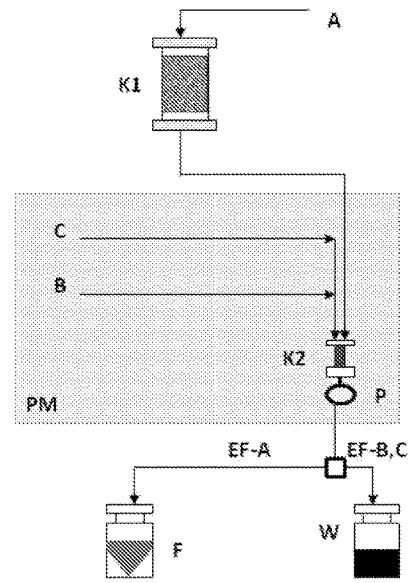
Figure 10
Figure 11
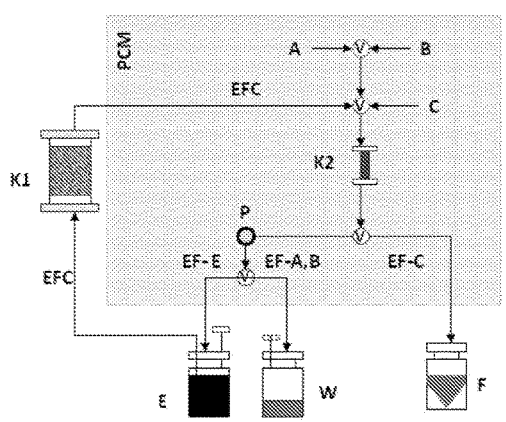
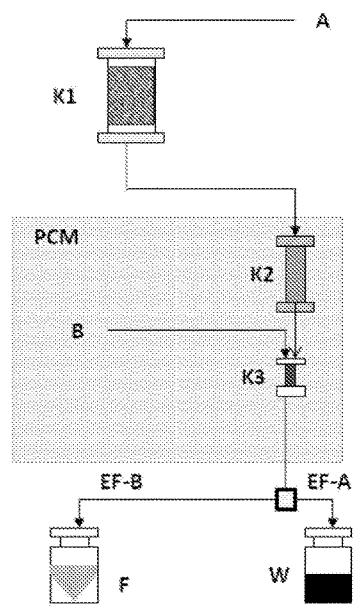
Figure 12
Figure 13

(a)          (b)

MULTIFUNCTIONAL SORBENT MATERIALS AND USES THEREOF

INCORPORATION BY CROSS REFERENCE

This present application is the national stage entry of International Patent Application No. PCT/AU2014/000920 having a filing date of Sep. 19, 2014, which claims priority from Australian provisional application no. 2013903629 having a filing date of Sep. 20, 2013, the entire contents of which are incorporated herein by cross-reference.

FIELD

The invention relates to sorbent materials and to methods for making and using them.

BACKGROUND

Sorbent Materials

Sorbent materials used in solution-based separation processes usually offer adsorptive selectivity to retain the solutes of interest. Chemical, biochemical, radiochemical and pharmaceutical separations are mainly based on the use of any one or more of the following types of sorbent:
- Ion-pair and ion-exchange sorbents that contain ionogenic/ion-exchange groups in a solid polymeric matrix;
- Normal-phase solid phase extraction (SPE) sorbents including bare silica, alumina, FLORISIL® (synthetic magnesium silicate) and silica chemically modified with polar groups such as amino, cyano or diol groups; or
- Reversed-phase SPE sorbents that contain alkyl chains bonded to a solid silica support; and/or
- Mixed-mode SPE sorbents containing alkyl chains and ion exchange groups bonded to the same solid support.

Metal oxide sorbents, including alumina, silica and ion-exchange sorbents, are particularly useful in radiochemical separations and radioisotope production and several different methods for the production of single and mixed metal oxides and hydrated oxides are known. Functionalised silica-based sorbents may also be utilised as reversed-phase, ion-exchange and mixed-mode SPE sorbents. However, many of these sorbent materials act as mono-functional sorbents, as they are based on a single active group present on the surface of the sorbent material. The application of such materials to separations is therefore limited, due to the limited adsorption selectivity and high adsorption competition of different solutes in the solution on the same active/functional group of the sorbent. This also reduces the dynamic adsorption capacity of the sorbent for the solute of interest, and as a result, adsorption competition of different solutes on the same single functional/active group of the sorbent may decrease the resolution of the separation process due to an overload of the sorbent. The solute selectivity of the monofunctional sorbents in a given separation medium is usually not tunable, which makes the separation process unmanageable.

Mixed metal oxides known in the art may exist as either (a) a homogeneous mixture of metal oxides (homogeneous distribution of molecules or of particles of functional metal oxides in the bulky mass of the sorbent) or (b) an inhomogeneous mixture of metal oxides (e.g., when the surfaces of metal oxide support particles are coated with single or mixed functional metal oxides and/or when the particles of functional metal oxide are embedded in the metal oxide matrix support). These sorbents have the disadvantage that the majority of the functional groups form a bulky inert particle mass via cross-linking $(-M-O-M-)_n$.

Other sorbent materials known in the art are synthesised by coating mono-functional organic groups on the surface of silica, which may be produced by hydrolysis of silicon alkoxides in alkali solution or by hydrolysis of sodium silicate in acidic solutions. Silica sorbents synthesised using these methods commonly have a specific surface area of 300-600 $m^2/g$, and have limited adsorption capacity due to the limited number of surface silanol groups available for covalent coupling with functional organic compounds. Efforts have been made to increase the specific surface area of such silicas and consequently to increase the number of accessible silanol groups. For example, surfactant/directing agent templated mesoporous silicas may have specific surface areas as high as 1000 $m^2/g$ or more. However, to remove the templating agent, dehydration and calcination steps are required and these additional steps can reduce the number of hydroxyl groups and increase the hydrophobic character of the silica. This may lead to difficulty in coupling functional organic compounds to the surface to produce a sorbent of high adsorption capacity. Efforts have thus also been made to remove the calcination step from such processes. However, a significant amount of surfactant residue is then found in the final silica product, reducing its utility as a sorbent material.

Radionuclide Production

Today, the technecium-99m radionuclide ($^{99m}$Tc) is used in approximately 85% of diagnostic imaging procedures in nuclear medicine worldwide. $^{99m}$Tc is produced from the radioactive decay of its parent radioisotope molybdenum-99 ($^{99}$Mo). Currently, global demand for $^{99}$Mo is primarily met through fission of uranium-235 irradiated in a nuclear reactor or through a neutron capture nuclear reaction using molybdenum-98. However, the $^{99}$Mo produced in the neutron capture method generally has a specific activity 10,000 times lower than that of fission-produced $^{99}$Mo.

Subsequent to manufacture, the $^{99}$Mo is then purified and supplied to manufacturers of $^{99}$Mo/$^{99m}$Tc generators around the world. $^{99m}$Tc is then delivered to users in the form of these $^{99}$Mo/$^{99m}$Tc generators. Rhenium-188 ($^{188}$Re) is also used in nuclear medicine procedures and therapies and is similarly derived from a tungsten-188/rhenium-188 ($^{188}$W/$^{188}$Re) generator.

A $^{99}$Mo/$^{99m}$Tc generator, colloquially known as a "technetium cow" or "moly cow", is a device used to extract the metastable isotope of technetium ($^{99m}$Tc) from the radioactive decay of $^{99}$Mo. Molybdenum-99 has a half-life ($t_{1/2}$) of approximately 66 hours. As such, it can be easily transported over long distances to radiopharmacies where its decay product, $^{99m}$Tc ($t_{1/2}$=6 hours), is extracted by normal saline elution. In such generators, $^{99}$Mo decays and produces $^{99m}$Tc, which is eluted from the generator with a saline solution and results in a saline solution containing $^{99m}$Tc as the pertechnetate ion, [$^{99m}$TcO$_4$]$^-$, with sodium as the counterbalancing cation.

However, the low $^{99}$Mo adsorption capacity and/or poor adsorption-desorption kinetics of generator packing materials (e.g., alumina, polymeric zirconium and titanium compound sorbents, sulfated alumina, aluminium-sulfated zirconia, nanocrystalline zirconia, titania and alumina and ceramic sorbents of mixed zirconium and titanium oxides) is challenging the use of low specific activity $^{99}$Mo derived from neutron capture processes, in particular because a large column is required to produce a generator of acceptable activity, which in turn requires a large volume of the eluent to elute patient-dose quantities of $^{99m}$Tc. Large eluent volumes then cause the radioactive concentration of the $^{99m}$Tc-pertechnetate to become unacceptably low for use in most radiopharmaceutical diagnostic procedures. Hence, generator packing materials used in radiochemical separations in general, and particularly in medically useful $^{99m}$Tc and $^{188}$Re radioisotope production, need further improvement. Additionally, there is a need for a further purification and/or concentration step to obtain daughter radionuclides from the generator eluates with suitable purity and concentration, e.g., for use in radiopharmaceutical diagnostic procedures.

Methods for said concentration of daughter radionuclides from radioisotope generator saline eluates have been used in clinical practice to obtain $^{99m}$Tc and $^{188}$Re from $^{99}$Mo/$^{99m}$Tc and $^{188}$W/$^{188}$Re generator systems, respectively. Such methods were initially developed for concentration of $^{188}$Re from $^{188}$W/$^{188}$Re generators. In this system, the generator normal saline eluent is first passed through a small column of cation exchange resin in Ag form, which traps the chloride anion and allows subsequent in-tandem passage through a sorbent column such as QMA (quaternary methylammonium) anion trapping cartridge to specifically trap the target perrhenate ($[ReO_4]^-$) or pertechnetate ($[TcO_4]^-$) anions. The target anions are then removed with a small volume of normal saline ready for radiolabelling use and/or injection. Sorbents currently used for this purpose are alumina, zircona, ion-exchange resins Dowex®-1x8 and AG-1x8, DEAE (diethylaminoethyl)-cellulose sorbent, Accell QMA Sep-Pak® (a silica-based anion-exchange resin with surface functionality —C(O)NH(CH$_2$)$_3$N(CH$_3$)$_3^+$Cl$^-$), and BondElut® SAX (a silica-based anion-exchange resin with surface functionality —Si(CH$_3$)$_2$—(CH$_2$)$_3$N(CH$_3$)$_3^+$Cl$^-$). All of these sorbents are monofunctional, and the $[^{99m}TcO_4]^-$ and $[^{188}ReO_4]^-$ ions must compete with contaminant ions $[^{99}MoO_4]^{2-}$, $[^{188}WO_4]^{2-}$, and Cl$^-$, which always accompany the $[^{99m}TcO_4]^-$ and $[^{188}ReO_4]^-$ ions in the solution, for adsorption sites on the sorbent material. This makes the purification/concentration process less effective. Further, the distribution coefficient ($K_d$) values of $[^{99m}TcO_4]^-$ and $[^{188}ReO_4]^-$ ions in physiological 0.9% NaCl solution is not able to be adjusted so as to facilitate the purification/concentration process.

The use of new sorbents in chemical and radiochemical purification, separation and concentration is needed to improve the performance of $^{99m}$Tc and $^{188}$Re generators and to increase the $^{99m}$Tc and/or $^{188}$Re concentration in the eluate. Hence, the present invention seeks to provide sorbent materials of high adsorption capacity for use with radioisotope generators and in radioisotope concentrator devices.

It is an object of the present invention to at least partially overcome or at least ameliorate one or more of the above outlined disadvantages of existing sorbent materials.

SUMMARY OF INVENTION

According to a first aspect of the invention, there is provided a method for producing a sorbent material, comprising:
a) providing a porous silica substrate, said substrate comprising a plurality of silanol groups on a surface thereof,
b) reacting said silanol groups with
  i) a silicon compound of formula $R_nSi(OR')_{4-n}$, where R is an alkyl group and n is 0 or 1; or
  ii) an aminoalkyl silane of formula $R''_mR_nSi(OR')_{4-n-m}$ having at least two hydrolysable groups attached to silicon, where R" is an aminoalkyl group, m is 1 or 2 and n is 0 or 1 and R is as defined above; or,
  iii) a compound of formula $M(OR')_4$; or
  iv) a mixture of any two or more of i) to iii);

c) hydrolysing the product of b) to generate hydroxyl groups;
d) reacting the hydroxyl groups generated in step c) with one or more reagents, wherein each reagent is independently selected from the group consisting of an aminoalkyl silane having at least two hydrolysable groups attached to the silicon and a compound of formula $M(OR')_4$; and
e) hydrolysing the product of d);
wherein each OR' is a hydrolysable group wherein each R' may be the same or may be different, and each M is, independently, Zr, Ti, Hf, Sn, Th, Pb or Ge. Each R' may, independently, be is an alkyl, aryl, dialkylamino or acyl group.

The following options may be used in conjunction with the first aspect either individually or in any suitable combination.

Steps d) and e) may be performed once, or may be repeated between 1 and 10 times. In one embodiment, step d) is repeated after step e), in which case step d) comprises reacting the hydroxyl groups generated in step e) with one or more reagents, wherein each reagent is independently selected from the group consisting of an aminoalkyl silane having at least two hydrolysable groups attached to the silicon and a compound of formula $M(OR')_4$. Steps d) and e) may be repeated in this way, in alternation, between 1 and 10 times. For example, where steps d) and e) are repeated once, the method according to the first aspect may comprise step a), step b), step c), step d), step e), and then step d) and step e) again.

The porous silica substrate used in step a) may have a silanol group density of between about 20 and about 150 Å$^2$/OH. It may have a mean pore size of between about 2 and about 10 nm. It may have a bimodal distribution of pore sizes. It may have a first population of pores and a second population of pores. The first population of pores may have a mean diameter of between about 2 and about 6 nm. The second population of pores may have a mean diameter of between about 6 and about 10 nm. The first population of pores may overlap with the second population of pores. In some embodiments the first population of pores does not overlap with the second population of pores. The porous silica substrate of step a) may be particulate. It may have a mean particle diameter of less than about 100 µm. It may have a specific surface area of between about 300 and about 1000 m$^2$/g.

Step c) may comprise reacting the hydrolysable groups formed in step b) with an approximately stoichiometric amount of water. Step e) may comprise reacting the hydrolysable groups formed in step d) with an approximately stoichiometric amount of water. This may involve exposing the hydrolysable groups to an approximately stoichiometric quantity of water, or to no more than an approximately stoichiometric amount of water.

The silicon compound of step b) i) may be a tetraalkoxysilane. The aminoalkyl silanes of step b) ii) or of step d) may independently be aminoalkyldialkoxyalkylsilanes or aminoalkyltrialkoxysilanes. The OR' group may be an alkoxy group.

The reactions of step b) and step d) may independently be conducted in a hydrophobic solvent. The hydrophobic solvent may be a water insoluble solvent.

Step a) may comprise
A) providing a suspension of a nanoparticulate substance in an aqueous solution of a silicate salt;
B) acidifying said aqueous solution so as to form a gel;
C) heating said gel to form a monolith;
D) forming a particulate material from said monolith; and, E) treating said particulate material with an extracting solution so as to extract the nanoparticulate substance from the particulate material.

The nanoparticulate substance of step A) may comprise a manganese dioxide sol. In this case, the extracting solution of step E) may comprise a reducing agent such as oxalic acid.

In one embodiment there is provided a method for producing a sorbent material, comprising:
a) providing a porous silica substrate having a surface silanol density of between about 20 and 150 Å$^2$/OH, and a bimodal distribution of pore sizes with a first population of pores having a mean diameter of between about 2 and about 6 nm and a second population of pores having a mean diameter of between about 6 and about 10 nm, said substrate comprising a plurality of silanol groups on a surface thereof,
b) reacting said silanol groups with
    i) a silicon compound of formula $R_nSi(OR')_{4-n}$, where R is an alkyl group and n is 0 or 1; or
    ii) an aminoalkyl silane of formula $R''_mR_nSi(OR')_{4-n-m}$ having at least two hydrolysable groups attached to silicon, where R" is an aminoalkyl group, m is 1 or 2 and n is 0 or 1; or,
    iii) a compound of formula $M(OR')_4$; or
    iv) a mixture of any two or more of i) to iii);
c) hydrolysing the product of b) to generate hydroxyl groups;
d) reacting the hydroxyl groups generated in step c) with one or more reagents, wherein each reagent is independently selected from the group consisting of an aminoalkyl silane having at least two hydrolysable groups attached to the silicon and a compound of formula $M(OR')_4$; and
e) hydrolysing the product of d);
wherein each OR' is a hydrolysable group wherein each R' is independently an alkyl, aryl, dialkylamino or acyl group, and each M is, independently, Zr, Ti, Hf, Sn, Th, Pb or Ge.

In another embodiment there is provided a method for producing a sorbent material, comprising:
a) providing a porous silica substrate, said substrate comprising a plurality of silanol groups on a surface thereof,
b) reacting said silanol groups with
    i) a silicon compound of formula $R_nSi(OR')_{4-n}$, where R is an alkyl group and n is 0 or 1; or
    ii) an aminoalkyl silane of formula $R''_mR_nSi(OR')_{4-n-m}$ having at least two hydrolysable groups attached to silicon, where R" is an aminoalkyl group, m is 1 or 2 and n is 0 or 1; or,
    iii) a compound of formula $M(OR')_4$; or
    iv) a mixture of any two or more of i) to iii);
c) hydrolysing the product of b) to generate hydroxyl groups;
d) reacting the hydroxyl groups generated in step c) with one or more reagents, wherein each reagent is independently selected from the group consisting of an aminoalkyl silane having at least two hydrolysable groups attached to the silicon and a compound of formula $M(OR')_4$; and
e) hydrolysing the product of d);
wherein each OR' is a hydrolysable group wherein each R' is independently an alkyl, aryl, dialkylamino or acyl group, and each M is, independently, Zr, Ti, Hf, Sn, Th, Pb or Ge, wherein the hydrolysing in step c) and/or step e) comprises reacting the hydrolysable groups formed in step b) and/or step d) with an approximately stoichiometric amount of water, and wherein the reactions of step b) and/or step d) are conducted in a hydrophobic solvent.

In a further embodiment there is provided a method for producing a sorbent material, comprising:
a) providing a porous silica substrate, said providing comprising
A) providing a suspension of a nanoparticulate substance in an aqueous solution of a silicate salt;
B) acidifying said aqueous solution so as to form a gel;
C) heating said gel to form a monolith;
D) forming a particulate material from said monolith; and,
E) treating said particulate material with an extracting solution so as to extract the nanoparticulate substance from the particulate material so as to produce the porous silica substrate having a plurality of silanol groups on a surface thereof;
b) reacting said silanol groups with
    i) a silicon compound of formula $R_nSi(OR')_{4-n}$, where R is an alkyl group and n is 0 or 1; or
    ii) an aminoalkyl silane of formula $R''_mR_nSi(OR')_{4-n-m}$ having at least two hydrolysable groups attached to silicon, where R" is an aminoalkyl group, m is 1 or 2 and n is 0 or 1; or,
    iii) a compound of formula $M(OR')_4$; or
    iv) a mixture of any two or more of i) to iii);
c) hydrolysing the product of b) to generate hydroxyl groups;
d) reacting the hydroxyl groups generated in step c) with one or more reagents, wherein each reagent is independently selected from the group consisting of an aminoalkyl silane having at least two hydrolysable groups attached to the silicon and a compound of formula $M(OR')_4$; and
e) hydrolysing the product of d);
wherein each OR' is a hydrolysable group wherein each R' is independently an alkyl, aryl, dialkylamino or acyl group, and each M is, independently, Zr, Ti, Hf, Sn, Th, Pb or Ge, and wherein the reactions of step b) and step d) are conducted in a hydrophobic solvent.

In yet another embodiment there is provided a method for producing a sorbent material, comprising:
a) providing a porous silica substrate, said providing comprising:
A) providing a suspension of a nanoparticulate substance in an aqueous solution of a silicate salt, wherein the nanoparticulate substance comprises a manganese dioxide sol;
B) acidifying said aqueous solution so as to form a gel;
C) heating said gel to form a monolith;
D) forming a particulate material from said monolith; and,
E) treating said particulate material with an extracting solution comprising oxalic acid so as to extract the nanoparticulate substance from the particulate material and so as to produce the porous silica substrate having a surface silanol density of between about 20 and 150 Å$^2$/OH and a bimodal distribution of pore sizes with a first population of pores having a mean diameter of between about 2 and about 6 nm and a second population of pores having a mean diameter of between about 6 and about 10 nm;
b) reacting said silanol groups with
    i) a silicon compound of formula $R_nSi(OR')_{4-n}$, where R is an alkyl group and n is 0 or 1; or
    ii) an aminoalkyl silane of formula $R''_mR_nSi(OR')_{4-n-m}$ having at least two hydrolysable groups attached to silicon, where R" is an aminoalkyl group, m is 1 or 2 and n is 0 or 1; or,
    iii) a compound of formula $M(OR')_4$; or
    iv) a mixture of any two or more of i) to iii);
c) hydrolysing the product of b) to generate hydroxyl groups, wherein said hydrolysing comprises reacting the hydrolysable groups formed in step b) with an approximately stoichiometric amount of water;

d) reacting the hydroxyl groups generated in step c) with one or more reagents, wherein each reagent is independently selected from the group consisting of an aminoalkyl silane having at least two hydrolysable groups attached to the silicon and a compound of formula M(OR')$_4$; and e) hydrolysing the product of d), wherein said hydrolysing comprises reacting the hydrolysable groups formed in step d) with an approximately stoichiometric amount of water; wherein each OR' is a hydrolysable group wherein each R' is independently an alkyl, aryl, dialkylamino or acyl group, and each M is, independently, Zr, Ti, Hf, Sn, Th, Pb or Ge, and wherein the reactions of step b) and step d) are conducted in a hydrophobic solvent, and wherein steps d) and e) are repeated between 1 and 10 times.

The present invention also provides a sorbent material produced by the method of the first aspect above.

According to a second aspect of the invention, there is provided a sorbent material comprising porous silica having a plurality of oligomeric chains on a surface thereof, said oligomeric chains having a backbone consisting of alternating oxygen and tetravalent atoms M, and wherein each of said chains comprises a plurality of M-OH moieties.

The following options may be used in conjunction with the second aspect either individually or in any suitable combination.

Each M may be independently selected from the group consisting of Si, Zr, Ti, Hf, Sn, Th, Pb, and Ge. Each M may be Si, Zr or Ti. For example, each M may be Si, or each M may be Zr, or each M may be Ti. In one embodiment, each M is independently selected from the group consisting of Si, Zr, or Ti. In another embodiment, each M is independently selected from the group consisting of Zr, Ti, Hf, Sn, Th, Pb, and Ge. In a further embodiment, each M is selected from the group consisting of Zr or Ti. At least one M per oligomeric chain may be not Si, for example, each M per oligomeric chain may be not Si. Alternatively, each M atom per oligomeric chain may be Si, or at least one M per chain may be Si.

The plurality of oligomeric chains in the sorbent material may each be identical, or the plurality of oligomeric chains in the sorbent material may be a mixture of two or more different oligomeric chains. Where each oligomeric chain is identical, every oligomeric chain in the sorbent material may comprise at least one M that is Si, or may comprise at least one M that is not Si. Alternatively, each M in every oligomeric chain may be Si, or each M in every oligomeric chain may not be Si. In a further alternative, each chain comprises at least one Si atom and at least one M atom which is not Si. Where the plurality of oligomeric chains in the sorbent material is a mixture of two or more different oligomeric chains, at least one M in at least one oligomeric chain in the sorbent material may be Si, or at least one M in at least one oligomeric chain in the sorbent material may not be Si. Alternatively, each M in at least one oligomeric chain may be Si, or each M in at least one oligomeric chain may not be Si. In a further alternative, there is at least one chain which comprises a Si atom and at least one chain which comprises an M atom which is not Si.

Each oligomeric chain may be branched or may be unbranched. One or more of the oligomeric chains may comprise at least one aminoalkyl group bonded to an Si atom. For example, in one embodiment, each oligomeric chain in the sorbent material comprises at least one aminoalkyl group bonded to an Si atom. In another embodiment, at least one oligomeric chain in the sorbent material comprises at least one aminoalkyl group bonded to an Si atom. The aminoalkyl group may be selected from the group consisting of —$C_3H_6NH_2$, —$C_3H_6NHC_2H_4NH_2$, —$C_3H_6N(CH_3)_2$, —$C_3H_6N(C_2H_5)_2$, —$C_3H_6NH(CH_3)$, and —$C_3H_6NH(C_2H_5)$, or may be selected from the group consisting of —$C_2H_4N(C_2H_5)_2$ and —$CH_2N(C_2H_5)_2$, or may be selected from the group consisting of —$C_3H_6NH_2$, —$C_3H_6NHC_2H_4NH_2$, —$C_3H_6N(CH_3)_2$, —$C_3H_6N(C_2H_5)_2$, —$C_3H_6NH(CH_3)$, —$C_3H_6NH(C_2H_5)$, —$C_2H_4N(C_2H_5)_2$ and —$CH_2N(C_2H_5)_2$. Each oligomeric chain may have only a single point of attachment to the surface of the porous silica. Each oligomeric chain may have one or two points of attachment to the surface of the porous silica. Each chain may have one point of attachment, or each chain may have two points of attachment, or some chains may have one point of attachment and others may have two points of attachment. In some embodiments, no chains have more than two points of attachment. Each oligomeric chain may have a backbone having a maximum length of 18 M-O units. There may be no oligomeric chains having more than 18 M-O units in its backbone. In this context, the backbone is considered to be the longest chain of alternating M and O atoms in a chain which is attached to the substrate.

The sorbent material may have a mean pore size of between about 2 and about 10 nm. It may have a bimodal distribution of pore sizes. It may have a first population of pores having a mean diameter of about 2 to about 6 nm and a second population of pores having a mean diameter of about 6 to about 10 nm. It may be particulate. It may have a mean particle diameter of less than about 100 μm. The sorbent material may have a specific surface area of between about 300 and about 1000 m$^2$/g. It may have an adsorption capacity of molybdenum of more than about 450 mg Mo/g sorbent material. It may have an adsorption capacity of tungsten of more than about 850 mg W/g sorbent material.

In one embodiment there is provided a sorbent material comprising porous silica having a plurality of oligomeric chains on a surface thereof, wherein the sorbent material has a bimodal distribution of pore sizes comprising a first population of pores and a second population of pores, the first population of pores having a mean diameter of about 2 to about 6 nm and the second population of pores having a mean diameter of about 6 to about 10 nm, wherein the sorbent material is particulate with a mean particle diameter of less than about 100 μm, and a specific surface area of between about 300 and about 1000 m$^2$/g, said oligomeric chains having a backbone consisting of alternating oxygen and tetravalent atoms M, and wherein each of said chains comprises a plurality of M-OH moieties.

In another embodiment there is provided a sorbent material comprising porous silica having a plurality of oligomeric chains on a surface thereof, wherein the sorbent material is particulate, having a mean particle diameter of less than about 100 μm, and a specific surface area of between about 300 and about 1000 m$^2$/g, said oligomeric chains having a backbone consisting of alternating oxygen and tetravalent atoms M having a maximum length of 18 M-O units, wherein each M is independently Si, Zr, Ti, Hf, Sn, Th, Pb, or Ge, wherein each of said oligomeric chains comprises a plurality of M-OH moieties, and wherein each oligomeric chain has one or two points of attachment to the surface of the porous silica.

In yet another embodiment there is provided a sorbent material comprising porous silica having a plurality of oligomeric chains on a surface thereof, wherein the sorbent material is particulate, having a mean particle diameter of less than about 100 μm, and a specific surface area of between about 300 and about 1000 m$^2$/g, said oligomeric chains having a backbone consisting of alternating oxygen and tetravalent atoms M and a maximum length of 18 M-O units, wherein each M is independently Si, Zr, Ti, Hf, Sn, Th, Pb, or Ge, wherein each of said chains comprises a plurality of M-OH moieties, wherein each oligomeric chain has one or two points of attachment to the surface of the porous silica and wherein one or more of the oligomeric chains comprise at least one aminoalkyl group bonded to an Si atom.

In another embodiment there is provided a sorbent material comprising porous silica having a plurality of oligomeric chains on a surface thereof, wherein the sorbent material is particulate, having a mean particle diameter of less than about 100 μm, and a specific surface area of between about 300 and about 1000 $m^2/g$, said oligomeric chains having a backbone consisting of alternating oxygen and tetravalent atoms M having a maximum length of 18 M-O units, wherein each M is independently Si, Zr, Ti, Hf, Sn, Th, Pb, or Ge, wherein each of said chains comprises a plurality of M-OH moieties, wherein each oligomeric chain has one or two points of attachment to the surface of the porous silica, and wherein the oligomeric chains are devoid of aminoalkyl groups.

In a further embodiment there is provided a sorbent material comprising porous silica having a plurality of oligomeric chains on a surface thereof, wherein the sorbent material has a mean particle diameter of less than about 100 μm, said oligomeric chains having a backbone consisting of alternating oxygen and tetravalent atoms M having a maximum length of 18 M-O units, wherein each M is independently Si, Zr, or Ti, wherein each of said chains comprises a plurality of M-OH moieties, wherein each oligomeric chain comprises at least one aminoalkyl group bonded to an Si atom, and wherein each oligomeric chain has one or two points of attachment to the surface of the porous silica.

In yet a further embodiment there is provided a sorbent material comprising porous silica having a plurality of oligomeric chains on a surface thereof, wherein the sorbent material has a mean particle diameter of less than about 100 μm, said oligomeric chains having a backbone consisting of alternating oxygen and tetravalent Si atoms having a maximum length of 18 Si—O units, wherein each of said chains comprises a plurality of Si—OH moieties, wherein each oligomeric chain comprises at least one aminoalkyl group bonded to an Si atom, and wherein each oligomeric chain has one or two points of attachment to the surface of the porous silica.

The sorbent material of the second aspect may be made by the method of the first aspect. The method of the first aspect may make the sorbent material of the second aspect.

According to a third aspect of the invention, there is provided a method for purifying and/or concentrating one or more target species in a solution comprising a mixture of metal ions, said method comprising:
a) providing a solution comprising one or more contaminant species and the one or more target species;
b) contacting the solution of step a) with a sorbent material comprising porous silica having a plurality of oligomeric chains on a surface thereof, said oligomeric chains having a backbone consisting of alternating oxygen and tetravalent M atoms, wherein each of said chains comprises a plurality of M-OH moieties, and wherein each M is independently selected from the group consisting of Si, Zr, Ti, Hf, Sn, Th, Pb, and Ge; and,
c) separating the solution from the sorbent material as an eluate following step b).

The following options may be used in conjunction with the third aspect either individually or in any suitable combination.

The contaminant species may be of formula $[Z^1O_4]^{2-}$. The target species may be of formula $[Z^2O_4]^-$. $Z^1$ may be Mo or W. $Z^2$ may be Tc or Re. $Z^2$ or $Z^1$ may be radioactive, or both $Z^2$ and $Z^1$ may be radioactive. The contaminant species may be a $D^{4+}$ ion, or the contaminant species may comprise a $D^{4+}$ or D(IV) ion, wherein D is selected from the group consisting of Ti, Ge, Zr, Sn and Hf. The target species may be an $X^{3+}$ ion, or the target species may comprise an $X^{3+}$ or X(III) ion, wherein X is selected from the group consisting of Sc, Ga, Y, In or Lu. D or X may be radioactive, or both D and X may be radioactive.

The sorbent material may be according to the second aspect above, or may be made by the first aspect above. The sorbent material may be particulate. The contacting of step b) may comprise passing the solution of step a) through the sorbent material. It may comprise passing the solution through a column comprising the sorbent material as a column packing material. The chains of the sorbent material may comprise at least one M that is not Si. The contacting of step b) may cause the contaminant species to bind to the sorbent material by forming at least one M-O—$Z^1$ or M-O-D linkage, wherein M is Zr, Ti, Hf, Sn, Th, Pb, or Ge.

The eluate in step c) may comprise purified target species. The method may further comprise step d) regenerating the sorbent material; wherein said regenerating comprises adding a regenerating solution to the sorbent material. Step d) may comprise passing the regenerating solution through the sorbent material. It may comprise dispersing the sorbent in the regenerating solution and then separating said solution from the sorbent. The regenerating solution may release $Z^1$ or D species present on the sorbent material into the regenerating solution. The regenerating solution may be a basic solution. It may have a pH of greater than about 12. It may comprise hydroxide ions. For example, it may be a hydroxide solution. It may comprise a solution of sodium hydroxide, potassium hydroxide, or ammonium hydroxide, or a mixture of any two or more of these. The total hydroxide concentration of the regenerating solution may be between about 0.01 and about 1.0 M. The sorbent material after step d) may comprise less than about 0.01% (w/w) $Z^1$ or D.

The sorbent material of step b) may comprise oligomeric chains having at least one aminoalkyl group bonded to an M centre, wherein each M in the oligomeric chain is Si. The contacting of step b) may cause the one or more target species to bind to the sorbent material, whereby the eluate in step c) comprises the one or more contaminant species. The method may further comprise collecting the eluate in a receptacle. It may further comprise contacting an eluting solution with the sorbent material following step c), said eluting solution being capable of reversing the binding of the target species to the sorbent, whereby the target species passes into the eluting solution. The volume of eluting solution may be lower than the volume of the solution of step a). The eluting solution may comprise a saline solution. It may comprise sodium sulfate and/or ammonium sulfate. The eluting solution may be a basic solution. For example, it may have a pH of greater than about 12. The eluting solution may comprise hydroxide ions. For example, it may be a hydroxide solution. It may comprise sodium hydroxide, potassium hydroxide, and/or ammonium hydroxide. The eluting solution may have a total salt concentration of between about 0.01 and about 1.0 M. The eluting solution containing the target species may be collected in a receptacle separate to the eluate containing the contaminant species.

The oligomeric chains of the sorbent material may alternatively comprise at least one M that is not Si. Where the oligomeric chains comprise at least one M that is not Si, one or more of the oligomeric chains may further comprise at least one aminoalkyl group bonded to an Si atom. The contacting of step b) may cause the target species and the contaminant species to bind to the sorbent material. The method may further comprise collecting the eluate of step c) in a receptacle. In this alternative, the method may further comprise step d') contacting an eluting solution with the sorbent material of step b), wherein said eluting solution may be capable of reversing the binding of the target species to the sorbent, whereby the target species may pass into the eluting solution. The volume of eluting solution in step d') may be lower than the volume of the solution of step a). The eluting solution may comprise a saline solution. It may comprise sodium sulfate and/or ammonium sulfate. It may have a total salt concentration of between about 0.1 and about 8 M. Step d') may further comprise collecting the eluting solution containing the target species in a receptacle. The method may further comprise step e) regenerating the sorbent material, wherein said regenerating comprises adding a regenerating solution to the sorbent material. Step e) may comprise passing the regenerating solution through the sorbent material. The regenerating solution may release contaminant $Z^1$ or D species present on the sorbent material into the regenerating solution. The regenerating solution may be a basic solution. For example, it may have a pH of greater than about 12. It may comprise hydroxide ions. For example, it may comprise a dissolved Group I or Group II hydroxide salt or may comprise dissolved ammonium hydroxide. For example, the regenerating solution may comprise lithium hydroxide, sodium hydroxide, potassium hydroxide, magnesium hydroxide, or calcium hydroxide, or a mixture of any two or more of these, e.g., the regenerating solution may comprise a solution of sodium hydroxide, potassium hydroxide, or ammonium hydroxide, or a mixture of any two or more of these. The total hydroxide concentration may be between about 0.01 and about 1.0 M. The sorbent material after step e) may comprise less than about 0.01% (w/w) $Z^1$ or D. The regenerating solution may be collected in a receptacle separate to the eluate of step c) and the eluting solution of step d) during or after the regenerating of step e).

The method may additionally comprise the following steps A) to C) prior to step a):
A) providing a solution comprising one or more target species and one or more contaminant species;
B) contacting the solution of step A) with a sorbent material comprising porous silica having a plurality of oligomeric chains on a surface thereof, said oligomeric chains having a backbone consisting of alternating oxygen and tetravalent M atoms, and wherein each of said oligomeric chains comprises a plurality of M-OH moieties;
wherein the oligomeric chains of the sorbent material comprise at least one M that is not Si; and, wherein the affinity of the sorbent material for the target species is lower than that for the contaminant species;
C) extracting the sorbent material from step B) with an extracting solution so as to produce an extract, said extracting solution being capable of extracting the target species from the sorbent material and said extract being the solution of step a).

The target species of step A) may be an $X^{3+}$ ion, or may comprise an $X^{3+}$ ion, wherein X is selected from the group consisting of Sc, Ga, Y, In or Lu. The contaminant species of step A) may be a $D^{4+}$ ion, or may comprise a $D^{4+}$ ion, wherein D is selected from the group consisting of Ti, Ge, Zr, Sn and Hf. The solution of step A) may comprise a parent species that decays over time to form the target species, whereby the parent species is the contaminant species. The parent species may be of formula $[Z^1O_4]^{2-}$ and the target species may be of formula $[Z^2O_4]^-$, wherein when $Z^1$=Mo, $Z^2$=Tc, or when $Z^1$=W, $Z^2$=Re. The extracting solution may comprise a saline solution. The extracting solution may comprise recycled eluate produced by the step c) of the method. The method may concentrate the target species.

In one embodiment, the sorbent material in step b) is produced by the method according to the first aspect of the invention above or is according to the second aspect of the invention above.

In an embodiment there is provided a method for purifying and/or concentrating a solution comprising a mixture of metal ions, said method comprising:
a) providing a solution comprising one or more contaminant species and one or more target species, wherein the target species is of formula $[Z^2O_4]^-$ or $X^{3+}$ and the contaminant species is of formula $[Z^1O_4]^{2-}$ or $D^{4+}$, wherein $Z^1$ is Mo or W and X is Sc, Ga, Y, In or Lu, and $Z^2$ is Tc or Re and D is Ti, Ge, Zr, Sn or Hf;
b) contacting the solution of step a) with a sorbent material comprising porous silica having a plurality of oligomeric chains on a surface thereof, wherein the sorbent material is particulate, said oligomeric chains having a backbone consisting of alternating oxygen and tetravalent M atoms, wherein each of said chains comprises a plurality of M-OH moieties, and wherein each M is independently selected from the group consisting of Si, Zr, Ti, Hf, Sn, Th, Pb, and Ge; and,
c) separating the solution from the sorbent material as an eluate following step b).

In another embodiment there is provided a method for purifying and/or concentrating a solution comprising a mixture of metal ions, said method comprising:
a) providing a solution comprising one or more contaminant species and one or more target species, wherein the target species is of formula $[Z^2O_4]^-$ or $X^{3+}$ and the contaminant species is of formula $[Z^1O_4]^{2-}$ or $D^{4+}$, wherein $Z^1$ is Mo or W and X is Sc, Ga, Y, In or Lu, and $Z^2$ is Tc or Re and D is Ti, Ge, Zr, Sn or Hf;
b) contacting the solution of step a) with a sorbent material comprising porous silica having a plurality of oligomeric chains on a surface thereof, said oligomeric chains having a backbone consisting of alternating oxygen and tetravalent M atoms, wherein each of said chains comprises a plurality of M-OH moieties, wherein each M is independently selected from the group consisting of Si, Zr, Ti, Hf, Sn, Th, Pb, and Ge, wherein the sorbent material is devoid of aminoalkyl groups and wherein the contacting causes the contaminant species to bind to the sorbent material by forming at least one M-O—$Z^1$ or M-O-D linkage;
c) separating the solution from the sorbent material as an eluate following step b); and,
d) regenerating the sorbent material, wherein said regenerating comprises adding a regenerating solution to the sorbent material, wherein the regenerating solution releases $Z^1$ or $D^{4+}$ species present on the sorbent material into the regenerating solution and wherein the regenerating solution comprises a solution of sodium hydroxide, potassium hydroxide, or ammonium hydroxide, or a mixture of any two or more of these, and has a total hydroxide ion concentration of between about 0.01 and about 1.0 M.

In yet another embodiment there is provided a method for purifying and/or concentrating a solution comprising a mixture of metal ions, said method comprising: a) providing a solution comprising one or more contaminant species and one or more target species, wherein the target species is of formula $[Z^2O_4]^-$ or $X^{3+}$ and the contaminant species is of formula $[Z^1O_4]^{2-}$ or $D^{4+}$, wherein $Z^1$ is Mo or W and X is Sc, Ga, Y, In or Lu, and $Z^2$ is Tc or Re and D is Ti, Ge, Zr, Sn or Hf;

b) contacting the solution of step a) with a sorbent material comprising porous silica having a plurality of oligomeric chains on a surface thereof, said oligomeric chains having a backbone consisting of alternating oxygen and tetravalent M atoms, wherein each of said chains comprises a plurality of M-OH moieties, and wherein each M is independently selected from the group consisting of Si, Zr, Ti, Hf, Sn, Th, Pb, and Ge, wherein at least one M is Si and the oligomeric chains comprise at least one aminoalkyl group bonded to an Si atom, and wherein the contacting causes the target species to bind reversibly to the sorbent material and the contaminant species to bind to the sorbent material by forming at least one M-O—$Z^1$ or M-O-D linkage;

c) separating the solution from the sorbent material as an eluate following step b);

d') contacting an eluting solution with the sorbent material of step b), wherein said eluting solution is capable of reversing the binding of the target species to the sorbent, whereby the target species passes into the eluting solution and wherein the eluting solution comprises a saline solution comprising sodium sulfate and/or ammonium sulfate; and, e) regenerating the sorbent material, wherein said regenerating comprises adding a regenerating solution to the sorbent material, wherein the regenerating solution releases $Z^1$ or $D^{4+}$ species present on the sorbent material into the regenerating solution and wherein the regenerating solution comprises a solution of sodium hydroxide, potassium hydroxide, or ammonium hydroxide, or a mixture of any two or more of these.

In a further embodiment there is provided a method for purifying and/or concentrating a solution comprising a mixture of metal ions, said method comprising:

a) providing a solution comprising one or more contaminant species and one or more target species, wherein the target species is of formula $Z^2O_4^-$ or $X^{3+}$ and the contaminant species is of formula $Z^1O_4^{2-}$ or $D^{4+}$, wherein $Z^1$ is Mo or W and X is Sc, Ga, Y, In or Lu, and $Z^2$ is Tc or Re and D is Ti, Ge, Zr, Sn or Hf;

b) contacting the solution of step a) with a sorbent material comprising porous silica having a plurality of oligomeric chains on a surface thereof, said oligomeric chains having a backbone consisting of alternating oxygen and tetravalent M atoms, wherein each of said chains comprises a plurality of M-OH moieties, and wherein each M is Si and the oligomeric chains comprise at least one aminoalkyl group bonded to an Si atom, and wherein the contacting causes the target species to bind reversibly to the sorbent material; and, c) separating the solution from the sorbent material as an eluate following step b), wherein the eluate comprises the one or more contaminant species, wherein step c) further comprises contacting an eluting solution with the sorbent material following step c), said eluting solution being capable of reversing the binding of the target species to the sorbent, whereby the target species passes into the eluting solution, and wherein the eluting solution comprises a saline solution comprising sodium sulfate, ammonium sulfate, sodium hydroxide, potassium hydroxide, or ammonium hydroxide or any combination of two or more of these.

In a further embodiment there is provided a method for purifying and/or concentrating a solution comprising a mixture of metal ions, said method comprising:

A) providing a solution comprising one or more target species and one or more contaminant species;

B) contacting the solution of step A) with a sorbent material comprising porous silica having a plurality of oligomeric chains on a surface thereof, said oligomeric chains having a backbone consisting of alternating oxygen and tetravalent M atoms, and wherein each of said chains comprises a plurality of M-OH moieties;

wherein the oligomeric chains of the sorbent material comprise at least one M that is not Si; and, wherein the affinity of the sorbent material for the target species is lower than that for the contaminant species;

C) extracting the sorbent material from step B) with an extracting solution so as to produce an extract, said extracting solution being capable of extracting the target species from the sorbent material;

a) providing the extract of step C) comprising one or more contaminant species and one or more target species, wherein the target species is of formula $[Z^2O_4]^{2-}$ or $X^{3+}$ and the contaminant species is of formula $[Z^1O_4]^{2-}$ or $D^{4+}$, wherein $Z^1$ is Mo or W and X is Sc, Ga, Y, In or Lu, and $Z^2$ is Tc or Re and D is Ti, Ge, Zr, Sn or Hf;

b) contacting the solution of step a) with a sorbent material comprising porous silica having a plurality of oligomeric chains on a surface thereof, wherein the sorbent material is particulate, said oligomeric chains having a backbone consisting of alternating oxygen and tetravalent M atoms, wherein each of said chains comprises a plurality of M-OH moieties, and wherein each M is independently selected from the group consisting of Si, Zr, Ti, Hf, Sn, Th, Pb, and Ge; and, c) separating the solution from the sorbent material as an eluate following step b).

According to a fourth aspect of the invention, there is provided use of a sorbent according to the second aspect for concentrating a target species from a solution comprising one or more contaminant species and the target species.

In one embodiment there is provided use of a sorbent according to the second aspect for concentrating a target species of formula $[Z^2O_4]^-$ from a solution comprising one or more contaminant species and the target species of formula $[Z^1O_4]^{2-}$ wherein $Z^1$=Mo or W and $Z^2$=Tc or Re.

In another embodiment there is provided use of a sorbent according to the second aspect for concentrating an $X^{3+}$ ion target species, wherein X is selected from the group consisting of Sc, Ga, Y, In or Lu, from a solution comprising one or more $D^{4+}$ ion contaminant species, wherein D is selected from the group consisting of Ti, Ge, Zr, Sn and Hf, and the target species.

According to a fifth aspect of the invention, there is provided use of a sorbent according to the second aspect for separating a target species from a contaminant species from a solution comprising one or more contaminant species and one or more target species.

In one embodiment there is provided use of a sorbent according to the second aspect for separating a target species from a contaminant species from a solution comprising one or more contaminant species and one or more target species where the contaminant species is a parent species that decays over time to form the target species. The decay may be radioactive decay.

In another embodiment there is provided use of a sorbent according to the second aspect for separating a target species of formula $[Z^2O_4]^-$ from a contaminant species of formula $[Z^1O_4]^{2-}$ from a solution comprising one or more contaminant species and one or more target species and wherein $Z^1$=Mo or W and $Z^2$=Tc or Re.

In yet another embodiment there is provided use of a sorbent according to the second aspect for separating an $X^{3+}$ ion target species, wherein X is selected from the group consisting of Sc, Ga, Y, In or Lu, from a $D^{4+}$ ion contaminant species, wherein D is selected from the group consisting of Ti, Ge, Zr, Sn and Hf, from a solution comprising one or more contaminant species and one or more target species.

According to a sixth aspect of the invention, there is provided use of a sorbent material according to the second aspect in a radioisotope concentrator device.

BRIEF DESCRIPTION OF DRAWINGS

FIG. 10 is a diagram showing a possible "catch-without-release" process for the use of sorbent materials of the invention in a $^{99m}Tc/^{99}Mo$ and/or $^{188}Re/^{188}W$ generator. Key: A: Normal saline eluent; B: $^{99m}Tc$- or $^{188}Re$-generator column using functionalised silica sorbent; C: Purification column (containing functionalised silica sorbent according to the present invention); D: Purified $^{99m}Tc$- or $^{188}Re$ solution.

FIG. 11 is a diagram showing a possible "catch-without-release" process for $^{99m}Tc$ and $^{188}Re$ purification, showing both (i) the use of the sorbent materials of the invention in the $^{99m}Tc$ and $^{188}Re$ purification module; and, (ii) use of a $^{99m}Tc/^{99}Mo$ and/or $^{188}Re/^{188}W$ generator coupled with the $^{99m}Tc$ and $^{188}Re$ purification module.
Key: A: Normal saline eluent; K1: $^{99m}Tc$- or $^{188}Re$-generator column; C: Water; B: 0.5 M NaOH solution; K2: Purification column (containing functionalised silica sorbent according to the present invention or recoverable sorbent); P: Pump; EF-A: Eluent Flow from A; EF-B,C: Eluent Flow from B and C; W: Low activity liquid waste; F: Purified $^{99m}Tc$- or $^{188}Re$ solution; PM: Purification Module.

FIG. 12 is a diagram showing a possible "catch and release (I)" process for $^{99m}Tc$ and $^{188}Re$ purification/concentration, showing the use of the sorbent materials of the invention in a $^{99m}Tc$ and $^{188}Re$ purification/concentration module and in the $^{99m}Tc/^{99}Mo$ and/or $^{188}Re/^{188}W$ generator coupled with $^{99m}Tc$ and $^{188}Re$ purification/concentration module.
Key: A: NaOH solution; B: Water; C: Saline; K1: $^{99m}Tc$- or $^{188}Re$-generator column using functionalised silica sorbent; K2: Purification-Concentration Column (containing functionalised silica sorbent according to the present invention or recoverable sorbent); P: Pump; EF-E: Eluent flow from E; EF-A,B: Eluent Flow from A,B; EF-C: Eluent Flow from C; EFC: Eluent Flow circulation; E: Non-saline aqueous eluent (e.g., acetic acid/acetate/<0.05% NaCl solution mixture or <0.05% NaCl solution); W: Waste from water and NaOH wash; F: Purified, Concentrated $^{99m}Tc$- or $^{188}Re$ solution.

FIG. 13 is a diagram showing an alternative possible "catch and release (II)" process for $^{99m}Tc$ and $^{188}Re$ purification/concentration, showing the use of sorbent materials of the invention in a $^{99m}Tc$ and $^{188}Re$ purification/concentration module and in the $^{99m}Tc/^{99}Mo$ and/or $^{188}Re/^{188}W$ generator coupled with a $^{99m}Tc$ and $^{188}Re$ purification/concentration module.
Key: A: Normal saline eluent; B: Sterile saline eluent; K1: $^{99m}Tc$- or $^{188}Re$-generator column; K2: Salt/Chloride removing column; K3: Purification-Concentration Column (containing functionalised silica sorbent according to the present invention); EF-B: Eluent Flow from B; EF-A: Eluent Flow from A; W: Low activity liquid waste; F: Concentrated $^{99m}Tc$- or $^{188}Re$ solution; PCM: Purification/Concentration Module.

DEFINITIONS

Figure 1:
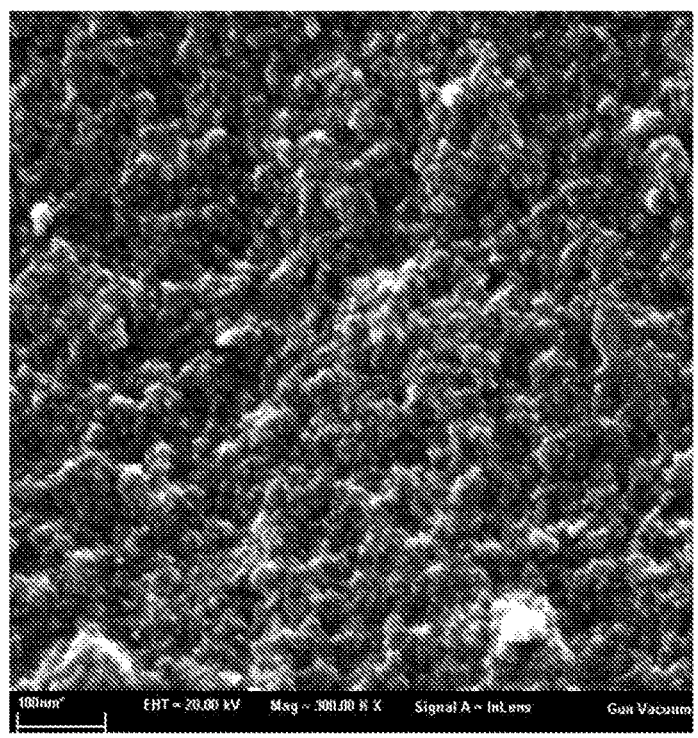
FIG. 1 shows an electron microscope image (SEM) of silica synthesised using the $MnO_2$-template method.

As used in this application, the singular form "a", "an" and "the" include plural references unless the context clearly dictates otherwise. For example, the phrase "a target species" also includes a plurality of target species.

As used herein, the term "comprising" means "including." Variations of the word "comprising", such as "comprise" and "comprises," have correspondingly varied meanings. As used herein, the terms "including" and "comprising" are non-exclusive. Thus, for example, a solution "comprising" solvent and one or more contaminant species and one or more target species may consist exclusively of the solvent, the contaminant species and the target species, or it may contain other components, for example, buffer ions, salts, solvents, etc. As used herein, the term "comprising" does not imply that the specified integer(s) represent a major part of the whole.

As used herein the term "plurality" means more than one. In certain specific aspects or embodiments, a plurality may mean 2, 3, 4, 5, 6, 7, 8, 9, 10, 15, 20, 30, 40, 50, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$, or more, and any integer derivable therein, and any range derivable therein.

It will be understood that use the term "about" herein in reference to a recited numerical value includes the recited numerical value and numerical values within plus or minus ten percent of the recited value unless the context indicates otherwise. The term "about 0" may refer a range of between exactly 0 and 0.01.

It will be understood that use of the term "between" herein when referring to a range of numerical values encompasses the numerical values at each endpoint of the range. For example, a surface area per silanol group of between about 20 and about 150 Å$^2$/OH is inclusive of a surface area per silanol group of about 20 Å$^2$/OH and a surface area per silanol group of about 150 Å$^2$/OH.

As used herein, the term "eluate" may refer to a solution obtained by elution, i.e., "eluate" may refer to any solution comprising one or more chemical species that has been extracted from a sorbent material by means of a solvent or eluting solution or eluent, regardless of the method by which the eluate is separated from the sorbent material. The eluate may be obtained by passing an eluent through a bed or column of sorbent material either under gravity or through use of vacuum or pressure. It will be understood that the eluate may also be obtained by any suitable means of contacting an eluent with the sorbent material, e.g., through stirring or agitating a mixture of an eluent and sorbent material and collecting the eluate as a supernatant after centrifugation or as a filtrate after filtration.

DETAILED DESCRIPTION

The present invention relates to new sorbent materials with improved selectivity and functionality. These sorbent materials combine the advantages of large surface area silica, which may be generated using a new process of nanoparticle-templated gel formation, with the multi-functionality of layers of functional groups (including in certain embodiments tetravalent metal oxides and/or silanol groups and/or aminoalkyl silanes). This results in multifunctional sorbent materials that are able to selectively adsorb solutes via chemisorption and adsorb ionic species of interest via pH-controlled ion-exchange and/or coordinative adsorption.

The following detailed description conveys exemplary embodiments of the present invention in sufficient detail to enable those of ordinary skill in the art to practice the present invention. Features or limitations of the various embodiments described do not necessarily limit other embodiments of the present invention or the present invention as a whole. Hence, the following detailed description does not limit the scope of the present invention, which is defined only by the claims.

Sorbent Material Production

The present invention relates to a method for producing a sorbent material, comprising:
a) providing a porous silica substrate, said substrate comprising a plurality of silanol groups on a surface thereof,
b) reacting said silanol groups with
   i) a silicon compound of formula $R_nSi(OR')_{4-n}$, where R is an alkyl group and n is 0 or 1; or
   ii) an aminoalkyl silane of formula $R''_mR_nSi(OR')_{4-n-m}$ having at least two hydrolysable groups attached to silicon, where R'' is an aminoalkyl group, m is 1 or 2 and n is 0 or 1; or,
   iii) a compound of formula $M(OR')_4$, or
   iv) a mixture of any two or more of i) to iii);
c) hydrolysing the product of b) to generate hydroxyl groups;
d) reacting the hydroxyl groups generated in step c) with one or more reagents, wherein each reagent is independently selected from the group consisting of an aminoalkyl silane having at least two hydrolysable groups attached to the silicon and a compound of formula $M(OR')_4$; and
e) hydrolysing the product of d);
wherein each OR' is a hydrolysable group wherein each R' may be the same or may be different, and each M is, independently, Zr, Ti, Hf, Sn, Th, Pb or Ge.

In one embodiment, the present invention relates to a method for producing a sorbent material, comprising:
a) providing a porous silica substrate, said substrate comprising a plurality of silanol groups on a surface thereof,
b) reacting said silanol groups with one or more compounds of formula $M(L^1L^2L^3L^4)$, wherein each M is, independently, Si, Zr, Ti, Hf, Sn, Th, Pb or Ge, and wherein
$L^1$ is OR';
$L^2$ is independently either OR' or R;
and L and $L^4$ are each independently either OR' or R'';

where R is an alkyl group, each OR' is a hydrolysable group wherein each R' may be the same or may be different, and R'' is an aminoalkyl group;
c) hydrolysing the product of b) to generate hydroxyl groups;
d) reacting the hydroxyl groups generated in step c) with one or more reagents of formula $M(L^1L^2L^3L^4)$, wherein either $L^1=L^2=L^3=L^4=OR'$ and M is not Si, or at least one of $L^3$ and $L^4$ is R'' and M is Si; and,
e) hydrolysing the product of d).

In this embodiment, it will be understood that M, $L^1$ to $L^4$, R' and R'' in step b) may each be the same as or different to those used in step d) provided that they are within the same defined scope.

Silica Substrate

The porous silica substrate of step a) comprises a plurality of silanol groups on a surface thereof. The porous silica substrate of step a) may have a surface area per silanol group of between about 20 and about 150 $Å^2$/OH, or between about 30 and 140, 30 and 120, 30 and 110, 30 and 100, 35 and 95, 40 and 80, 40 and 100, 30 and 80, 35 and 70, 20 and 70, 20 and 60, 40 and 60, 40 and 50, 20 and 50, 40 and 90, 40 and 55, or 40 and 45 $Å^2$/OH, e.g., about 20, 25, 30, 35, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145 or 150 $Å^2$/OH. The density of silanol groups on the surface of the silica sorbent may be adjusted such that the number of condensation reactions occurring in steps b) to e) is at a desired level. It may also be adjusted so that steric interactions and spatial overlap that would then occur between compounds bound to the silanol groups on the surface of the silica are at a suitably low level. The silanol density may be controlled or modified using any suitable method or technique. For example, the density may be controlled or modified during synthesis of the porous silica substrate by altering one or more of the pH of the gelation solution, the concentration of the silicate solution, the gelation time, and/or the drying temperature of the xerogel.

The porous silica substrate used in step a) may have a mean pore size of between about 2 and about 10 nm, or between about 2 and 5, 2 and 8, 3 and 10, 3 and 8, 4 and 8, 4 and 10, 5 and 6, 5 and 8, 5 and 10, 6 and 10, 6 and 8, 7 and 10, 8 and 10, 9 and 10, 3 and 6, 2 and 6, 2 and 3, or 2 and 4 nm, e.g., 2, 2.5, 3, 3.5, 4, 4.5, 5, 5.5, 6, 6.5, 7, 7.5, 8, 8.5, 9, 9.5 or 10 nm. Pore size may be determined by those skilled in the art using, for example, nitrogen or hydrogen adsorption/desorption methods.

The porous silica substrate used in step a) may have a bimodal distribution of pore sizes comprising a first population of pores and a second population of pores. The first population of pores may have a mean diameter of about 4 nm, or about 2 to about 6 nm, or about 2 to 4, 4 to 6, or 3 to 5 nm, or about 2, 3, 4, 5, 6 nm. The second population of pores may have a mean diameter of about 8 nm, or about 6 to about 10 nm, or about 6 to 8, 8 to 10 or 7 to 9 nm, or about 6, 7, 8, 9, 10 nm. The mean diameter of the pores in the porous silica may be determined using any suitable technique known in the art, for example, by measuring a gas (e.g., nitrogen) adsorption and/or desorption isotherm and/or by utilising light scattering techniques such as x-ray diffraction. The porous silica substrate of step a) may be particulate. The porous silica substrate particles may be spherical, substantially spherical, acicular, flat, flaky, prismoidal, polyhedral, fibrous, irregular, spheroidal, or granular, or may be some other shape, or may be a combination of these shapes. Where the particles are not spherical, the diameter of a particle may be taken as the hydrodynamic diameter, or may be take to be the minimum dimension of a particle (e.g., a thickness) or the maximum dimension of a particle (e.g., a length) or the mean dimension of a particle.

The porous silica substrate particles may have a mean particle diameter of less than about 100 μm, or less than about 95, 90, 85, 80, 75, 70, 65, 60, 55, 50, 45, 40, 35, 30, 25, 20 or 15 μm, or between about 10 and about 100 μm, 10 and 50, 50 and 100, or 20 and 70 μm, e.g., about 95, 90, 85, 80, 75, 70, 65, 60, 55, 50, 45, 40, 35, 30, 25, 20, 15 or 10 μm. The particle size of the porous silica substrate may be measured using any suitable technique known in the art, e.g., dynamic light scattering, sieving, laser diffraction, microscopy, LALLS etc.

The porous silica substrate of step a) may have a specific surface area of between about 300 and about 1000 m$^2$/g, or between about 300 and about 700, 500 and 1000, 700 and 900, 300 and 500, 325 and 475, 500 and 625 m$^2$/g, or about 300, 325, 350, 375, 400, 425, 450, 475, 500, 525, 550, 575, 600, 625, 650, 675, 700, 725, 750, 775, 800, 825, 850, 875, 900, 925, 950, 975 or 1000 m$^2$/g. The porous silica substrate of step a) may have a void volume of between about 0.5 mL/g to about 1.5 mL/g, or between about 0.5 and about 1.0, 0.9 and 1.3, or 1.0 and 1.5 mL/g, or about 0.8, 0.9, 1.0, 1.1, 1.2, 1.3, 1.4 or 1.5 mL/g. The specific surface area and/or void volume of the porous silica may be determined using any suitable technique known in the art, for example, by experimentally collecting a gas (e.g., nitrogen) adsorption isotherm and by subsequent calculation using, e.g., the Brunauer-Emmett-Teller (BET) equation.

Silicon Compounds

In step b) i), the silicon compound of formula $R_nSi(OR')_{4-n}$ may be an alkoxysilane (n=0) or may be an alkylalkoxysilane (n=1). The alkyl group R may be methyl, ethyl, propyl, butyl, pentyl, hexyl, heptyl, octyl, nonyl or decyl. It may be straight chain or may be branched. It may be $C_1$ to $C_{12}$ alkyl, or $C_1$ to $C_6$ alkyl, or $C_1$ to $C_3$ alkyl.

The hydrolysable group OR' may be any group capable of being hydrolysed. For example, the hydrolysable group —OR' may be any group that reacts with water to form an —OH group, producing, as a by-product, an R'OH molecule. The hydrolysable group OR' may be an alkoxy group. R' may be as described above for R. In the formula $R_nSi(OR')_{4-n}$, n may be 0 or n may be 1. In step b) i), the silicon compound of formula $R_nSi(OR')_{4-n}$ may be a tetralkoxysilane, e.g., tetraethylorthosilicate (tetraethoxysilane), tetramethylorthosilicate (tetramethoxysilane) or tetrapropylorthosilicate (tetrapropoxysilane), or some other tetralkoxysilane. In step b) i), the silicon compound of formula $R_nSi(OR')_{4-n}$ may be an alkylalkoxysilane, e.g., methyltriethoxysilane, methyltrimethoxysilane, ethyltrimethoxysilane, or ethyltriethoxysilane, or some other alkylalkoxysilane. OR' may be an alkyl or aryl carbonyloxy group, e.g., an acetoxy group. OR' may be an oximo group, e.g., an aldoximo or a ketoximo, e.g., methylethylketoximo. OR' may be an aryloxy group, e.g., phenoxy. Each OR' in the silicon compound of formula $R_nSi(OR')_{4-n}$ may be the same or may be different.

The reaction between the silanol groups of the porous silica substrate in step a) and a compound according to step b) i) may be represented by Equation 1:

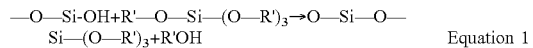

Equation 1

According to Equation 1, the product of step b) is —O—Si—O—Si—(O—R')$_3$.

Aminoalkyl Silane Compounds

In step b) ii), the aminoalkyl silane of formula $R''_mR_nSi(OR')_{4-n-m}$ having at least two hydrolysable groups attached to silicon may be, for example, an (aminoalkyl)alkyldialkoxyalkylsilane. The alkyl group in the (aminoalkyl)alkyldialkoxyalkylsilane may be as described above for R. In step b) ii), the aminoalkyl silane of formula $R''_mR_nSi(OR')_{4-n-m}$ having at least two hydrolysable groups attached to silicon may be an aminoalkyltrialkoxysilane. In the formula $R''_mR_nSi(OR')_{4-n-m}$, n may be 0 or n may be 1. In the formula $R''_mR_nSi(OR')_{4-n-m}$, m may be 1 or m may be 2. The aminoalkyl silane may therefore be of formula $R''Si(OR')_3$, $R''_2Si(OR')_2$, or $R''RSi(OR')_2$. The aminoalkyl silane of formula $R''_2RSi(OR')$ (i.e., where m is 2 and n is 1) does not have at least two hydrolysable groups attached to the silicon. The hydrolysable groups attached to silicon may be alkoxy groups. The hydrolysable groups may be as described above for OR'. The aminoalkyl group R'' may be an amino-substituted alkyl group, e.g., aminomethyl, aminoethyl, aminopropyl, aminobutyl, aminopentyl, aminohexyl, aminoheptyl, aminooctyl, aminononyl or aminodecyl. The aminoalkyl group may linear or branched. The aminoalkyl group may comprise a primary, secondary or tertiary amine. The alkyl chain of the aminoalkyl group may comprise less than 15 carbon atoms, or may be less than 15 carbon atoms in length, e.g., may have less than 15, or less than 13, 10, 8, 6, 4, or 2 carbon atoms, e.g., may have between 15 and 1 carbon atoms, or between 15 and 8, 10 and 5, or 8 and 1 carbon atoms, e.g., may have 15, 14, 13, 12, 11, 10, 9, 8, 7, 6, 5, 4, 3, 2 or 1 carbon atoms, or may be less than 15 carbon atoms in length, or less than 13, 10, 8, 6, 4, or 2 carbon atoms, e.g., may be between 15 and 1 carbon atoms in length, or between 15 and 8, 10 and 5, or 8 and 1 carbon atoms, e.g., may be 15, 14, 13, 12, 11, 10, 9, 8, 7, 6, 5, 4, 3, 2 or 1 carbon atoms in length. One or more of the amino-substituted alkyl groups bonded to the silicon may also comprise, as a substituent, one or more N-(aminoalkyl) groups. Each N-(aminoalkyl) group may independently be an amino-substituted alkyl group, e.g., N-aminomethyl, N-aminoethyl, N-aminopropyl, N-aminobutyl, N-aminopentyl, N-aminohexyl, N-aminoheptyl, N-aminooctyl, N-aminononyl or N-aminodecyl. Each N-aminoalkyl group may independently be linear or branched. Each N-aminoalkyl group may individually comprise a primary, secondary or tertiary amine. In step b) ii), the aminoalkyl silane of formula $R'''_mR_nSi(OR')_{4-n-m}$ having at least two hydrolysable groups attached to silicon may be, for example, (3-aminopropyl)methyldimethoxysilane (($CH_3O)_2CH_3SiC_3H_6NH_2$), (3-aminopropyl)methyldiethoxysilane (($CH_3CH_2O)_2CH_3SiC_3H_6NH_2$), 3-aminopropyltrimethoxysilane (($CH_3O)_3SiC_3H_6NH_2$), 3-aminopropyltriethoxysilane (($CH_3CH_2O)_3SiC_3H_6NH_2$), [N(β-aminoethyl)γ-aminopropyl]methyldimethoxysilane (($CH_3O)_2CH_3SiC_3H_6NHC_2H_4NH_2$), [N(β-aminoethyl)γ-aminopropyl]methyldiethoxysilane (($CH_3CH_2O)_2CH_3SiC_3H_6NHC_2H_4NH_2$), N(β-aminoethyl)γ-aminopropyltrimethoxysilane (($CH_3O)_3SiC_3H_6NHC_2H_4NH_2$), N(β-aminoethyl)γ-aminopropyltriethoxysilane (($CH_3CH_2O)_3SiC_3H_6NHC_2H_4NH_2$), (3-diethylaminopropyl)methyldimethoxysilane (($CH_3O)_2CH_3SiC_3H_6N(C_2H_5)_2$), (3-diethylaminopropyl)methyldiethoxysilane (($CH_3CH_2O)_2CH_3SiC_3H_6N(C_2H_5)_2$), 3-diethylaminopropyltrimethoxysilane (($CH_3O)_3SiC_3H_6N(C_2H_5)_2$), 3-diethylaminopropyltriethoxysilane (($CH_3CH_2O)_3SiC_3H_6N(C_2H_5)_2$), 3-dimethylaminopropyltriethoxysilane (($CH_3CH_2O)_3SiC_3H_6N(CH_3)_2$), (3-diethylaminomethyl)methyldimethoxysilane (($CH_3O)_2CH_3SiCH_2N(C_2H_5)_2$), (3-diethylaminomethyl)

methyldiethoxysilane (($CH_3CH_2O)_2CH_3SiCH_2N(C_2H_5)_2$), 3-diethylaminomethyltrimethoxysilane (($CH_3O)_3SiCH_2N(C_2H_5)_2$), 3-diethylaminomethyltriethoxysilane (($CH_3CH_2O)_3SiCH_2N(C_2H_5)_2$), (3-diethylaminoethyl)methyldimethoxysilane (($CH_3O)_2CH_3SiC_2H_4N(C_2H_5)_2$), (3-diethylaminoethyl)methyldiethoxysilane (($CH_3CH_2O)_2CH_3SiC_2H_4N(C_2H_5)_2$), 3-diethylaminoethyltrimethoxysilane (($CH_3O)_3SiC_2H_4N(C_2H_5)_2$), or 3-diethylaminoethyltriethoxysilane (($CH_3CH_2O)_3SiC_2H_4N(C_2H_5)_2$).

The reaction between the silanol groups of the porous silica substrate in step a) and a compound according to step b) ii) may be represented by Equation 2:

$$—O—Si-OH + (R'—O)_3Si—R'' \rightarrow —O—Si—O—(R'—O)_2Si—R'' + R'OH \quad \text{Equation 2}$$

According to Equation 2, the product of step b) is —O—Si—O—(R'—O)$_2$Si—R''.

Compounds of Formula M(OR')$_4$

In step b) iii), the compound of formula M(OR')$_4$ may be Zr(OR')$_4$ or Ti(OR')$_4$, wherein the hydrolysable group OR' may be as described above. The compound of formula M(OR')$_4$ may be Hf(OR')$_4$, Sn(OR')$_4$, Th(OR')$_4$, Pb(OR')$_4$ or Ge(OR')$_4$, wherein the hydrolysable group OR' may be as described above. In step b) iii), the compound of formula M(OR')$_4$ may be, for example, Ti(OCH$_2$CH$_3$)$_4$, Ti(OCH$_3$)$_4$, Ti(OCH$_2$CH$_2$CH$_3$)$_4$, Ti(OCH(CH$_3$))$_4$, Zr(OCH$_2$CH$_3$)$_4$, Zr(OCH$_3$)$_4$, Zr(OCH$_2$CH$_2$CH$_3$)$_4$, Zr(OCH(CH$_3$)$_2$)$_4$, Hf(OCH$_2$CH$_3$)$_4$, Hf(OCH$_3$)$_4$, Hf(OCH$_2$CH$_2$CH$_3$)$_4$, Hf(OCH(CH$_3$)$_2$)$_4$, Sn(OCH$_2$CH$_3$)$_4$, Sn(OCH$_3$)$_4$, Sn(OCH$_2$CH$_2$CH$_3$)$_4$, Sn(OCH(CH$_3$)$_2$)$_4$, Th(OCH$_2$CH$_3$)$_4$, Th(OCH$_3$)$_4$, Th(OCH$_2$CH$_2$CH$_3$)$_4$, Th(OCH(CH$_3$)$_2$)$_4$, Pb(OCH$_2$CH$_3$)$_4$, Pb(OCH$_3$)$_4$, Pb(OCH$_2$CH$_2$CH$_3$)$_4$, Pb(OCH(CH$_3$)$_2$)$_4$, Ge(OCH$_2$CH$_3$)$_4$, Ge(OCH$_3$)$_4$, Ge(OCH$_2$CH$_2$CH$_3$)$_4$, or Ge(OCH(CH$_3$)$_2$)$_4$.

The reaction between the silanol groups of the porous silica substrate in step a) and a compound according to step b) iii) may be represented by Equation 3:

$$—O—Si-OH + R'—O-M-(O—R')_3 \rightarrow —O—Si—O-M-(O—R')_3 + R'OH \quad \text{Equation 3}$$

According to Equation 3, the product of step b) is —O—Si—O-M-(O—R').

Reaction Conditions

In step b) iv), the mixture of any two or more of i) to iii) may comprise a compound of formula R$_n$Si(OR')$_{4-n}$, where R is an alkyl group and n is 0 or 1 and an aminoalkyl silane of formula R''$_m$R$_n$Si(OR')$_{4-n-m}$, having at least two hydrolysable groups attached to silicon, where m is 1 or 2 and n is 0 or 1. In step b) iv), the mixture of any two or more of i) to iii) may comprise a compound of formula R$_n$Si(OR')$_{4-n}$, where R is an alkyl group and n is 0 or 1 and a compound of formula M(OR')$_4$. In step b) iv), the mixture of any two or more of i) to iii) may comprise an aminoalkyl silane of formula R''$_m$R$_n$Si(OR')$_{4-n-m}$ having at least two hydrolysable groups attached to silicon, where m is 1 or 2 and n is 0 or 1, and a compound of formula M(OR')$_4$. In step b) iv), the mixture of any two or more of i) to iii) may comprise a compound of formula R$_n$Si(OR')$_{4-n}$, where R is an alkyl group and n is 0 or 1, an aminoalkyl silane of formula R''$_m$R$_n$Si(OR')$_{4-n-m}$ having at least two hydrolysable groups attached to silicon, where m is 1 or 2 and n is 0 or 1, and a compound of formula M(OR')$_4$.

Step b) may be conducted in a hydrophobic solvent. The hydrophobic solvent may be toluene, benzene, chloroform, diethyl ether, hexane, cyclohexane, pentane or cyclopentane, or a mixture of any two or more of these. The hydrophobic solvent may be water insoluble. In this context, "insoluble" may refer to having solubility in water at 25° C. of less than 15 000 mg/L, or less than 10 000, 5 000, 1 000, 500, 100, 50, 20, 10, 5, 2, or 1 mg/L, or between about 15 000 and 5 mg/L, or 15 000 and 5 000, 10 000 and 1 000, 5 000 and 10, 10 000 and 100, 100 and 10, 50 and 5, 10 and 1, or 5 and 1 mg/L, e.g., 15 000, 10 000, 5 000, 1 000, 500, 100, 50, 20, 10, 5, 2, or 1 mg/L. The hydrophobic solvent may be one that separates from water when mixed therewith. It will be recognised that there may be some degree of dissolution of the hydrophobic solvent in water and of water in the hydrophobic solvent.

Step c) may comprise reacting the hydrolysable groups formed in step b) with a stoichiometric amount of water. Step c) may comprise reacting the hydrolysable groups formed in step b) with substantially no excess of water present. The stoichiometric amount of water may be determined using following equations (Equations 4 to 6), and the choice of equation may depend on whether step b) comprises reacting the silanol groups of step a) with either i) a silicon compound of formula R$_n$Si(OR')$_{4-n}$, where R is an alkyl group and n is 0 or 1 (Equation 4), ii) an aminoalkyl silane of formula R''$_m$R$_n$Si(OR')$_{4-n-m}$ having at least two hydrolysable groups attached to silicon, where m is 1 or 2 and n is 0 or 1 (Equation 5), or iii) a compound of formula M(OR')$_4$ (Equation 6):

$$—O—Si—O—Si—(OR')_3 + 3H_2O \rightarrow —O—Si—O—Si—(OH)_3 + 3R'OH \quad \text{Equation 4}$$

$$—O—Si—O—(R'O)_2Si—R'' + 2H_2O \rightarrow —O—Si—O—(HO)_2Si—R'' + 2R'OH \quad \text{Equation 5}$$

$$—O—Si—O-M-(OR')_3 + 3H_2O \rightarrow —O—Si—O-M-(OH)_3 + 3R'OH \quad \text{Equation 6}$$

The stoichiometric amount of water may be an approximately 1:1 molar ratio of hydrolysable OR' groups to water. The molar ratio of hydrolysable OR' groups to water may be between about 0.5:1 and 1.5:1, 0.75:1 and 1.25:1, 0.75:1 and 1.5:1, 0.75:1 and 1:1, 0.8:1 and 1.2:1, 0.9:1 and 1.1:1, or may be about 0.5:1, 0.6:1, 0.70:1, 0.75:1, 0.80:1, 0.85:1, 0.90:1, 0.95:1, 1.00:1, 1.05:1, 1.10:1, 1.15:1, 1.20:1, 1.25:1, 1.30:1:1.4:1, or 1.5:1. Accordingly, the term 'approximately stoichiometric amount of water' may refer to a molar ratio of hydrolysable OR' groups to water of between about 0.5:1 and about 1.5:1, or between about 0.75:1 and 1.25:1, 0.75:1 and 1.5:1, 0.75:1 and 1:1, 0.8:1 and 1.2:1, 0.9:1 and 1.1:1, or about 0.5:1, 0.6:1, 0.70:1, 0.75:1, 0.80:1, 0.85:1, 0.90:1, 0.95:1, 1.00:1, 1.05:1, 1.10:1, 1.15:1, 1.20:1, 1.25:1, 1.30:1:1.4:1, or 1.5:1. An advantage of adding an approximately stoichiometric amount of water in step c) is that the conversion of hydrolysable groups to —OH groups on compounds bound to the silica surface is thought to be higher than if significantly non-stoichiometric amounts are used. A further advantage of adding a stoichiometric amount of water in step c) is that in subsequent step d), condensation reactions between the aminoalkyl silane and/or the compound of formula M(OR')$_4$ and —OH groups directly or indirectly bound to the silica surface are increased compared to when significantly non-stoichiometric amounts are used. Excess water added in step c) that does not react with hydrolysable groups on the surface of the silica would be free to undergo a condensation reaction with the compounds of step d), but as these compounds may not be covalently bound to the surface of the silica, such reactions would not result in functionalisation of the surface of the silica sorbent.

In step d), hydroxyl groups formed in step c) may be reacted with one or more reagents, wherein each reagent is independently selected from the group consisting of an aminoalkyl silane of formula R'''$_m$R$_n$Si(OR')$_{4-n}$ having at least two hydrolysable groups attached to the silicon, where m is 1 or 2 and n is 0 or 1, and a compound of formula M(OR')$_4$. In step d), the aminoalkyl silane of formula R'''$_m$R$_n$Si(OR')$_{4-n-m}$ having at least two hydrolysable groups attached to silicon may be an (aminoalkyl)alkyldialkoxyalkylsilane. The alkyl group may be as described above for R. In step b) ii), the aminoalkyl silane of formula R'''$_m$R$_n$Si(OR')$_{4-n-m}$ having at least two hydrolysable groups attached to silicon may be an aminoalkyltrialkoxysilane. In the formula R'''$_m$R$_n$Si(OR')$_{4-n-m}$, n may be 0 or n may be 1. In the formula R'''$_m$R$_n$Si(OR')$_{4-n-m}$, m may be 1 or m may be 2. The aminoalkyl silane may therefore be of formula R"Si(OR')$_3$, R"$_2$Si(OR')$_2$ or R"RSi(OR')$_2$. The hydrolysable groups attached to silicon may be alkoxy groups. The hydrolysable groups may be OR' as described above. The aminoalkyl group R" may be a linear or branched amino-substituted alkyl group comprising a primary, secondary or tertiary amine as described above. One or more of the amino-substituted alkyl groups bonded to the silicon may also comprise, as a substituent, one or more N-(aminoalkyl) groups as described above. In step d), the compound of formula M(OR')$_4$ may be Zr(OR')$_4$ or Ti(OR')$_4$, wherein the hydrolysable group OR' may be as described above. The compound of formula M(OR')$_4$ may be Hf(OR')$_4$, Sn(OR')$_4$, Th(OR')$_4$, Pb(OR')$_4$ or Ge(OR')$_4$, wherein the hydrolysable group OR' may be as described above. In step b) iii), the compound of formula M(OR')$_4$ may be, for example, Ti(OCH$_2$CH$_3$)$_4$, Ti(OCH$_3$)$_4$, Ti(OCH$_2$CH$_2$CH$_3$)$_4$, Ti(OCH(CH$_3$)$_2$)$_4$, Zr(OCH$_2$CH$_3$)$_4$, Zr(OCH$_3$)$_4$, Zr(OCH$_2$CH$_2$CH$_3$)$_4$, Zr(OCH(CH$_3$)$_2$)$_4$, Hf(OCH$_2$CH$_3$)$_4$, Hf(OCH$_3$)$_4$, Hf(OCH$_2$CH$_2$CH$_3$)$_4$, Hf(OCH(CH$_3$)$_2$)$_4$, Sn(OCH$_2$CH$_3$)$_4$, Sn(OCH$_3$)$_4$, Sn(OCH$_2$CH$_2$CH$_3$)$_4$, Sn(OCH(CH$_3$)$_2$)$_4$, Th(OCH$_2$CH$_3$)$_4$, Th(OCH$_3$)$_4$, Th(OCH$_2$CH$_2$CH$_3$)$_4$, Th(OCH(CH$_3$)$_2$)$_4$, Pb(OCH$_2$CH$_3$)$_4$, Pb(OCH$_3$)$_4$, Pb(OCH$_2$CH$_2$CH$_3$)$_4$, Pb(OCH(CH$_3$)$_2$)$_4$, Ge(OCH$_2$CH$_3$)$_4$, Ge(OCH$_3$)$_4$, Ge(OCH$_2$CH$_2$CH$_3$)$_4$, or Ge(OCH(CH$_3$)$_2$)$_4$. In step d), the hydroxyl groups formed in step c) may be reacted with a mixture of at least one aminoalkyl silane of formula R'''$_m$R$_n$Si(OR')$_{4-n-m}$ having at least two hydrolysable groups attached to the silicon, where m is 1 or 2 and n is 0 or 1, and at least one compound of formula M(OR')$_4$.

Step d) may be conducted in a hydrophobic solvent. The hydrophobic solvent may be as described above with respect to step b).

Step e) may comprise reacting the hydrolysable groups formed in step d) with a stoichiometric amount of water. The stoichiometric amount of water may be determined using following equations (Equations 7 and 8), and the choice of equation may depend on whether step d) comprises reacting the silanol groups of step c) with either an aminoalkyl silane of formula R'''$_m$R$_n$Si(OR')$_{4-n-m}$ having at least two hydrolysable groups attached to silicon, where m is 1 or 2 and n is 0 or 1 (Equation 7), or a compound of formula M(OR')$_4$ (Equation 8):

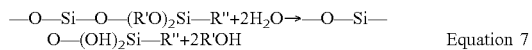

—O—Si—O—(R'O)$_2$Si—R"+2H$_2$O→—O—Si—O—(OH)$_2$Si—R"+2R'OH      Equation 7

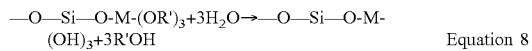

—O—Si—O-M-(OR')$_3$+3H$_2$O→—O—Si—O-M-(OH)$_3$+3R'OH      Equation 8

The stoichiometric amount of water may be a 1:1 molar ratio of hydrolysable OR' groups to water. The molar ratio of hydrolysable OR' groups to water may be between about 0.5:1 and 1.5:1, 0.75:1 and 1.25:1, 0.75:1 and 1.5:1, 0.75:1 and 1:1, 0.8:1 and 1.2:1, 0.9:1 and 1.1:1, or may be 0.5:1, 0.6:1, 0.70:1, 0.75:1, 0.80:1, 0.85:1, 0.90:1, 0.95:1, 1.00:1, 1.05:1, 1.10:1, 1.15:1, 1.20:1, 1.25:1, 1.30:1:1.4:1, or 1.5:1. The advantages of adding a stoichiometric amount of water in step e) are as described above for step c).

Steps d) and e) may be performed once or may be repeated. Steps d) and e) may be repeated at least 2 times, or between 2 and 10 times, 2 and 5 times, 3 and 10 times, or at least 2, 3, 4, 5, 6, 7 or 8 times. Where step d) and step e) are repeated, step d) may comprise reacting the hydroxyl groups generated in step e) with one or more reagents, each independently selected from the group consisting of an aminoalkyl silane having at least two hydrolysable groups attached to the silicon and a compound of formula M(OR')$_4$.

Preparation of Silica Substrate

The porous silica substrate of step a) may be made by
A) providing a suspension of a nanoparticulate substance in an aqueous solution of a silicate salt;
B) acidifying said aqueous solution so as to form a gel;
C) heating said gel to form a monolith;
D) forming a particulate material from said monolith; and,
E) treating said particulate material with an extracting solution so as to extract the nanoparticulate substance from the particulate material.

In step A), the nanoparticulate substance may form a sol. The sol may then be used as a template around which the gel of step B) forms, causing the resultant gel to contain soluble inclusions. In step C), the gel may solidify to form a porous matrix or monolith, which contains approximately evenly distributed inclusions. These inclusions may then be dissolved by an extracting solution in step E) to leave approximately evenly distributed voids in the porous matrix, the voids containing the inclusions having a defined size and the pores connecting the inclusion voids having a different defined size. This may lead to a bimodal distribution of pore sizes or voids in the resultant porous silica particulate material or powder.

In step A), the nanoparticulate substance may comprise a transition metal oxide, such as manganese dioxide, or a lanthanoid oxide, e.g., lanthanum oxide. In step A), the nanoparticulate substance may comprise a metal carbonate, for example a transition metal carbonate, e.g., calcium carbonate, strontium carbonate or barium carbonate. The nanoparticulate substance may comprise a transition metal oxide or a metal carbonate, however any other dissolvable/removable material of suitable particle size may be used. The managanese dioxide may be formed in-situ by the reduction of a permanganate salt. The permanganate salt may be a group I salt, e.g., sodium permanganate or potassium permanganate. The reduction of the permanganate salt may be conducted in aqueous solution. The aqueous solution may comprise a reducing agent, for example, a water soluble alcohol, e.g., methanol, ethanol or propanol. The nanoparticulate substance of step A) may comprise a transition metal oxide sol. The transition metal oxide sol may therefore be a manganese dioxide sol. The silicate salt in step A) may be a group I silicate salt, e.g., sodium silicate or potassium silicate. The silicate salt may be any other water soluble silicate salt. The silicate salt may be a metasilicate salt.

In step B), "acidifying" may be taken to mean effecting a reduction in pH of the solution relative to the pH of the solution in step A). In step B), acidification of the aqueous solution may comprise adding an acid and/or a pH buffer to the solution. The acid may be a mineral acid, e.g., HCl, H$_2$CO$_3$, H$_2$SO$_4$, HNO$_3$, or H$_3$PO$_4$. The acid may be an organic acid, e.g., acetic acid or citric acid. The pH of the acidified aqueous solution resulting from step B) may be less than pH 10, 9.5, 9, 8.5, 8, 8.5, 7, 6.5, 6, 5.5, 5, 4.5, 4, 3.5 or pH 3, or between about pH 10 and 3, 10 and 7, 7 and 3, 6 and 3, 5 and 4, or 8 and 6, e.g., pH 7, 6.5, 6, 5.5, 5, 4.5, 4, 3.5 or pH3.

Step C), comprising heating the gel formed in step B) to form a monolith, may comprise heating the gel formed in step B) to a temperature of between about 70 and 110° C., or between about 75 and 110, 80 and 110, 80 and 100, 90 and 110, or 90 and 100° C. The heating of the gel in step C) may be performed using a sealed vessel under autogenous pressure. The monolith formed in step C) may be subsequently dried at about 60° C., or between about 40 and 70° C., or about 40, 45, 50, 55, 60, 65, or 70° C. The porous monolith obtained in step C) may be used in step E) as is (i.e., without forming a particulate material therefrom, as described in step D). Alternatively, the porous monolith obtained in step C) may be subjected to step D) so as to form a particulate material. Thus, in step D), the forming of the particulate material may comprise grinding the monolith into particles, or it may comprise abrading the monolith, or it may comprise crushing the monolith, or it may comprise some other process for forming the particulate material from the monolith. In step D), the resulting particulate material may have a mean particle diameter of less than about 100 µm, or less than 95, 90, 85, 80, 75, 70, 65, 60, 55, 50, 45, 40, 35, 30, 25, 20 or 15 µm, e.g., about 100, 95, 90, 85, 80, 75, 70, 65, 60, 55, 50, 45, 40, 35, 30, 25, 20 or 15 µm. Step D) may additionally or alternatively comprise sieving or milling or other methods known to those of skill in the art to control the particle size and/or to remove particles of a size outside (above and/or below) a desired range. The particulate material may comprise a powder. The particulate material obtained in step E) may also be subsequently dried. It may be dried at a temperature below the temperature at which Si—OH groups are condensed to form Si—O—Si linkages, e.g., at a temperature of about 145 to 140° C., or at a temperature of less than about 145° C., or less than about 140, 135, 130, 125, 120, 110, 100° C., or between about 140 and 100° C., 100 and 80, or 130 and 80° C., e.g., at about 145, 140, 135, 130, 125, 120, 110 or 100° C. The temperature at which Si—OH groups are condensed to form Si—O—Si linkages may be determined by methods known to one skilled in the art, for example, by thermogravimetric analysis. The drying may be facilitated by application of a vacuum or partial vacuum to the particulate material.

Step E) may extract the nanoparticulate substance from the powder. The nanoparticulate substance may be extracted by dissolving the nanoparticulate substance and/or decomposing the nanoparticulate substance and/or reacting with the nanoparticulate substance to form a soluble species. The nanoparticulate substance may be a transition metal oxide. The extracting solution may comprise a reducing agent. The reducing agent may reduce the transition metal oxide to form small soluble transition metal ions. The reducing agent may reduce manganese oxide to form small soluble manganese metal ions. The reducing agent may be oxalic acid. The oxalic acid may reduce $Mn^{4+}$ in $MnO_2 \cdot xH_2O$ to $Mn^{2+}$ ions.

Sorbent Material

A sorbent material according to the present invention may comprise porous silica having a plurality of oligomeric chains on a surface thereof said oligomeric chains having a backbone consisting of alternating oxygen and tetravalent atoms M, and wherein each of said chains comprises a plurality of M-OH moieties.

The plurality of oligomeric chains on the surface of the porous silica may be on the inner pore surface or the outer particle surface of the silica, or on both the inner pore and outer particle surfaces of the silica. The oligomeric chains may each have a single point of attachment to the surface of the porous silica, or may each have at least one point of attachment to the surface. The point of attachment may be a single O-M bond, where the O is bonded to one or more silicon atoms on the surface of the porous silica substrate and M is Si, Zr, Ti, Hf, Sn, Th, Pb or Ge. A 'plurality' of oligomeric chains on the surface of the porous silica may refer to a multiplicity of oligomeric chains on the surface, e.g., an oligomeric chain may be attached to every available silanol (Si—OH) group on the surface of the silica, or on substantially every available silanol group on the surface, or on e.g., every second, third, fourth, fifth or sixth available silanol group. A 'plurality' of M-OH moieties may refer to each oligomeric chain comprising a multiplicity of M-OH moieties, e.g., two or more M-OH moieties per oligomeric chain, or at least one M-OH moiety per M atom in each oligomeric chain. A 'plurality' of M-OH moieties may refer to more than one M-OH moiety per M atom in each oligomeric chain.

The backbone of the oligomeric chains may comprise alternating oxygen and tetravalent M atoms, e.g., •••M-O-M-O-M-O•••. The backbone of the oligomeric chains may be taken as the longest continuous network of •••M-O-M-O-M-O••• linkages. The oligomeric chains on the surface of the porous silica, or the backbones thereof, may be linear or may be branched. The oligomeric chain backbones may comprise a maximum of 18 M-O units, e.g., they may comprise less than 18, 15, 10, or 5 M-O units, e.g., between about 18 and 10 M-O units, 12 and 5 M-O units, or 7 and 3 M-O units, e.g., 18, 17, 16, 15, 14, 13, 12, 11, 10, 9, 8, 7, 6, 5, 4, or 3 M-O units. Where the oligomeric chains are branched, the oligomeric chain backbone may comprise no more than 18 M-O units in total. The oligomeric chain backbone may alternatively have a total length of no more than 18 M-O units, e.g., a length of less than 18, 15, 10, or 5 M-O units, e.g., between about 18 and 10 M-O units, 12 and 5 M-O units, or 7 and 3 M-O units, e.g., 18, 17, 16, 15, 14, 13, 12, 11, 10, 9, 8, 7, 6, 5, 4, or 3 M-O units. Where the point of attachment of each oligomeric chain is a single O-M bond and the O is bonded to one or more silicon atoms on the surface of the porous silica substrate, this first O may be excluded when counting the maximum of 18 M-O units in the backbone of the oligomeric chain as described above.

Each tetravalent M atom may form 4 single bonds. Each tetravalent M atom may have tetrahedral geometry. Each tetravalent M atom may, independently, be Si, Zr, Ti, Hf, Sn, Th, Pb, or Ge, e.g., each M atom may, independently, be Si, Zr or Ti. Each oligomeric chain may comprise M atoms where every M atom is Si, Zr, Ti, Hf, Sn, Th, Pb, or Ge. At least one M per oligomeric chain may be Zr, Ti, Hf, Sn, Th, Pb, or Ge, e.g., at least one M per oligomeric chain may not be Si. At least one M per oligomeric chain may be Zr or Ti. It will be understood by persons skilled in the art that the term 'tetravalent M atom' may refer to a tetravalent M ion, or may refer to an M atom having been tetravalent (e.g., an $M^{4+}$ ion) prior to formation of four single covalent bonds, or may refer to the formal oxidation state of an M atom in its starting compound, e.g., Si in $R_nSi(OR')_{4-n}$, where R is an alkyl group and n is 0 or 1, Si in $R''_mR_nSi(OR')_{4-n-m}$, where R" is an aminoalkyl group, m is 1 or 2 and n is 0 or 1, or M in $M(OR')_4$, where each OR' is a hydrolysable group, or may refer to the formal oxidation state of an M atom in the oligomeric chain once formed.

Each oligomeric chain may, in addition to the •••M-O-M-O-M-O••• backbone and plurality of M-OH moieties, further comprise at least one aminoalkyl group. The at least one aminoalkyl group may be bonded to a Si atom in the oligomeric chain. There may be an aminoalkyl group bonded to each Si atom in the oligomeric chain backbone. The aminoalkyl group may be an amino-substituted alkyl group, e.g., aminomethyl, aminoethyl, aminopropyl, aminobutyl, aminopentyl, aminohexyl, aminoheptyl, aminooctyl, aminononyl or aminodecyl. The aminoalkyl group may linear or branched. The aminoalkyl group may comprise a primary, secondary or tertiary amine. The alkyl chain of the aminoalkyl group may comprise less than 15 carbon atoms, or may be less than 15 carbon atoms in length, e.g., may have less than 15, or less than 13, 10, 8, 6, 4, or 2 carbon atoms, e.g., may have between 15 and 1 carbon atoms, or between 15 and 8, 10 and 5, or 8 and 1 carbon atoms, e.g., may have 15, 14, 13, 12, 11, 10, 9, 8, 7, 6, 5, 4, 3, 2 or 1 carbon atoms, or may be less than 15 carbon atoms in length, or less than 13, 10, 8, 6, 4, or 2 carbon atoms, e.g., may be between 15 and 1 carbon atoms in length, or between 15 and 8, 10 and 5, or 8 and 1 carbon atoms, e.g., may be 15, 14, 13, 12, 11, 10, 9, 8, 7, 6, 5, 4, 3, 2 or 1 carbon atoms in length. One or more of the amino-substituted alkyl groups may also comprise, as a substituent, one or more N-(aminoalkyl) groups. Each N-(aminoalkyl) group may independently be an amino-substituted alkyl group, e.g., N-aminomethyl, N-aminoethyl, N-aminopropyl, N-aminobutyl, N-aminopentyl, N-aminohexyl, N-aminoheptyl, N-aminooctyl, N-aminononyl or N-aminodecyl. Each N-aminoalkyl group may independently be linear or branched. Each N-aminoalkyl group may independently comprise a primary, secondary or tertiary amine. The alkyl chain in each N-aminoalkyl group may be as described above for the alkyl chain of the aminoalkyl group. The aminoalkyl group may be —$C_3H_6NH_2$, —$C_3H_6NHC_2H_4NH_2$, —$CH_6N(CH_3)_2$, —$C_3H_6N(C_2H_5)_2$, —$C_3H_6NH(CH_3)$, or —$C_3H_6NH(C_2H_5)$, —$C_2H_4N(C_2H_5)_2$, or —$CH_2N(C_2H_5)_2$.

In one embodiment, the sorbent material comprises porous silica having a plurality of groups of formula —$O(MOAX)_nH_{n+1}$ on the surface thereof, wherein:
each M is, independently, Si, Zr or Ti,
each A is, independently, O or $(CH_2)_m$, where m is from 1 to 6,
each X is, independently, either OH or an aminoalkyl group, and
n is from 2 to 5;
with the proviso that none of said groups of formula —$O(MOAX)_nH_{n+1}$ contains an M-$(CH_2)_m$-M group. At least one M may be either Zr or Ti. Each A may be O or $(CH_2)_m$ where m is from 1 to 6. Each A may be $(CH_2)$, $(CH_2)_2$, $(CH_2)_3$, $(CH_2)_4$, $(CH_2)_5$, or $(CH_2)_6$. The $(CH_2)_m$ chain may be linear or branched. Each A may be O or $(CH_2)_m$ where m is 1 or 2. Each X may be OH or an aminoalkyl group. At least one X may be an aminoalkyl group, where the aminoalkyl group is as described above. The sorbent material according to the present invention may comprise porous silica having a plurality of groups of formula —$O(MOAX)_nH_{n+1}$ on the surface thereof where n may be 2 to 5, 2 to 4, 2 to 3, 3 to 5 or 3 to 4, or n may be 2, 3, 4 or 5, and n must be an integer.

In another embodiment the sorbent material comprises porous silica having a plurality of groups of formula —$O_{4-z}(M)A_iX_{z-i-k}R''_k$ on the surface thereof, wherein:
each M is, independently, Ti, Zr, Hf, Sn, Th, Pb, Si, or Ge;
each A is, independently, either OH or R (where R is an alkyl group $C_nH_{2n+1}$, and n is from 1 to 18);
each R'' is an aminoalkyl group [$(CH_2)_m$-(Amino group1)], where m is from 1 to 6;
each X is a [M'(oxo-hydroxyl-alkyl-aminoalkyl)M''(oxo-hydroxyl-alkyl-aminoalkyl)] group of formula [$(OM')_j${$(OH)_n(C_bH_{2b+1})_c[(CH_2)_d$-(Aminogroup2)$]_e$}{$(OM'')_f(OH)_g(C_hH_{2h+1})_p[(CH_2)_q$-(Amino group3)$]_v$}], wherein each M' is, independently, Si, Ti, Zr, or Hf and each M'' is, independently, Si, Ti, Zr, or Hf; z is from 1 to 3; i is from 0 to 3; (i+k) is from 0 to 3; j is 0 or 1; a is from 0 to 3; b is from 1 to 6; c is from 0 to 3; d is from 1 to 6; e is from 0 to 3; (a+c+e) is 3; f is 0 or 1; g is from 0 to 3; h is from 1 to 6; p is from 0 to 3; q is from 1 to 6; v is from 0 to 3; and (g+p+v) is 3.

The sorbent material may have a mean pore size of between about 2 and about 10 nm. The sorbent material may have a mean pore size as described with respect to step a) in the section entitled 'Silica Substrate'. The sorbent material may have a bimodal distribution of pore sizes. In this case there may be a first population of pores having a mean diameter of 2 to about 6 nm, e.g., about 4 nm, and a second population of pores having a mean diameter of 6 to about 10 nm, e.g., about 8 nm. The first and second population of pores may be as described with respect to step a) in the section entitled 'Silica Substrate'. The sorbent material may be particulate. The sorbent material may have a mean particle diameter of less than about 100 μm. The particle diameter may be as described with respect to step a) in the section entitled 'Silica Substrate'.

The sorbent material may have a specific surface area of between about 300 and about 1000 m$^2$/g. It may have a void volume of between about 0.5 mL/g to about 1.5 mL/g, or between about 0.5 and about 1.0, 0.9 and 1.3, 1.0 and 1.5, or about 0.8, 0.9, 1.0, 1.1, 1.2, 1.3, 1.4 or 1.5 mL/g. The surface area or the void volume of the sorbent material may be as described with respect to step a) in the section entitled 'Silica Substrate'. The sorbent material may be a surface modified silica.

The sorbent material surface may, for example, be functionalised as shown in any one of structures A to H and M below, where X is either OH or an aminoalkyl group (R'') and M is Si, Zr, Ti, Hf, Sn, Th, Pb, or Ge as described above:

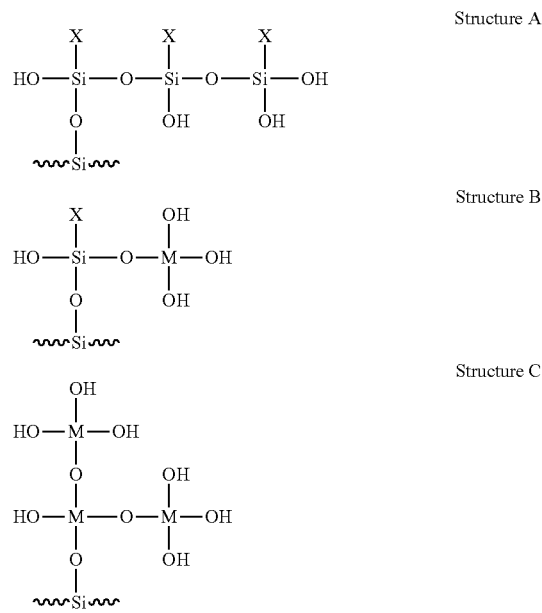

-continued

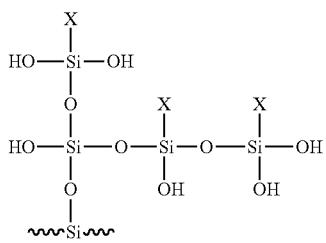

Structure D

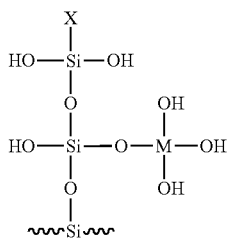

Structure E

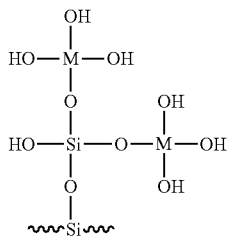

Structure F

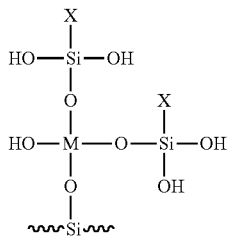

Structure G

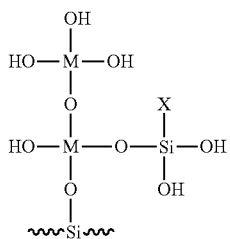

Structure H

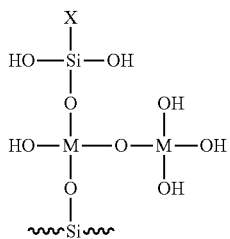

Structure M

Advantageously, the adsorption capacity of any one or more of the above sorbent materials for molybdenum is more than 400 mg Mo/g sorbent, or more than 450, 500, 550, 600, 650, 700, 750 or 800 mg Mo/g sorbent e.g., between about 400 and 1000 mg Mo/g sorbent, or between about 450 and 600, or 500 and 800, or 700 and 1000 mg Mo/g sorbent, e.g., 400, 450, 500, 550, 600, 650, 700, 750 or 800 mg Mo/g sorbent.

Advantageously, the adsorption capacity of any one or more of the above sorbent materials for tungsten is more than about 700 mg W/g sorbent, or more than 800, 900, 1000, 1200, 1400, 1600, 1800 or 2000 mg W/g sorbent, e.g., between about 700 and 2000 mg W/g sorbent, or between about 700 and 1500, 1200 and 1800, or 1500 and 2000 mg W/g sorbent, e.g., about 700, 800, 900, 1000, 1200, 1400, 1600, 1800 or 2000 mg W/g sorbent.

Purification and/or Concentration Methods

The present invention also relates to a method for purifying and/or concentrating a solution comprising a mixture of metal ions, said method comprising:

a) providing a solution comprising one or more contaminant species and one or more target species;

b) contacting the solution of step a) with a sorbent material comprising porous silica having a plurality of oligomeric chains on a surface thereof, said oligomeric chains having a backbone consisting of alternating oxygen and tetravalent M atoms, wherein each of said chains comprises a plurality of M-OH moieties, and wherein each M is independently selected from the group consisting of Si, Zr, Ti, Hf, Sn, Th, Pb, and Ge; and, c) separating the solution from the sorbent material as an eluate following step b).

Target and Contaminant Species

The term "mixture of metal ions" may refer to a mixture of contaminant species and target species wherein the contaminant species and/or the target species are metal ions. The "metal" constituting the metal ion may be any suitable metal, e.g., a transition metal, a lanthanoid or actinoid metal, a group I or group II metal, or a metalloid. The term "metal ion" as used herein may refer to a metal ion species, including a polyatomic metal ion species, e.g., a metal ion complex. For example, the term "metal ion" may encompass $MO_4^-$ or $MO_4^{2-}$ ions (where M is a metal as described herein), or may encompass metal ion complexes comprising one or more metal ions and one or more oxo, hydroxo, chloro, and/or aqua ligands when in aqueous solution, depending on the pH and salt concentration of that solution.

As used herein, the term 'target species' may refer to any species, e.g., ion or metal ion, that is desired to be collected for subsequent use. For example, in some embodiments, the target species is a species comprising a metal, and in particular a radioactive isotope of a metal, that is useful in nuclear medicine. The term 'target species' may refer to an ion, e.g., a metal ion comprising a metal, and in particular a radioactive isotope of a metal, that is useful in nuclear medicine. It will be understood that where the target species is an ion, there will be one or more counter-ions present when the target species is in aqueous solution.

As used herein, the term 'contaminant species' may refer to any species, e.g., ion or metal ion, that is not desired to be collected for subsequent use. For example, in some embodiments, the contaminant species is a species comprising a metal that is not useful in nuclear medicine, e.g., the contaminant species is a decay product of, or a parent or precursor species to, the target species. It will be understood that where the contaminant species is an ion, there will be one or more counter-ions present when the contaminant species is in aqueous solution.

In step a) above, the solution comprising one or more contaminant species may comprise a contaminant species of formula $[Z^1O_4]^{2-}$ where $Z^1$ may be Mo or may be W, e.g., the contaminant species may be $[MoO_4]^{2-}$ or may be

[WO$_4$]$^{2-}$. In step a) above, the solution comprising one or more target species may comprise a target species of formula [Z$^2$O$_4$]$^-$ where Z$^2$ may be Tc or Re, e.g., the target species may be [TcO$_4$]$^-$ or may be [ReO$_4$]$^-$. Z$^1$ may be radioactive, e.g., $^{99}$Mo, or $^{188}$W, or Z$^2$ may be radioactive, e.g., $^{99m}$Tc, or $^{188}$Re, or both Z$^1$ and Z$^2$ may be radioactive. Therefore, in step a) above, the contaminant species may be [$^{99}$MoO$_4$]$^{2-}$ or may be [$^{188}$WO$_4$]$^{2-}$ and the target species may be [$^{99m}$TcO$_4$]$^-$ or may be [$^{188}$ReO$_4$]$^-$, e.g., when the contaminant species is [$^{99}$MoO$_4$]$^{2-}$, the target species may be [$^{99m}$TcO$_4$]$^-$, or when the contaminant species is [$^{188}$WO$_4$]$^{2-}$, the target species may be [$^{188}$ReO$_4$]$^-$.

In step a) above, the contaminant species may be a D$^{4+}$ ion, where D may be selected from the group consisting of Ti, Ge, Zr, Sn and Hf. The contaminant species may be, for example, Ti$^{4+}$, Ge$^{4+}$, Zr$^{4+}$, Sn$^{4+}$ or Hf$^{4+}$. In step a) above, the target species may be an X$^{3+}$ ion, where X may be selected from the group consisting of Sc, Ga, Y, In or Lu. The target species may be, for example, Sc$^{3+}$, Ga$^{3+}$, Y$^{3+}$, In$^{3+}$ or Lu$^{3+}$. D may be radioactive, e.g., $^{44}$Ti, $^{68}$Ge, $^{89}$Zr, $^{110}$Sn, $^{113}$Sn or $^{172}$Hf, or X may be radioactive, e.g., $^{44}$Sc, $^{68}$Ga, $^{89m}$Y, $^{110m}$In, $^{113m}$In or $^{172}$Lu, or both D and X may be radioactive. When X is $^{44}$Sc, D may be $^{44}$Ti. When X is $^{68}$Ga, D may be $^{68}$Ge. When X is $^{89m}$Y, D may be $^{89}$Zr. When X is $^{110m}$In, D may be $^{110}$Sn. When X is $^{113m}$In, D may be $^{113}$Sn. When X is $^{172}$Lu, D may be $^{172}$Hf. It will be understood by those skilled in the art that 'X$^{3+}$' and 'D$^{4+}$' ions as described in this paragraph and elsewhere may be hydrated and/or hydroxylated in aqueous solution. For example they may be in the form [X(OH)$_{3-y}$]$^{y+}$ where 0≤y≤3 or [X(OH)$_{3+i}$]$^{i+}$ where 1≤i≤3, or may be in the form [D(OH)$_{4-w}$]$^{w+}$ where 0≤w≤4 or [D(OH)$_{4+j}$]$^{j+}$ where 1≤j≤4. 'X$^{3+}$' and 'D$^{4+}$' ions as described in this paragraph and elsewhere may be chloro complexes of X$^{3+}$ and D$^{4+}$ ions in aqueous solution, where the aqueous solution comprises chloride ions, and therefore may be in the form [X(Cl)$_{3-y}$]$^{y+}$ where 0≤y≤3 or [X(Cl)$_{3+i}$]$^{i+}$ where 1≤i≤3, or may be in the form [D(Cl)$_{4-w}$]$^{w+}$ where 0≤w≤4 or [D(Cl)$_{j+4}$]$^{j+}$ where 1≤j≤4. 'X$^{3+}$' and 'D$^{4+}$' ions as described in this paragraph and elsewhere may also be mixed ligand complexes comprising any one or more of oxo, hydroxo, chloro, and/or aqua ligands in aqueous solution. Methods of determining the formula of aqueous complexes are known in the art, and include, for example, UV-visible spectroscopy, ion-exchange, conductivity, etc.

The provided solution of step a) comprising one or more contaminant species and one or more target species may further comprise a saline solution. The saline solution may comprise any suitable soluble salt, e.g., it may comprise sodium chloride or ammonium or another group I or II chloride, e.g., potassium chloride, or any water soluble ammonium or group I or II sulfate, carbonate, chloride, acetate, sulfate, chloride, nitrate, iodide or bromide salt. The total salt concentration may be any suitable concentration, e.g., it may be about 0.1 M, or between about 0.01 and about 1 M, or between about 0.01 and about 0.1, 0.1 and 1, 0.05 and 0.5, or 0.5 and 1, e.g., 0.01, 0.05, 0.1, 0.2, 0.3, 0.4, 0.5, 0.6, 0.7, 0.8, 0.9 or 1 M. The total salt concentration may be about 1% (w/v), or between about 0.1 and about 10% (w/v), or between about 0.1 and about 1, 1 and 2, 1 and 5, 1 and 10, 5 and 10, or 6 and 8% (w/v), e.g., 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10% (w/v). Where the salt is sodium chloride, the total salt concentration may be between about 0.1 and about 10% (w/v). Where the salt is an ammonium or group I or II nitrate or acetate salt, the concentration may be about 5 M, e.g., between about 1 M and about 10 M, or between about 0.1 and 8 M, 0.1 and 1 M, 1 and 6 M, 4 and 10 M, or 4 and 6 M, e.g., about 1, 2, 3, 4, 5, 6, 7, 8, 9, or 10 M. The total salt concentration may be the total concentration of counteranions in the solution. The provided solution of step a) comprising or more contaminant species and one or more target species may comprise water.

The sorbent material in step b) above may be as described above in the section entitled 'Sorbent material', e.g., the sorbent material may be particulate. The sorbent material in step b) above may be produced by the method described in the section entitled 'Sorbent material production'. The choice of sorbent material may be contingent upon the desired function of the sorbent as described in the following sections. In particular, the sorbent materials of the present invention may be capable of retaining and/or covalently binding certain contaminant species, e.g., molybdate ([MoO$_4$]$^{2-}$) and/or tungstate ([WO$_4$]$^{2-}$) ions, or capable of retaining and/or reversibly binding certain target species, e.g., pertechnetate ([TcO$_4$]$^-$) and/or perrhenate ([ReO$_4$]$^-$), and may therefore be suitable for use in radioisotope separation, purification and/or concentration processes and for processes used in $^{9m}$Tc- and $^{188}$Re-generator production.

For example, in one embodiment, the sorbent material is chosen such that the oligomeric chains comprise a plurality of M-OH moieties and where the oligomeric chains are devoid of aminoalkyl groups, wherein at least one M is not Si, and the sorbent material applied in purification ("catch without release") processes. Sorbent materials used in "catch without release" processes may be capable of retaining and/or covalently binding certain contaminant species, e.g., molybdate ([MoO$_4$]$^{2-}$) and/or tungstate ([WO$_4$]$^{2-}$) ions as described below in the section entitled 'Purification "catch without release"'.

In another embodiment, the sorbent material is chosen such that the oligomeric chains comprise a plurality of M-OH moieties and a plurality of aminoalkyl groups, wherein at least one M is Si, and the sorbent material applied in purification and/or concentration ("catch and release") processes. Sorbent materials used in "catch and release" processes may be capable of retaining and/or covalently binding certain contaminant species, e.g., molybdate ([MoO$_4$]$^{2-}$) and/or tungstate ([WO$_4$]$^{2-}$) ions and may be capable of retaining and/or reversibly binding certain target species, e.g., pertechnetate ([TcO$_4$]$^-$) and/or perrhenate ([ReO$_4$]$^-$) as described below in the section entitled 'Purification and concentration "catch and release" (I)'.

In yet another embodiment, the sorbent material is chosen such that the oligomeric chains comprise a plurality of Si—OH moieties and a plurality of aminoalkyl groups, wherein all M atoms are Si, and the sorbent material applied in purification and/or concentration ("catch and release") processes. Sorbent materials used in "catch and release" processes may be capable of retaining and/or reversibly binding certain target species, e.g., pertechnetate ([TcO$_4$]$^-$) and/or perrhenate ([ReO$_4$]$^-$) as described below in the section entitled 'Purification and concentration "catch and release" (II)'.

In the above embodiments, the contacting of step b) may comprise passing the solution of step a) through the sorbent material. Any suitable means of passing the solution through the sorbent material may be used, e.g., passing the solution through a column comprising the sorbent material. The passing may be conducted under pressure, or may be conducted using gravitational force.

Purification "Catch without Release"

In one embodiment of the purification and/or concentration method described above, the sorbent material comprising porous silica has a plurality of oligomeric chains on a surface thereof, said oligomeric chains having a backbone consisting of alternating oxygen and tetravalent M atoms, wherein each of said chains comprises a plurality of M-OH moieties, wherein each M is independently selected from the group consisting of Si, Zr, Ti, Hf, Sn, Th, Pb, and Ge and wherein the oligomeric chains of the sorbent material comprise at least one M that is not Si. The sorbent material is advantageously devoid of aminoalkyl groups.

For example, the sorbent material may be functionalised with any one or more of the oligomeric chains as shown in the non-limiting Structures (i) to (v) below, where each M is independently Si, Zr, Ti, Hf, Sn, Th, Pb, or Ge and at least one M is not Si.

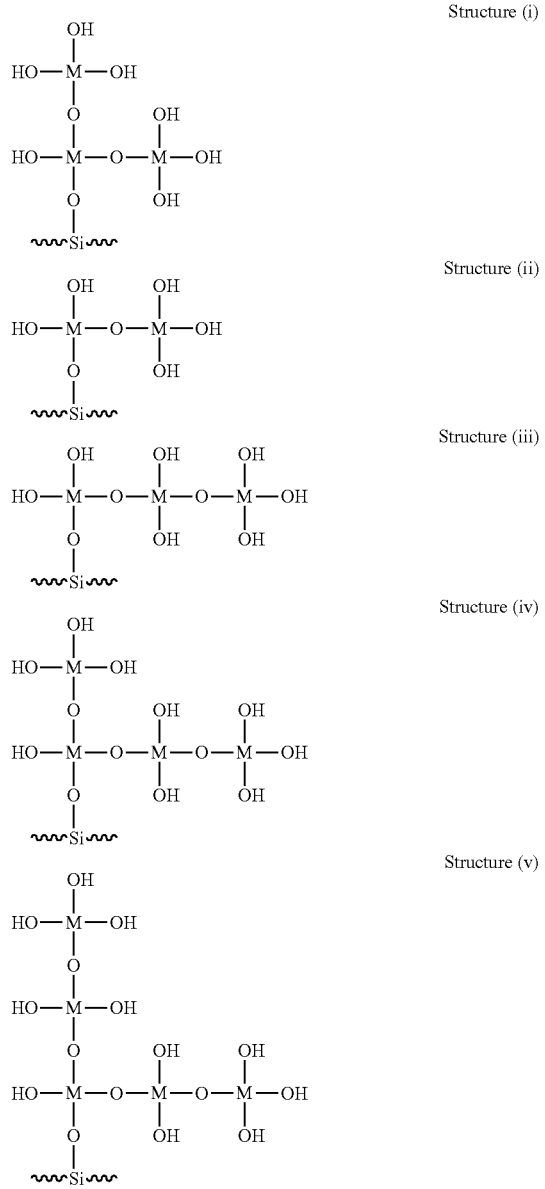

The sorbent material applied in purification ("catch without release") processes may be capable of retaining and/or covalently binding certain contaminant species, e.g., $[Z^1O_4]^{2-}$ ions including molybdate ($[MoO_4]^{2-}$) and/or tungstate ($[WO_4]^{2-}$) as described in the following paragraphs. Using the sorbent material as described in this section in "catch without release" processes advantageously provides a plurality of M-OH sites to which contaminant ions may bind irreversibly, which may in turn assist in the separation and/or purification of the target species in or from the solution.

In step a), the solution comprising one or more contaminant species and one or more target species may be as described in the section above entitled 'Target and contaminant species'. The solution may comprise saline as also described in the section above entitled 'Target and contaminant species'.

In the purification and/or concentration method described in the section entitled 'Purification and/or concentration methods', where the sorbent material of step b) is as described in this section, the contacting of step b) may cause the contaminant species $[Z^1O_4]^{2-}$ to bind irreversibly to the sorbent material. The irreversible binding may comprise formation of at least one M-O—$Z^1$ linkage, wherein M is either Si, Zr, Ti, Hf, Sn, Th, Pb, or Ge, e.g., M is Si, Zr or Ti. It may comprise formation of at least two M-O—$Z^1$ linkages per M or per $Z^1$. It may comprise the formation of a bis-μ-oxo bridge between the M and $Z^1$ metal centres. The term 'irreversible binding' may encompass covalent binding of the $[Z^1O_4]^{2-}$ ions to the M-OH moieties or $MO_4$ units in the oligomeric chains covalently coupled to the surface of the porous silica substrate. The 'irreversible binding' may prevent the $[Z^1O_4]^{2-}$ ions from being re-solubilised. The 'irreversible binding' may prevent the $[Z^1O_4]^{2-}$ ions from being re-solubilised under the normal conditions of use of the porous silica sorbent material. The $[Z^1O_4]^{2-}$ ions may compete with the $[Z^2O_4]^-$ target ions for irreversible binding sites such that no, or substantially no, target species bind irreversibly to the sorbent material. It will be understood that there may be conditions under which "irreversibly bound" atoms may be detached, but that these conditions may not prevail under normal use, or may not prevail under normal use without a further regeneration step as described below.

In the purification and/or concentration method described in the section entitled 'Purification and/or concentration methods', where the sorbent material of step b) is as described in this section, the contacting of step b) may cause the contaminant species $D^{4+}$, or a hydrate or hydroxo complex thereof, to bind irreversibly to the sorbent material. The irreversible binding may comprise formation of at least one M-O-D linkage, wherein M is either Si, Zr, Ti, Hf, Sn, Th, Pb, or Ge, e.g., M is Si, Zr or Ti and D is Ti, Ge, Zr, Sn or Hf. It may comprise formation of at least two M-O-D linkages per M or per D. It may comprise the formation of a bis-μ-oxo bridge between the M and D metal centres. The term 'irreversible binding' may encompass covalent binding of $D^{4+}$, $[D(OH)_3]^+$, $[D(OH)_2]^{2+}$, or $[D(OH)]^{3+}$ ions, or $[D(OH)_4]$ complexes, to the M-OH moieties or $MO_4$ units in the oligomeric chains covalently coupled to the surface of the porous silica substrate. The 'irreversible binding' may prevent the $D^{4+}$, $[D(OH)_3]^+$, $[D(OH)_2]^{2+}$, or $[D(OH)]^{3+}$ ions, or $[D(OH)_4]$ complexes from being re-solubilised.

In the purification and/or concentration method described in the section entitled 'Purification and/or concentration methods', the sorbent material used in step b) may be devoid of aminoalkyl functional groups. The porous silica sorbent devoid of aminoalkyl functional groups may be used in step b) of the method to purify a solution comprising a mixture of metal ions. In this method, step b) may be performed to remove up to 100% by mole or mass of the $[Z^1O_4]^{2-}$ or $D^{4+}$ ions from the provided solution. The contacting of step b) may be performed to remove between 100 and 50% by mole or mass of the $[Z^1O_4]^{2-}$ or $D^{4+}$ ions from the provided solution, or may be performed to remove between 100 and 95, 100 and 85, 95 and 85, 90 and 60, or 85 and 50% by mole or mass of the $[Z^1O_4]^{2-}$ or $D^{4+}$ ions from the provided solution, e.g., 100, 99, 98, 97, 96, 95, 94, 93, 92, 91, 90, 85, 80, 75, 70, 65, 60, 55 or 50% by mole or mass of the $[Z^1O_4]^{2-}$ or $D^{4+}$ ions from the provided solution. The porous silica sorbent devoid of aminoalkyl functional groups may allow the target species of formula $[Z^2O_4]^-$ or $X^{3+}$ ions to pass through the sorbent material without binding to the sorbent material, or to the surface of the sorbent material, or to the $MO_4$ groups covalently coupled to the surface of the sorbent material, or may allow the target species of formula $[Z^2O_4]^-$ or $X^{3+}$ to bind less strongly to the sorbent than $[Z^1O_4]^{2-}$ or $D^{4+}$ ions. It may allow the target species of formula $[Z^2O_4]^-$ or $X^{3+}$ to pass through the sorbent material without binding permanently to the sorbent material. The porous silica sorbent devoid of aminoalkyl functional groups may allow 100% by mole or mass of the target species of formula $[Z^2O_4]^-$ or $X^{3+}$ to pass through the sorbent material, or between about 100 and 85%, or between about 100 and 95, 100 and 90, 95 and 85 or 90 and 85% by mole or mass of the target species of formula $[Z^2O_4]^-$ or $X^{3+}$ to pass through the sorbent material, e.g., 100, 99, 98, 97, 96, 95, 94, 93, 92, 91, 90, 89, 88, 87, 86 or 85% by mole or mass of the target species of formula $[Z^2O_4]^-$ or $X^{3+}$ to pass through the sorbent material.

Step c) may comprise separating the solution from the sorbent material after the contacting of step b) as an eluate. Said eluate may comprise the target species and trace amounts of $[Z^1O_4]^{2-}$ or $D^{4+}$ ions, e.g., between about 5 ppm and 0.001 ppm $[Z^1O_4]^{2-}$ or $D^{4+}$, or between about 5 ppm and about 1 ppm, or 1 and 0.1 ppm, or 0.1 and 0.01 ppm, or 0.01 and 0.001 ppm, or less than about 5 ppm, 1 ppm, 0.5 ppm, 0.1 ppm, 0.05 ppm, 0.01 ppm, 0.005 ppm, or 0.001 ppm, e.g., about 5 ppm, 1 ppm, 0.5 ppm, 0.1 ppm, 0.05 ppm, 0.01 ppm, 0.005 ppm, or 0.001 ppm or optionally less than about 0.001% radioactivity of target and/or contaminant species in the eluate per total radioactivity of target and/or contaminant species on the sorbent column. The eluate of step c), after contacting with the sorbent material in step b), may comprise a relatively higher proportion of target species and a relatively lower proportion of contaminant species with respect to the provided solution of step a) and hence be said to purify the provided solution. For example, the eluate of step c), after contacting with the sorbent material in step b), may essentially comprise the target ions in solution, e.g., the eluate may comprise purified target species. The method may thus purify the provided solution of step a) by binding the contaminant ions strongly, e.g., irreversibly, and allowing the target species to pass into the eluate.

A non-limiting example of a purification ("catch without release") process setup is given in FIG. 10. In FIG. 10, a normal saline eluent (A) is provided to a generator column (B) comprising a functionalised silica sorbent as described in this section. The eluate of this generator column, which is the solution of step a) in the method described in this section, is then passed through a purification column (C) that also comprises a sorbent material as described in this section, which traps contaminant species as described above, allowing the target species to pass into the collected eluate (D).

The "catch without release" process described above may further comprise step d) regenerating the sorbent material, wherein said regenerating comprises adding a regenerating solution to the sorbent material. The regenerating solution may be added to the sorbent material after the contacting of step b) and the separation of the eluate in step c). The regenerating step may comprise passing the regenerating solution through the sorbent material. As described above, the sorbent material may comprise irreversibly bound $[Z^1O_4]^-$ or $D^{4+}$ species bound, for example, through M-O—$Z^1$ or M-O-D linkages, after step c), and therefore prior to adding the regenerating solution. Advantageously, the regenerating solution may reverse the 'irreversible binding' of the $[Z^1O_4]^{2-}$ or $D^{4+}$ species, for example, by disrupting, cleaving and/or reversing the M-O—$Z^1$ or M-O-D linkages such that $[Z^1O_4]^{2-}$ or $D^{4+}$ species move into the regenerating solution and M-OH moieties are restored on the surface of the sorbent material.

The regenerating solution of step d) may be basic. Any suitable basic solution may be used, for example, a solution comprising hydroxide ions. The regenerating solution may comprise a solution of one or more group I or II metal hydroxides, e.g., lithium hydroxide, sodium hydroxide, or potassium hydroxide. It may comprise ammonium hydroxide. It may comprise a combination of sodium hydroxide, potassium hydroxide and/or ammonium hydroxide. Where the regenerating solution comprises hydroxide ions, the total hydroxide ion concentration of the regenerating solution may be between about 0.01 and 1.0 M, e.g., between about 0.01 and 0.1 M, or 0.1 and 0.6 M, or 0.5 and 1.0 M, e.g., about 0.01, 0.05, 0.1, 0.2, 0.3, 0.4, 0.5, 0.6, 0.7, 0.8, 0.9 or 1.0 M.

After the regenerating of step d), the sorbent material may comprise less than about 0.01% (w/w) $Z^1$ or D, or between about 0.001 and 1% (w/w), or between about 0.001 and 0.01, or 0.01 and 0.1, or 0.1 and 1.0% (w/w), e.g., about 0.001, 0.01, 0.1, or 1.0%/(w/w). The % (w/w) unit may represent the percent by mass of the elements $Z^1$ or D relative to the mass of the sorbent material used in step b) and/or d). After the regenerating of step d), the sorbent material may be reused in the method.

Advantageously, the sorbent materials described in this section have an adsorption capacity for molybdenum of more than 450 mg Mo/g sorbent and/or an adsorption capacity for tungsten of more than about 850 mg W/g sorbent, as described in the section entitled 'Sorbent material'.

A non-limiting example of a purification ("catch without release") process setup comprising a regeneration step is given in FIG. 11. In FIG. 11, a normal saline eluent (A) is provided to a generator column (K1) comprising a functionalised silica sorbent as described in this section. The eluate of this generator column, which is the solution of step a) in the method described in this section, is then passed through a purification column (K2) that also comprises a sorbent material as described in this section, which traps contaminant species as described above, allowing the target species to pass (EF-A), via a pump (P), into the collected eluate (F). After collection, an 0.5 M NaOH solution (B) is passed through the column (K2) to reverse the irreversible binding of the $[Z^1O_4]^{2-}$ or $D^{4+}$ species and regenerate the column. The eluate produced by this step (EF-B,C) is collected in a separate receptacle (W). Finally, a water wash (C) is added and the water wash waste collected (EF-B,C) in the same separate waste receptacle (W).

Purification and Concentration "Catch and Release" (I)

In another embodiment of the purification and/or concentration method described in the section entitled 'Purification and/or concentration methods', the sorbent material comprising porous silica has a plurality of oligomeric chains on a surface thereof, said oligomeric chains having a backbone consisting of alternating oxygen and tetravalent M atoms, wherein each of said chains comprises a plurality of M-OH moieties, wherein each M is independently selected from the group consisting of Si, Zr, Ti, Hf, Sn, Th, Pb, and Ge and wherein the oligomeric chains of the sorbent material comprise at least one M that is Si, at least one aminoalkyl group attached to the at least one Si, and at least one M that is not Si.

For example, the sorbent material may be functionalised with any one or more of the oligomeric chains shown in the non-limiting Structures (vi) to (x) below, where each M is independently Si, Zr, Ti, Hf, Sn, Th, Pb, or Ge but at least one M is not Si, and R″ is an aminoalkyl group, for example an aminoalkyl group R″ as described in the section entitled 'Aminoalkyl silane compounds' above.

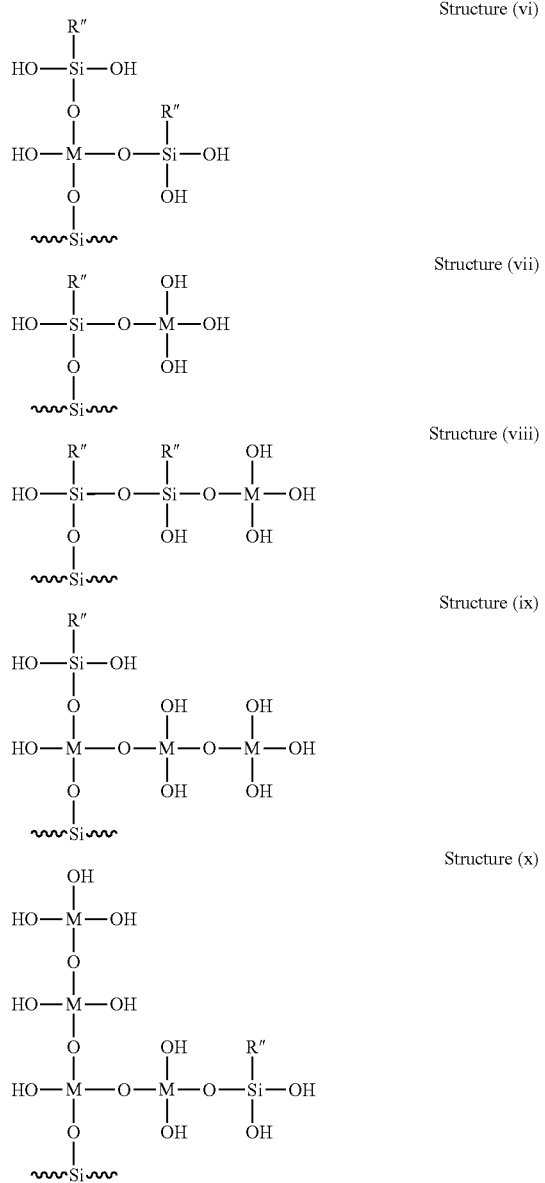

Structure (vi)

Structure (vii)

Structure (viii)

Structure (ix)

Structure (x)

The sorbent material applied in purification and/or concentration ("catch and release") processes may be capable of retaining and/or covalently binding certain contaminant species, e.g., molybdate ($[MoO_4]^{2-}$) and/or tungstate ($[WO_4]^{2-}$) ions and may be capable of retaining and/or reversibly binding certain target species, e.g., pertechnetate ($[TcO_4]^-$) and/or perrhenate ($[ReO_4]^-$) as described in the following paragraphs. Use of a sorbent material as described in this section in "catch and release" processes advantageously provides a plurality of M-OH sites to which contaminant ions may bind irreversibly, and also advantageously provides a plurality of aminoalkyl sites to which target ions may bind reversibly, which may in turn assist in the separation, purification and/or concentration of the target species in or from a solution comprising contaminant species.

In step a), the solution comprising one or more contaminant species may be as described in the section entitled 'Target and contaminant species', e.g., the solution of step a) may comprise any water soluble ammonium or group I or II sulfate, acetate, or nitrate salt at a concentration of from about 0.1 M to about 5 M, and may additionally comprise sodium chloride solution at a concentration of less than about 0.05% (w/v).

In the purification and/or concentration method described in the section entitled 'Purification and/or concentration methods', the sorbent material of step b) described in this section comprising at least one aminoalkyl group covalently coupled to the surface of the silica and comprising at least one M that is Si and one M that is not Si may be used to purify a solution comprising one or more contaminant species and one or more target species, wherein the contacting of step b) may be performed to remove up to 100% by mole or mass of the contaminant species (e.g., $[Z^1O_4]^{2-}$ or $D^{4+}$ ions) from the provided solution as described in the section entitled 'Purification "catch without release"'.

Simultaneously, the porous silica sorbent material comprising at least one aminoalkyl group covalently coupled to the surface of the silica may allow the reversible binding of the target species (e.g., of formula $[Z^2O_4]^-$ or $X^{3+}$) to the aminoalkyl groups during the contacting of step b). The aminoalkyl groups may be positively charged during the contacting of step b). The aminoalkyl groups may be positively charged due to the pH of the solution of step a) being less than about 6, or between about pH 5 and pH 2, e.g., about pH 6, 5.5, 5, 4.5, 4, 3.5, 3, 2.5, or about pH 2. The positively charged aminoalkyl groups may interact with target $[Z^2O_4]^-$ ions to form an ionically bonded ion pair. The ionic bond may be reversible. The positively charged aminoalkyl groups may additionally or alternatively interact with $[Z^2O_4]^-$ or $X^{3+}$ ions in a Lewis acid-Lewis base interaction, and/or through the formation of hydrogen bonds and/or through van der Waals or dispersion forces. The porous silica sorbent comprising at least one aminoalkyl group covalently coupled to the surface of the silica may bind, ionically or otherwise, up to 100% by mole or mass of the target species of formula $[Z^2O_4]^-$ or $X^{3+}$, or between about 100 and 50%, or between about 100 and 95, 100 and 80, 95 and 85, 100 and 70, 90 and 70, 100 and 55, 70 and 50% by mole or mass of the $[Z^1O_4]^{2-}$ or $X^{3+}$ ions from the provided solution, e.g., 100, 99, 98, 97 96, 95, 94, 93, 92, 91, 90, 85, 80, 75, 70, 65, 60, 55 or 50% by mole or mass. Where the porous silica sorbent comprising at least one aminoalkyl group covalently coupled to the surface of the silica has ionically or otherwise bound between 100 and 50% by mole or mass of the target species of formula $[Z^2O_4]^-$ or $X^{3+}$, step c) may comprise separating the solution from the sorbent material as an eluate following step b). This eluate collected in step c) may comprise substantially no target species and substantially no contaminant species. It may substantially comprise the further components of the provided solution of step a) as described in the section entitled 'Target and contaminant species'. Where the target and/or contaminant species are radioactive, the eluate collected in step c) may comprise radioactive decay by-products. The eluate collected in step c) may be collected in a receptacle. It may be discarded, or alternatively, may be reused as described in the section entitled 'Generator'.

The purification and/or concentration method described in this section may further comprise step d') contacting an eluting solution with the sorbent material of step b) said eluting solution being capable of reversing the binding of the target species to the sorbent, whereby the target species passes into the eluting solution. The eluting solution of step d') may release the target species of formula $[Z^2O_4]^-$ or $X^{3+}$ from the ionic interactions with charged aminoalkyl groups on the sorbent material. Releasing the target species may comprise an ion-exchange reaction between the target species of formula $[Z^2O_4]^-$ or $X^{3+}$ and one or more anions comprising the eluting solution. These anions may be, for example, chloride, iodide, bromide, acetate, nitrate, sulfate or carbonate anions.

The eluting solution of step d') may comprise a saline solution. The saline solution may comprise any suitable soluble salt. The saline solution may comprise a sodium chloride solution. It may comprise ammonium or another group I or II chloride, e.g., potassium chloride, or any water soluble ammonium or group I or II sulfate, carbonate, chloride, acetate, sulfate, chloride, nitrate, iodide or bromide salt. The total salt concentration may be any suitable concentration, e.g., it may be about 0.15 M, or between about 0.01 and about 1 M, or between about 0.01 and about 0.15, 0.1 and 1, 0.05 and 0.5, or 0.5 and 1, e.g., 0.01, 0.05, 0.1, 0.15, 0.2, 0.3, 0.4, 0.5, 0.6, 0.7, 0.8, 0.9 or 1 M. The total salt concentration may be about 1% (w/v), or between about 0.1 and about 10% (w/v), or between about 0.1 and about 1, 1 and 2, 1 and 5, 1 and 10, 5 and 10, or 6 and 8% (w/v), e.g., 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10% (w/v). Where the salt is sodium chloride, the total salt concentration may be between about 0.1 and about 10% (w/v). Where the salt is an ammonium or group I or II nitrate or acetate salt, the concentration may be about 5 M, e.g., between about 1 M and about 10 M, or between about 0.1 and 8 M, 0.1 and 1 M, 1 and 6 M, 4 and 10 M, or 4 and 6 M, e.g., about 1, 2, 3, 4, 5, 6, 7, 8, 9, or 10 M. The eluting solution, in particular the salt, may be chosen such that the characteristics of the solution enable it to reverse the binding of the target species to the sorbent material. For example, the salt may be chosen for the charge density of its constituent ions. Advantageously, the concentration of the chosen salt in the eluting solution may also be adjusted to reverse the binding of the target species to the sorbent material, in particular, to minimise the volume of eluting solution required to reverse the binding of the target species.

The eluting solution of step d') may have a defined pH. The defined pH may be controlled by adding a buffer solution or by adding any suitable acid or base. The pH of the eluting solution may be greater than about pH 2, e.g., greater than pH 2, 3, 4, 5, 6, 7, 8, 9, 10, 11, 12, 13 or 14, or between about pH 4 and pH 8, or pH 2 and pH 5, or pH 6 and pH 10, e.g., pH 2, 3, 4, 5, 6, 7, 8, 9, 10, 11, 12, 13, or pH 14. The pH of the eluting solution may be greater than the pKa of the aminoalkyl group. The eluting solution of step d') may release up to 100% of the ionically or otherwise bound target species of formula $[Z^2O_4]^-$ or $X^{3+}$ from the sorbent material, or between about 100 and 85%, or between about 100 and 95, 100 and 90, or 95 and 85% by mole or mass, e.g., 100, 99, 98, 97, 96, 95, 94, 93, 92, 91, 90, 89, 88, 87, 86 or 85% by mole or mass of the target species of formula $[Z^2O_4]^-$ or $X^{3+}$. Step d') may further comprise collecting the eluting solution containing the target species in a receptacle. The eluting solution may comprise the target species. The receptacle may be separate to the receptacle containing the eluate of step c). The purification and concentration "catch and release" process may thus purify the provided solution by binding the contaminant ions irreversibly, and allowing the target species to pass through into the eluent, and may concentrate the target species as described below.

The "catch and release" process described above may concentrate the target species as follows: the solution provided in step a) may have a concentration of the target species of formula $[Z^2O_4]^-$ or $X^{3+}$ of $C_A$. After contacting this solution with a porous silica sorbent material comprising at least one aminoalkyl group covalently coupled to the surface of the silica to reversibly bind the target species, the target species may become reversibly bound to the surface of the sorbent. In step d'), the eluting solution capable of reversing the binding of the target species may then reverse the binding of the target species such that the target species pass into the eluting solution. The eluting solution collected after step d') may then have a total concentration of the target species of formula $[Z^2O_4]^-$ or $X^{3+}$ of $C_B$, wherein $C_A < C_B$. The volume of solution used in step a) may be greater than the volume of the eluting solution used in step d'. The volume of the eluting solution used in step d') may be chosen specifically to produce a certain concentration of target species, e.g., a small volume may be chosen to concentrate the target species relative to the initial provided solution.

The "catch and release" process described above may further comprise step e) regenerating the sorbent material, wherein said regenerating comprises adding a regenerating solution to the sorbent material. The regenerating solution may be added to the sorbent material after the contacting of step b), the separation of the eluate in step c), and the contacting of step d'). The regenerating step may comprise passing the regenerating solution through the sorbent material. As described above, the sorbent material may comprise $[Z^1O_4]^{2-}$ or $D^{4+}$ species irreversibly bound to the sorbent through, for example, M-O—$Z^1$ or M-O-D linkages, after step d') and therefore prior to adding the regenerating solution. Advantageously, the regenerating solution may reverse the 'irreversible binding' of the $[Z^1O_4]^{2-}$ or $D^{4+}$ species, for example, by disrupting, cleaving and/or reversing the M-O—$Z^1$ or M-O-D linkages such that $[Z^1O_4]^{2-}$ or $D^{4+}$ species move into the regenerating solution and M-OH moieties are restored on the surface of the sorbent material.

The regenerating solution of step e) may be basic, and may be as described for the regenerating solution of step c) in the section entitled 'Purification "catch without release"'.

After the regenerating of step e), the sorbent material may comprise less than about 0.01% (w/w) $Z^1$ or D as also described in the section entitled 'Purification "catch without release"'. The regenerating solution may be collected in a receptacle separate to the eluate of step c) and the eluting solution of step d') during or after the regenerating of step e). The collected regenerating solution may be discarded. After the regenerating of step e), the sorbent material may be reused in the method.

In the "catch and release" process above, step b) and/or step d') and/or step e) may comprise passing the solution through a column comprising the sorbent material. The column may be packed with sorbent material. The column may be a single use column, wherein once the capacity of the sorbent material to bind the contaminant species of formula $[Z^1O_4]^{2-}$ or $D^{4+}$ irreversibly has been reduced, the column may be discarded. The reduction in capacity of the sorbent material to bind $[Z^1O_4]^{2-}$ or $D^{4+}$ species irreversibly may be a reduction of about 100.%, or between about 100 and 90%, or between about 100 and 80%, or between about 90 and 80%, e.g., 100, 99, 98, 97, 96, 95, 94, 93, 92, 91, 90, 85 or 80% before the sorbent may be discarded. The reduction in capacity may be measured as the percentage of moles of contaminant species of formula $[Z^1O_4]^{2-}$ or $D^{4+}$ in the final eluent (after step e)) relative to the moles of contaminant species of formula $[Z^1O_4]^{2-}$ or $D^{4+}$ in the solution provided in step a) of the method.

The column may alternatively be a multiple use column. The number of uses for which the column is suitable may depend on the quantity of contaminant species of formula $[Z^1O_4]^{2-}$ or $D^{4+}$ in the solution and the volume of the solution passed through the column. For example, concentrated solutions of contaminant species and/or large volumes of solution may reduce the number of suitable reuses. As described above, once the capacity of the sorbent material to bind the contaminant species of formula $[Z^1O_4]^{2-}$ or $D^{4+}$ irreversibly has been reduced, e.g., by between about 100 and 80%, the column may be discarded. This reduction in capacity may occur after many reuses, e.g., after more than 10, 50 or 100 reuses, e.g., after about 50, 75, 100, 125 or 150 reuses. Advantageously, the regenerating step e) and the elution of reversibly bound target ions in step d) may increase the number of uses for which the column is suitable.

The sorbent materials described in this section may have an adsorption capacity for molybdenum of more than 450 mg Mo/g sorbent and/or an adsorption capacity for tungsten of more than about 850 mg W/g sorbent, as described in the section entitled 'Sorbent material'.

A non-limiting example of a purification and concentration ("catch and release") (I) process setup comprising a regeneration step is given in FIG. 12. In FIG. 12, a non-saline aqueous eluent (e.g., acetic acid/acetate and <0.05% NaCl solution mixture or <0.05% NaCl solution) (E) is provided to a generator column (K1) comprising a functionalised silica sorbent as described in the section entitled 'Purification "catch without release"' via an eluent flow circulation system (EFC). The eluate of this generator column, which is the solution of step a) in the method described in this section, is then passed through a purification column (K2) that comprises a sorbent material as described in this section, which traps contaminant species and target species as described above. The non-saline aqueous eluent (EF-E) that passes through the column (K2) is collected, via a pump (P), in a receptacle (E). The target species is then eluted from the column (K2) using a small volume of saline solution (C), and the eluate (EF-C) collected in a receptacle as a purified and concentrated solution of target species (F). After collection, an 0.5 M NaOH solution (B) is passed through the column (K2) to reverse the irreversible binding of the $Z^1O_4^{2-}$ or $D^{4+}$ species and regenerate the column. The eluate (EF-A,B) produced by this step is pumped (P) into a separate receptacle (W). Finally, a water wash (B) is added to the column (K2) and the water wash (EF-A,B) waste pumped (P) into the same separate waste receptacle (W).

Purification and Concentration "Catch and Release" (II)

In another embodiment of the purification and/or concentration method described in the section entitled 'Purification and/or concentration methods', the sorbent material comprising porous silica has a plurality of oligomeric chains on a surface thereof, said oligomeric chains having a backbone consisting of alternating oxygen and tetravalent M atoms, wherein each of said chains comprises a plurality of M-OH moieties, wherein each M atom is Si and wherein the oligomeric chains of the sorbent material comprise a plurality of aminoalkyl groups attached to the Si atoms.

For example, the sorbent material may be functionalised with any one or more of the oligomeric chains shown in the non-limiting Structures (xi) to (xv) below, where R" is an aminoalkyl group, for example an aminoalkyl group R" as described in the section entitled 'Aminoalkyl silane compounds'.

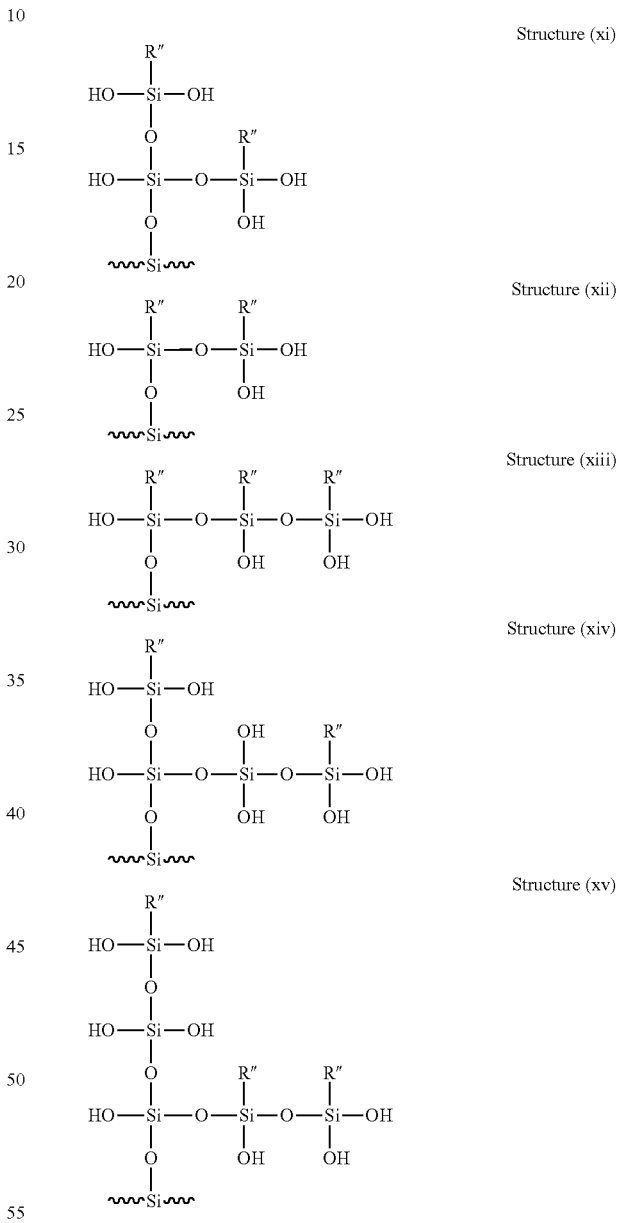

The sorbent material applied in the purification and/or concentration ("catch and release") processes in this section may be capable of retaining and/or reversibly binding certain target species, e.g., pertechnetate ($TcO_4^-$) and/or perrhenate ($ReO_4^-$) as described in the following paragraphs. Use of a sorbent material as described in this section in "catch and release" processes advantageously provides a plurality of aminoalkyl sites to which target ions may bind reversibly, which may in turn assist in the separation, purification and/or concentration of the target species in or from a solution comprising contaminant species.

In step a), the solution comprising one or more contaminant species may be as described in the section entitled 'Target and contaminant species'. Prior to step b) described below, the provided solution of step a) may be passed through a chlorine-selective sorbent column to remove or substantially remove any saline or salt. Passing the provided solution of step a) through a chlorine-selective sorbent column may advantageously reduce the concentration of chloride ions in the provided solution, as chloride ions may compete with the target species (e.g., of formula $[Z^2O_4]^-$ or $X^{3+}$) at reversible aminoalkyl group binding sites on the inventive sorbent material.

The porous silica sorbent described in this section comprising a plurality of aminoalkyl functional groups may be used in step b) of the method to purify and concentrate at least one target species from a solution comprising at least one target species and at least one contaminant species. In this method, step b) may be performed to bind reversibly up to 100% by mole or mass of the $[Z^2O_4]^-$ or $X^{3+}$ ions from the provided solution. The contacting of step b) may be performed to bind reversibly between 100 and 50% by mole or mass of the $[Z^2O_4]^-$ or $X^{3+}$ ions from the provided solution, or may be performed to bind reversibly between 100 and 95, 100 and 85, 95 and 85, 90 and 60, or 85 and 50% by mole or mass of the $[Z^2O_4]^-$ ions from the provided solution, e.g., 100, 99, 98, 97, 96, 95, 94, 93, 92, 91, 90, 85, 80, 75, 70, 65, 60, 55 or 50% by mole or mass of the $[Z^2O_4]^-$ or $X^{3+}$ ions from the provided solution. The porous silica sorbent comprising a plurality of aminoalkyl functional groups may allow the contaminant species of formula $[Z^1O_4]^{2-}$ or $D^{4+}$ to pass through the sorbent material without binding to the sorbent material, or to the surface of the sorbent material, or to any oligomeric chain groups covalently coupled to the surface of the sorbent material, or bind less strongly to the sorbent than $[Z^2O_4]^-$ or $X^{3+}$ ions. It may allow the contaminant species of formula $[Z^1O_4]^{2-}$ or $D^{4+}$ to pass through the sorbent material without binding reversibly or irreversibly to the sorbent material. The porous silica sorbent comprising a plurality of aminoalkyl functional groups may allow 100% by mole or mass of the contaminant species of formula $[Z^1O_4]^{2-}$ or $D^{4+}$ to pass through the sorbent material, or between about 100 and 85%, or between about 100 and 95, 100 and 90, 95 and 85 or 90 and 85% by mole or mass of the contaminant species of formula $[Z^1O_4]^{2-}$ or $D^{4+}$ to pass through the sorbent material, e.g., 100, 99, 98, 97, 96, 95, 94, 93, 92, 91, 90, 89, 88, 87, 86 or 85% by mole or mass of the contaminant species of formula $[Z^1O_4]^{2-}$ or $D^{4+}$ to pass through the sorbent material.

The porous silica sorbent material where each M is Si and where the sorbent material comprises at least one aminoalkyl group covalently coupled to the surface of the silica may allow the reversible binding of the target species (e.g., of formula $[Z^2O_4]^-$) to the aminoalkyl groups during the contacting of step b) as described in the section entitled 'Purification and concentration "catch and release (I)' above. For example, the aminoalkyl groups may be positively charged during the contacting of step b), and the positively charged aminoalkyl groups may interact with target $[Z^2O_4]^-$ or $X^{3+}$ ions to form an ionically bonded ion pair. The ionic bond may be reversible. The sorbent may ionically bind up to 100% by mole or mass of the target species of formula $[Z^2O_4]^-$ or $X^{3+}$, or between about 100 and 50%, or between about 100 and 95, 100 and 80, 95 and 85, 100 and 70, 90 and 70, 100 and 55, 70 and 50% by mole or mass of the $[Z^1O_4]^{2-}$ or $X^{3+}$ ions from the provided solution, e.g., 100, 99, 98, 97 96, 95, 94, 93, 92, 91, 90, 85, 80, 75, 70, 65, 60, 55 or 50% by mole or mass. During the contacting of step b), the $[Z^2O_4]^-$ or $X^{3+}$ target ions may compete with the $[Z^1O_4]^{2-}$ or $D^{4+}$ contaminant ions for reversible binding sites such that no, or substantially no, contaminant species bind reversibly (or irreversibly) to the sorbent material.

Step c) may comprise separating the solution from the sorbent material after the contacting of step b) as an eluate. The eluate may be collected in a separate receptacle. Said eluate may comprise the contaminant species and trace amounts of $[Z^2O_4]^-$ or $X^{3+}$ ions, e.g., between about 5 ppm and 0.001 ppm $[Z^2O_4]^-$ or $X^{3+}$, or between about 5 ppm and about 1 ppm, or 1 and 0.1 ppm, or 0.1 and 0.01 ppm, or 0.01 and 0.001 ppm, or less than about 5 ppm, 1 ppm, 0.5 ppm, 0.1 ppm, 0.05 ppm, 0.01 ppm, 0.005 ppm, or 0.001 ppm, e.g., about 5 ppm, 1 ppm, 0.5 ppm, 0.1 ppm, 0.05 ppm, 0.01 ppm, 0.005 ppm, or 0.001 ppm $[Z^2O_4]^-$ or $X^{3+}$, or optionally less than about 0.001% radioactivity of target and/or contaminant species in the eluate per total radioactivity of target and/or contaminant species on the sorbent column. The eluate of step c), after contacting with the sorbent material in step b), may essentially comprise the contaminant ions in solution. The method may thus purify the provided solution of step a) by allowing collecting of the eluate comprising the contaminant ions, allowing the target species be eluted in a separate, subsequent step.

The purification and/or concentration method described in this section may further comprise contacting an eluting solution with the sorbent material following step c), said eluting solution being capable of reversing the binding of the target species to the sorbent, whereby the target species passes into the eluting solution. The eluting solution of may release the target species of formula $[Z^2O_4]^-$ or $X^{3+}$ from the ionic interactions with charged aminoalkyl groups on the sorbent material. Releasing the target species may comprise an ion-exchange reaction between the target species of formula $[Z^2O_4]^-$ or $X^{3+}$ and one or more anions comprising the eluting solution. These anions may be, for example, chloride, iodide, bromide, acetate, nitrate, sulfate or carbonate anions. Advantageously, the volume of eluting solution required to release the target species of formula $[Z^2O_4]^-$ or $X^{3+}$ from the ionic interactions with charged aminoalkyl groups on the sorbent material may be lower than the volume of the solution used in step a).

The eluting solution may comprise a saline solution, e.g., a saline solution as described for the eluting solution of step d') in the section entitled 'Purification and concentration "catch and release" (I)' above. As described in the section entitled 'Purification and concentration "catch and release" (I)', the eluting solution, in particular the salt, may be chosen such that the characteristics of the solution enable it to reverse the binding of the target species to the sorbent material. For example, the salt may be chosen for the charge density of its constituent ions. Advantageously, the concentration of the chosen salt in the eluting solution may also be adjusted to reverse the binding of the target species to the sorbent material, in particular, to minimise the volume of eluting solution required to reverse the binding of the target species. The eluting solution may also have a defined pH, e.g., a pH as described for the pH of the eluting solution of step d') in the section entitled 'Purification and concentration "catch and release" (I)' above. The eluting solution may alternatively comprise a soluble base, e.g., a soluble hydroxide salt as described in the section entitled 'Purification "catch without release"'.

The purification and/or concentration method described in this section may yet further comprise collecting the eluting solution comprising the target species in a receptacle. The receptacle may be separate to the receptacle containing the eluate of step c). The purification and concentration "catch and release" process may thus purify the provided solution by binding the target ions reversibly and allowing the contaminant species to pass through the sorbent into the eluent, and then recovering and/or concentrating the target species as described in the section entitled 'Purification and concentration "catch and release" (I)'.

A non-limiting example of a purification and concentration ("catch and release") (II) process setup comprising a regeneration step is given in FIG. 13. In FIG. 13, a normal saline eluent (A) is provided to a generator column (K) comprising a functionalised silica sorbent as described in the section entitled 'Purification "catch without release"'. The eluate of this generator column, which is the solution of step a) in the method described in this section, is then passed through a salt and/or chloride-removing column (K2) and then passed in-line through a purification column (K3) that comprises a sorbent material as described in this section, which traps target species as described above. The waste/contaminant species eluent (EF-A) passed through the column (K3) is collected in a receptacle (W). The target species is then eluted from the column (K3) using a small volume of sterile saline solution (B), and the eluate (EF-B) collected in a receptacle as a purified and concentrated solution of target species (F).

The methods outlined in the sections entitled 'Purification "catch without release"', 'Purification and concentration "catch and release" (I)' and/or 'Purification and concentration "catch and release" (II)' may be used as described above, or may be combined with the methods as described in the section below entitled 'Generator'.

Radionuclide Generator (Radiochemical Separation of Daughter Nuclides from a Mixture of Daughter and Parent Nuclides)

The method described in the section entitled 'Purification and/or concentration methods' comprising:
a) providing a solution comprising one or more contaminant species and one or more target species;
b) contacting the solution of step a) with a sorbent material comprising porous silica having a plurality of oligomeric chains on a surface thereof, said oligomeric chains having a backbone consisting of alternating oxygen and tetravalent M atoms, wherein each of said chains comprises a plurality of M-OH moieties, and wherein each M is independently selected from the group consisting of Si, Zr, Ti, Hf, Sn, Th, Pb, and Ge; and,
c) separating the solution from the sorbent material as an eluate following step b), and the embodiments thereof discussed in the three preceding sections entitled 'Purification "catch without release"', 'Purification and concentration "catch and release" (I)' and 'Purification and concentration "catch and release" (II)' may further comprise the following steps A) to C) prior to step a):
A) providing a solution comprising one or more target species and one or more contaminant species;
B) contacting the solution of step A) with a sorbent material comprising porous silica having a plurality of oligomeric chains on a surface thereof, said oligomeric chains having a backbone consisting of alternating oxygen and tetravalent M atoms, and wherein each of said chains comprises a plurality of M-OH moieties;
wherein the oligomeric chains of the sorbent material comprise at least one M that is not Si; and, wherein the affinity of the sorbent material for the target species is lower than that for the contaminant species;
C) extracting the sorbent material from step B) with an extracting solution so as to produce an extract, said extracting solution being capable of extracting the target species from the sorbent material and said extract being the solution of step a).

The target species and the contaminant species of step A) may be as described above in the section entitled 'Target and contaminant species' for target species and contaminant species of step a). For example, in step A) above, the contaminant species may be a $D^{4+}$ ion, where D may be selected from the group consisting of Ti, Ge, Zr, Sn and Hf. The contaminant species may be, for example, $Ti^{4+}$, $Ge^{4+}$, $Zr^{4+}$, $Sn^{4+}$ or $Hf^{4+}$. In step A) above, the target species may be an $X^{3+}$ ion, where X may be selected from the group consisting of Sc, Ga, Y, In or Lu. The target species may be, for example, $Sc^{3+}$, $Ga^{3+}$, $Y^{3+}$, $In^{3+}$ or $Lu^{3+}$. D may be radioactive, e.g. $^{44}Ti$, $^{68}Ge$, $^{89}Zr$, $^{110}Sn$, $^{113}Sn$ or $^{172}Hf$, or X may be radioactive, e.g., $^{44}Sc$, $^{68}Ga$, $^{89m}Y$, $^{110m}In$, $^{113m}In$ or $^{172}Lu$, or both D and X may be radioactive. When X is $^{44}Sc$, D may be $^{44}Ti$. When X is $^{68}Ga$, D may be $^{68}Ge$. When X is $^{89m}Y$, D may be $^{89}Zr$. When X is $^{110m}In$, D may be $^{110}Sn$. When X is $^{113m}In$, D may be $^{113}Sn$. When X is $^{172}Lu$, D may be $^{172}Hf$. The $X^{3+}$ and $D^{4+}$ ions may be hydrated and/or hydroxylated in aqueous solution and therefore may be in the form $[X(OH)_{3-y}]^{y+}$ where $0 \leq y \leq 3$, or may be in the form $[D(OH)_{4-w}]^{w+}$ where $0 \leq w \leq 4$.

In step A) above, the solution comprising one or more contaminant species may comprise a contaminant species of formula $[Z^1O_4]^{2-}$ where $Z^1$ may be Mo or may be W, e.g., the contaminant species may be $MoO_4^{2-}$ or may be $WO_4^{2-}$, and/or may comprise a target species of formula $[Z^2O_4]^-$ where $Z^2$ may be Tc or Re, e.g., the target species may be $[TcO_4]^-$ or may be $[ReO_4]^-$. $Z^1$ may be radioactive, e.g., $^{99}Mo$, or $^{188}W$ or $Z^2$ may be radioactive, e.g., $^{99m}Tc$, or $^{188}Re$, or both $Z^1$ and $Z^2$ may be radioactive. Therefore, in step A), the contaminant species may be $[^{99}MoO_4]^{2-}$ or may be $[^{188}WO_4]^{2-}$ and the target species may be $[^{99m}TcO_4]^-$ or may be $[^{188}ReO_4]^-$, e.g., when the contaminant species is $[^{99}MoO_4]^{2-}$, the target species may be $[^{99m}TcO_4]^-$, or when the contaminant species is $[^{188}WO_4]^{2-}$, the target species may be $[^{188}ReO_4]^-$. The solution of step A) may comprise a parent species that decays over time to form the target species, whereby the parent species is the contaminant species. For example, the parent species may be $[^{99}MoO_4]^{2-}$ and the daughter species may be $[^{99m}TcO_4]^-$, or the parent species may be $^{188}WO_4^{2-}$ and the daughter species may be $[^{188}ReO_4]^-$.

The provided solution of step A) comprising or more contaminant species and one or more target species may be the solution obtained from, for example, the fission reaction of uranium-235 irradiated in a nuclear reactor, or the solution obtained from a neutron capture nuclear reaction using molybdenum-98. Therefore, the solution of step A) may comprise the parent or contaminant species, varying amounts of daughter or target species depending on the half-life of the parent and the period of time lapsing between irradiation and delivery to the generator, and may also comprise other species, including counter-ions, non-irradiated starting material, or other trace products.

The sorbent material of step B) may be as described for the sorbent material of step b) in the section entitled "purification "catch without release"', for example, it may be capable of retaining and/or covalently binding certain contaminant species, e.g., $[Z^1O_4]^{2-}$ ions including molybdate ($[MoO_4]^{2-}$) and/or tungstate ($[WO_4]^{2-}$) ions or $D^{4+}$ ions including $Ti^{4+}$, $Ge^{4+}$, $Zr^{4+}$, $Sn^{4+}$ or $Hf^{4+}$ or hydroxo-complexes thereof. The sorbent material in this section advantageously provides a plurality of M-OH sites to which contaminant ions may bind irreversibly, which may in turn assist in the retention of parent (contaminant) ions on the sorbent material for a period of time, during which time the parent ions may decay to produce daughter (target) ions that, once produced, do not bind or substantially do not bind to the sorbent material.

The irreversible binding in this section may comprise formation of at least one M-O—$Z^1$ or M-O-D linkage, wherein M is either Si, Zr, Ti, Hf, Sn, Th, Pb, or Ge, e.g., M is Zr or Ti. It may comprise formation of at least two M-O—$Z^1$ or M-O-D linkages per M or per $Z^1$ or D. It may comprise the formation of a bis-μ-oxo bridge between the M and $Z^1$ or D metal centres. The term 'irreversible binding' may encompass covalent binding of the $[Z^1O_4]^{2-}$ or $D^{4+}$ ions to the M-OH moieties or $MO_4$ units in the oligomeric chains covalently coupled to the surface of the porous silica substrate. The 'irreversible binding' may prevent the $[Z^1O_4]^{2-}$ or $D^{4+}$ ions from being re-solubilised. The 'irreversible binding' may prevent the $[Z^1O_4]^{2-}$ or $D^{4+}$ ions from being re-solubilised under the normal conditions of use of the porous silica sorbent material. The $[Z^1O_4]^{2-}$ or $D^{4+}$ ions may compete with the $[Z^2O_4]^-$ or $X^{3+}$ target ions for irreversible binding sites such that no, or substantially no, target species bind irreversibly to the sorbent material.

The sorbent material used in step B) is advantageously devoid of aminoalkyl functional groups. The porous silica sorbent devoid of aminoalkyl functional groups may be used in step B) of the method to capture the contaminant ions. In this method, step B) may be capture up to 100% by mole or mass of the $[Z^1O_4]^{2-}$ or $D^{4+}$ ions from the provided solution. The contacting of step B) may capture between 100 and 50% by mole or mass of the $[Z^1O_4]^{2-}$ or $D^{4+}$ ions from the provided solution, or may capture between 100 and 95, 100 and 85, 95 and 85, 90 and 60, or 85 and 500% by mole or mass of the $[Z^1O_4]^{2-}$ or $D^{4+}$ ions from the provided solution, e.g., 100, 99, 98, 97, 96, 95, 94, 93, 92, 91, 90, 85, 80, 75, 70, 65, 60, 55 or 50% by mole or mass of the $[Z^1O_4]^{2-}$ or $D^{4+}$ ions from the provided solution.

Once the parent or contaminant ions have been captured as described above in step B), step C) may comprise extracting the sorbent material from step B) with an extracting solution so as to produce an extract, said extracting solution being capable of extracting the target species from the sorbent material and said extract being the solution of step a).

The extracting solution of step C) may advantageously extract the target or daughter species formed by the decay of the parent species from the sorbent material by allowing the target species to pass into the extract. The extract may then be provided as the solution of step a). The extracting solution in step C) may extract up to 100% by mole or mass of the target species of formula $[Z^2O_4]^-$ present in the sorbent material at the time of extracting, or may extract between about 100 and 85%, or between about 100 and 95, 100 and 90, 95 and 85 or 90 and 85% by mole or mass of the target species of formula $[Z^2O_4]^-$ or $X^{3+}$ present in the sorbent material at the time of extracting, e.g., 100, 99, 98, 97, 96, 95, 94, 93, 92, 91, 90, 89, 88, 87, 86 or 85% by mole or mass of the target species of formula $[Z^2O_4]^-$ or $X^{3+}$ present in the sorbent material at the time of extracting. The extract thus produced in step C) may comprise the target species and trace amounts of contaminant $[Z^1O_4]^{2-}$ or $D^{4+}$ ions, e.g., between about 5 ppm and 0.001 ppm $[Z^1O_4]^{2-}$ or $D^{4+}$, or between about 5 ppm and about 1 ppm, or 1 and 0.1 ppm, or 0.1 and 0.01 ppm, or 0.01 and 0.001 ppm, or less than about 5 ppm, 1 ppm, 0.5 ppm, 0.1 ppm, 0.05 ppm, 0.01 ppm, 0.005 ppm, or 0.001 ppm, e.g., about 5 ppm, 0.5 ppm, 0.1 ppm, 0.05 ppm, 0.01 ppm, 0.005 ppm, or 0.001 ppm or optionally less than about 0.001% radioactivity of target and/or contaminant species in the eluate per total radioactivity of target and/or contaminant species on the sorbent column.

The extracting solution of step C) may comprise a saline solution, for example, it may be as described for the eluting solution of step b) in the section entitled 'Purification and concentration "catch and release" (I)', e.g., it may comprise ammonium or another group I or II chloride, e.g., potassium chloride, or any water soluble ammonium or group I or II sulfate, carbonate, chloride, acetate, sulfate, chloride, nitrate, iodide or bromide salt. The total salt concentration may be any suitable concentration, e.g., it may be about 0.1 M, or between about 0.01 and about 1 M, or between about 0.01 and about 0.1, 0.1 and 1, 0.05 and 0.5, or 0.5 and 1, e.g., 0.01, 0.05, 0.1, 0.2, 0.3, 0.4, 0.5, 0.6, 0.7, 0.8, 0.9 or 1 M, or between about 1 M and about 10 M, or between about 0.1 and 8 M, 0.1 and 1 M, 1 and 6 M, 4 and 10 M, or 4 and 6 M, e.g., about 1, 2, 3, 4, 5, 6, 7, 8, 9, or 10 M. For example, the eluting solution may comprise sodium chloride, wherein the sodium chloride concentration is about 1% (w/v) and the pH is between about pH 1 and about pH 5, or may comprise sodium or ammonium sulfate, wherein the total sodium or ammonium sulfate concentration is between about 0.01 and about 0.5 M, or may comprise sodium or ammonium acetate, wherein the sodium or ammonium acetate concentration is between about 0.1 and about 1.0 M and the pH is between about pH 2 and about pH 4. The extracting solution of step C) may comprise any suitable mineral acid, e.g., hydrochloric acid, sulfuric acid, or nitric acid. The acid may have a concentration of between about 0.01 M and about 1.0 M, e.g., between about 0.01 and 0.1 M, 0.05 and 0.5 M, or 0.5 and 1.0 M, e.g., about 0.01, 0.05, 0.1, 0.5, or 1.0 M.

The generator process described above may be performed prior to the purification method described in the section entitled 'Purification "catch without release"', or may be performed prior to the purification and concentration methods described in the sections entitled 'Purification and concentration "catch and release" (I)' and 'Purification and concentration "catch and release" (II)'. Where the generator process described above is performed prior to the purification and concentration methods described in the section entitled 'Purification and concentration "catch and release" (I)', the eluate collected in step c) comprising substantially no target species and substantially no contaminant species may be used as the extracting solution in step C) of the above method. Thus, the eluate collected in step c) in the section entitled 'Purification and concentration "catch and release" (I)' may be recycled for use in step C) of the above method. The recycling process may be performed more than 1 time, e.g., more than 2, 5, 10, 20, 50, 100 or 150 times, e.g., between 1 and 150 times, or between 1 and 50, 50 and 100, or 100 and 150 times, e.g., 1, 2, 3, 4, 5, 10, 15, 20, 30, 40, 50, 80, 100, 120, or 150 times.

Advantageously, the adsorption capacity of the sorbent material for the contaminant or parent ions as used in the generator method described in this section is high, for example, between about 400 and 1000 mg Mo/g sorbent or between about 700 and 2000 mg W/g sorbent, or adsorption capacities as described in the section entitled 'Sorbent material'. This high adsorption capacity may be due to a high density of M-OH moieties on the inner and/or outer surface of the sorbent, which may irreversibly bind contaminant or parent species. The high adsorption capacity of the sorbent material for the contaminant or parent ions may be achieved by synthesising sorbent materials with a particularly high content of tetravalent M atoms, for example, where M is Ti or Zr.

Summary of the Use of Sorbents for Radiochemical Separation Processes

The present invention provides for the use of any suitable sorbent material described herein for concentrating a target species from a solution comprising one or more contaminant species and the target species. The present invention also provides for the use of any suitable sorbent material described herein for separating a target species from a contaminant species from a solution comprising one or more contaminant species and one or more target species. The contaminant species may be a parent species that decays over time to form the target species. For example, the contaminant species may be of formula $[Z^1O_4]^{2-}$ and the target species may be of formula $[Z^2O_4]^-$, wherein $Z^1$=Mo or W and $Z^2$=Tc or Re. Alternatively or additionally, the contaminant species may be a $D^{4+}$ ion, wherein D is selected from the group consisting of Ti, Ge, Zr, Sn and Hf and the target species may be an $X^{3+}$ ion, wherein X is selected from the group consisting of Sc, Ga, Y, In or Lu. The present invention provides for the use of any suitable sorbent material described herein in a radioisotope concentrator device. The radioisotope concentrator device may separate and/or concentrate a target species from a solution comprising one or more contaminant species and one or more target species. For example, the radioisotope concentrator device may be an ULTRALUTE® device (multi-use radioisotope concentrator).

Summary of Purification and/or Concentration Methods

As described in the above sections, the sorbent materials of the present invention may be selected for purification and/or concentration methods based on either the capability for covalent bonding/chemisorption (i.e., "catch without release") or capability for ion-exchange (i.e., "catch and release"), or a combination of both capabilities within the same sorbent material. The wide ranging $pK_a$ values of the hydroxyl groups of metal hydrous oxides (e.g., $pK_a$=4.2 for hydrous titanium oxide and $pK_a$=6-8 for hydrous zirconium oxide) and of the amino groups ($pK_a$=9.7-11.2) on the oligomeric chains coated on the solid silica support provides scope for high separation resolution in purification and/or concentration methods described herein when solutions of specific pH are chosen. Further, the multifunctional nature of the sorbent materials of the present invention makes them suitable for use in $^{99m}$Tc/$^{99}$Mo and $^{188}$Re/$^{188}$W generators as generator column packing materials, where they may act both to purify and concentrate generator eluate, as well as in further separation and/or concentration processes.

It will be appreciated by persons of ordinary skill in the art that numerous variations and/or modifications can be made to the present invention as disclosed in the specific embodiments without departing from the spirit or scope of the present invention as broadly described. The present embodiments and the detailed description are, therefore, to be considered in all respects as illustrative and not restrictive.

EXAMPLES

The present invention will now be described with reference to specific examples, which should not be construed as in any way limiting.

Performance of Sorbent: Synthesis

Large surface area and high porosity silica gel suitable for use in the present invention may be synthesised as follows: In a first step, potassium permanganate is reduced with ethyl alcohol in aqueous solution at room temperature to form a hydrated manganese dioxide sol. This hydrated manganese dioxide sol is then added to an acidic and/or a pH buffer controlled solution containing sodium silicate, resulting in a hydrogel precipitate. The hydrogel precipitate is then aged and hydrothermally treated in a sealed Teflon bottle at increasing temperatures of between 70 and 110° C. under autogenous pressure for several hours until a semicrystalline product is formed. The precipitate is then dried at 60° C. for several hours and ground into powder with a particle size of less than 100 μm. The obtained powder is then washed with 1 M oxalic acid solution until all the manganese dioxide has been converted into soluble $Mn^{2+}$ ions, resulting in a white solid powder. The soluble small $Mn^{2+}$ ions are not adsorbed by silica gel and are therefore easily washed out from the solid gel powder together with $K^+$, $Na^+$ and nitrate ions. The white powder is then washed with deionised water to afford silica free of $Mn^{2+}$, $K^+$, $Na^+$, nitrate and other counter-ions. Finally, the white powder is washed with ethyl alcohol to remove any organic residues generated from the oxidation of oxalic acid. The solid gel is then dried in an oven at 135° C. for several hours and sieved to receive the solid hydrous silica powder of suitable particle size (e.g. 50 to 100 μm). This silica gel powder is then used as a starting material in the following methods.

Figure 2:
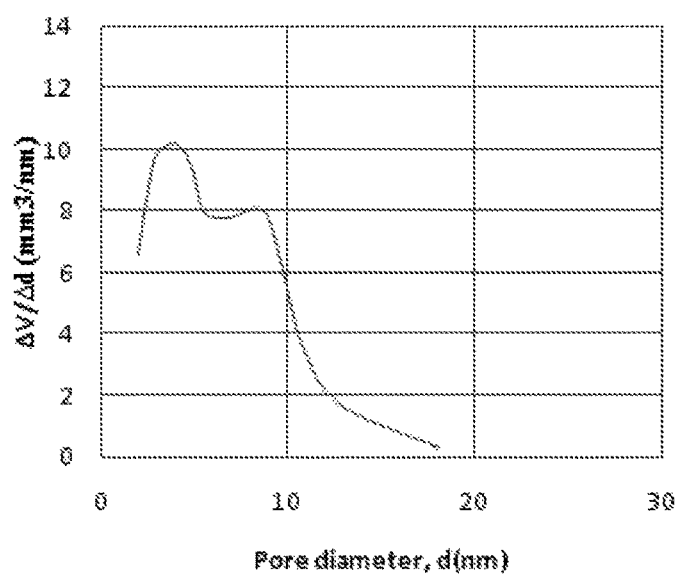
FIG. 2 shows a pore size distribution of silica synthesised using the $MnO_2$-template method.
Figure 3:
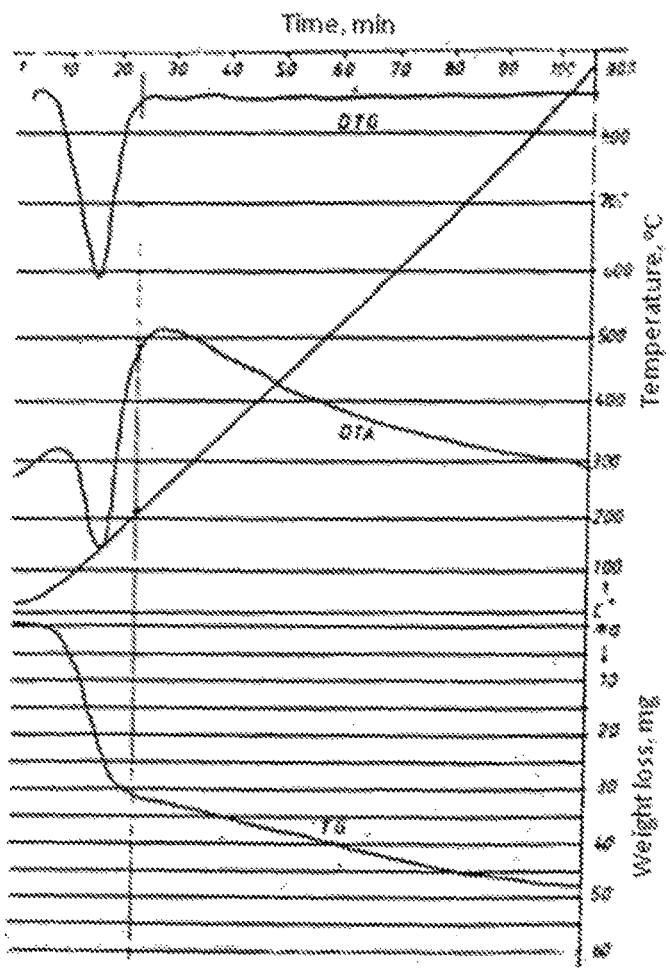
FIG. 3 shows thermoanalysis diagrams of silica synthesised using the $MnO_2$-template method.

Solution parameters for the performing the synthesis of the $MnO_2$ nanoparticle-templated silica above are given in Table 1. A scanning electron microscope image of the silica synthesised by the $MnO_2$-templated method is shown in FIG. 1. The pore distribution of the silica synthesised by the $MnO_2$-templated method is shown in FIG. 2. Thermoanalysis diagrams for silica synthesised using the $MnO_2$-template method are shown in FIG. 3.

TABLE 1

Solution parameters for the performing the synthesis of the $MnO_2$ nanoparticle-templated silica

| Solutions | Parameters | Higher porosity silica | Medium porosity silica | Lower porosity silica |
|---|---|---|---|---|
| Solution A: Silicate sol solution | Volume, $V_{Silicate}$, mL | 0.50 | 1.00 | 1.00 |
| | $SiO_2$ concentration, $C_{SiO2}$, mg/mL | 350.00 | 368.35 | 368.35 |
| | $SiO_2$ content, mg | 175.00 | 368.35 | 368.35 |
| | Base concentration, $C_{NaOH}$, M | 3.50 | 4.75 | 4.75 |
| Solution B: $MnO_2$ sol solution | Volume, $V_{MnO2}$, mL | 3.00 | 3.00 | 3.00 |
| | $MnO_2$ concentration $C_{MnO2}$, mg/mL | 14.20 | 21.30 | 14.20 |
| | $MnO_2$ content, mg | 42.60 | 63.93 | 42.60 |
| | Acid concentration, $C_{HNO3}$, M | 0.25 | 0.25 | 0.25 |

TABLE 1-continued

Solution parameters for the performing the synthesis of the $MnO_2$ nanoparticle-templated silica

| Solutions | Parameters | Higher porosity silica | Medium porosity silica | Lower porosity silica |
|---|---|---|---|---|
| Mixed solution, | Base concentration $C_{NaOH}$, M | 0.285 | 1.00 | 1.00 |
| Solution A + Solution B | $SiO_2$ concentration $C_{SiO2}$, mg/mL | 50.00 | 92.08 | 92.08 |
| Solution C: Acetate buffer solution | Volume of 12M acetic acid solution, mL | 1.50 | 2.50 | 2.50 |
|  | Volume of 1.0M sodium acetate, mL | 1.50 | 2.50 | 2.50 |
| Gelation solution mixture, | Volume, mL | 6.50 | 9.00 | 9.00 |
|  | $SiO_2$ concentration $C_{SiO2}$, mg/mL | 26.92 | 40.92 | 40.92 |
| Solution A + Solution B + Solution C | pH | ~5 | ~5 | ~5 |
|  | Gelation time, min | 7-10 | 4-6 | 4-6 |
|  | (Mn/Si) mol ratio, mol % | 16.8 | 12.00 | 8.00 |

Method 1: Silicon Oxide Mediated Covalent Coupling ($SiO_4$-MCC) Method

In the first step, silanol groups on the surface of the silica gel are reacted with silicon alkoxide in toluene solvent in a condensation reaction. This reaction is followed by the hydrolysis of the residual alkoxy groups of silicon-alkoxide with a defined amount of water to form silanol groups. Then, the silanol groups formed are reacted with either an aminoalkyl silane compound, with one or more tetravalent metal alkoxides, or with a mixture of aminoalkyl silane/s and one or more tetravalent metal alkoxides in a further condensation reaction. The final sorbent material product is then obtained after washing and drying at controlled temperature.

Example 1: Synthesis Using Method 1

As an example of the above described $SiO_4$-MCC process, tetraethylorthosilicate (TEOS)-mediated covalent coupling (TEOS-MCC) is performed as follows: 10 g silica gel powder synthesised above (S=703 $m^2$/g, C=2.82 mmol OH/g) is suspended in 75 mL toluene in a glass reactor equipped with a reflux condenser capped with a desiccator-vent plug. The reaction is kept under a dry nitrogen atmosphere during processing/reflux and the required amount of TEOS (28.0 mmol) is added. The reaction mixture is then stirred under reflux at 70° C. for several hours (minimum 48 hours) under a dry nitrogen atmosphere. In the following step, the required amount of water dissolved in ethanol (84.0 mmol water in 5 mL dried ethanol) is added whilst stirring, and then the mixture is stirred for a further 10 hours. The required amount of aminoalkyl silane compound (42 mmol [3-(diethylamino)propyl]trimethoxysilane/$(C_2H_5)_2N(CH_2)_3Si(OCH_3)_3$, dissolved in 20 mL toluene) is then added, followed by the addition of the required amount of a tetravalent metal alkoxide (42 mmol titanium ethoxide/Ti$(OC_2H_5)_4$ dissolved in 20 mL toluene) or a mixture thereof dissolved in 40 mL toluene. During addition, and for 48 hours thereafter, the mixture is stirred under reflux. The solid powder of the reaction mixture is then filtered and washed, first with toluene and then with ethanol and followed by water. The final sorbent material product is obtained after drying the solid powder at 75° C. for 24 hours. The [3-(diethylamino)propyl]hydroxyl silane/titanium-hydroxyl-functionalized silica sorbent produced by this method contained 99.4 mg Ti/g sorbent material and 28.5 mg Ni/g sorbent material.

Method 2: Self-Mediated Covalent Coupling (S-MCC) Using an Aminoalkyl Silane Mediator In the first step, silanol groups on the surface of silica gel are reacted with an aminoalkyl silane compound in toluene solvent in a condensation reaction. This reaction is followed by the hydrolysis of the residual alkoxide groups of amino silane compound with a defined amount of water to form silanol groups. Then, the silanol groups formed are reacted with either an aminoalkyl silane compound, one or more tetravalent metal alkoxides, or a mixture of aminoalkyl silane/s and one or more tetravalent metal alkoxides in a further condensation reaction. The final sorbent material product is then obtained after washing and drying at controlled temperature.

Example 2: Synthesis Using Method 2

As an example of the above described S-MCC process, 10 g silica gel powder synthesised above (S=703 $m^2$/g, C=2.82 mmol OH/g) is suspended in 75 mL toluene in a glass reactor equipped with a reflux condenser capped with a desiccator-vent plug. The reaction is kept under a dry nitrogen atmosphere during processing/refluxing and the required amount of aminoalkyl silane (28.0 mmol [3-(diethylamino)propyl]trimethoxysilane/$(C_2H_5)_2N(CH_2)_3Si(OCH_3)_3$, dissolved in 20 mL toluene) compound or 28.0 mmol of a mixture of aminoalkyl silane and metal alkoxide compound dissolved in toluene or alcohol is added. The reaction mixture is stirred under reflux at 70° C. for several hours (minimum 48 hours) under a dry nitrogen atmosphere. In the following step, the required amount of water dissolved in ethanol (56.0 mmol water in 5 mL dried ethanol) is added whilst stirring, and then the mixture is stirred for a further 10 hours. The required amount of aminoalkyl silane compound (56 mmol [3-(diethylamino)propyl]trimethoxysilane/$(C_2H_5)_2N(CH_2)_3Si(OCH_3)_3$, dissolved in 30 mL toluene) is then added under a dried nitrogen atmosphere. During addition, and for 48 hours thereafter, the mixture is stirred under reflux. The solid powder of the reaction mixture is then filtered and washed, first with toluene and then with ethanol and followed by water. The final sorbent material product is obtained after drying the solid powder at 75° C. for 24 hours. The [3-(diethylamino)propyl]hydroxyl silane-functionalised silica sorbent material synthesised by this method contained 46.5 mg N/g sorbent material.

Method 3: Self-Mediated Covalent Coupling (S-MCC) Using a Metal Oxide Mediator

In the first step, silanol groups on the surface of silica gel are reacted with a tetravalent metal alkoxide compound in toluene solvent in a condensation reaction. This reaction is followed by the hydrolysis of residual alkoxy groups of metal alkoxide compound with a defined amount of water to form the hydroxyl groups. Then, the metal hydroxyl groups formed are reacted with an aminoalkyl silane compound, one or more tetravalent metal alkoxides, or a mixture of aminoalkyl silane/s and one or more tetravalent metal alkoxides in a further condensation reaction. The final sorbent material product is then obtained after washing and drying at controlled temperature.

Example 3: Synthesis Using Method 3

As an example of the above described metal oxide mediated covalent coupling process, 10 g silica gel powder as synthesised above (S=703 m$^2$/g, C=2.82 mmol OH/g) is suspended in 75 mL toluene (alcohol for ZrOH coating) in a glass reactor equipped with a reflux condenser capped with a desiccator-vent plug. The reaction is kept under a dry nitrogen atmosphere during processing/refluxing. The required amount of a tetravalent metal alkoxide (28 mmol titanium ethoxide/Ti(OC$_2$H$_5$)$_4$ dissolved in 20 mL toluene; or 28 mmol zirconium tetrachloride/Zr(Cl)$_4$ or zirconium ethoxide/Zr(OC$_2$H$_5$)$_4$ dissolved in 20 mL isopropyl alcohol) is then added. The reaction mixture is stirred under reflux at 70° C. for several hours (minimum 48 hours) under a dry nitrogen atmosphere. In the following step, the required amount of water dissolved in ethanol (84.0 mmol water in 5 mL dried ethanol) is added whilst stirring, and then the mixture is stirred for a further 10 hours. The required amount of (84 mmol titanium ethoxide/Ti(OC$_2$H$_5$)$_4$ dissolved in 40 mL toluene or 84 mmol zirconium tetrachloride/Zr(Cl)$_4$ or zirconium ethoxide/Zr(OC$_2$H$_5$)$_4$ dissolved in 40 mL isopropyl alcohol) is then added under a dried nitrogen atmosphere. During addition, and for 48 hours thereafter, the mixture is stirred under reflux. The solid powder of the reaction mixture is then filtered and washed, first with toluene and then with ethanol and followed by water. The final sorbent material product is obtained after drying the solid powder at 75° C. for 24 hours. The tetravalent metal hydroxyl-functionalised silica sorbent material product contained 386.2 mg Zr/g sorbent material.

Summary of Methods

Possible combinations of mediator and functional groups according to synthetic methods 1 to 3 above are shown in Table 2.

TABLE 2

Possible combinations of mediator and functional group according to synthetic methods 1 to 3 above.

| Synthetic Method | Mediated by | Attached EO$_4$ | Assigned as | Combination** | Coupling Option* |
|---|---|---|---|---|---|
| 2 | Silane* | Silane | Silane*—Silane | 1 | A |
|   |   | SiO$_4$ | Not investigated | 2 | — |
|   |   | TiO$_4$ | Silane*—TiO | 3 | B |
|   |   | ZrO$_4$ | Silane*—ZrO | 4 | B |
| 1 | SiO$_4$* | SiO$_4$ | Not investigated | 5 | — |
|   |   | Silane | SiO$_4$*—Silane | 6 | D |
|   |   | TiO$_4$ | SiO$_4$*—TiO | 7a | F |
|   |   | TiO$_4$; Silane | SiO$_4$*(Silane)—TiO | 7b | E |
|   |   | ZrO$_4$ | SiO$_4$*—ZrO | 8a | F |
|   |   | ZrO$_4$; Silane | SiO$_4$*(Silane)—ZrO | 8b | E |
| 3 | TiO$_4$* | TiO4 | TiO$_4$*—TiO | 9a | C |
|   |   | TiO$_4$; Silane | TiO$_4$*(Silane)—TiO | 9b | M |
|   |   | Silane | TiO$_4$*—Silane | 10a | G |
|   |   | Silane; TiO$_4$ | TiO$_4$*(TiO$_4$)—Silane | 10b | H |
|   |   | SiO$_4$ | Not investigated | 11 | — |
|   |   | ZrO$_4$ | TiO$_4$*—ZrO | 12a | C |
|   |   | ZrO$_4$; Silane | TiO$_4$*(Silane)—ZrO | 12b | M |
| 3 | ZrO$_4$* | ZrO | ZrO$_4$*—ZrO | 13a | C |
|   |   | ZrO$_4$; Silane | ZrO$_4$*(Silane)—ZrO | 13b | M |
|   |   | Silane | ZrO$_4$*—Silane | 14a | G |
|   |   | Silane; ZrO$_4$ | ZrO$_4$*(ZrO$_4$)—Silane | 14b | H |
|   |   | SiO$_4$ | Not investigated | 15 | — |
|   |   | TiO$_4$ | ZrO$_4$*—TiO | 16a | C |
|   |   | TiO$_4$; Silane | ZrO$_4$*(Silane)—TiO | 16b | M |

Figure 7:
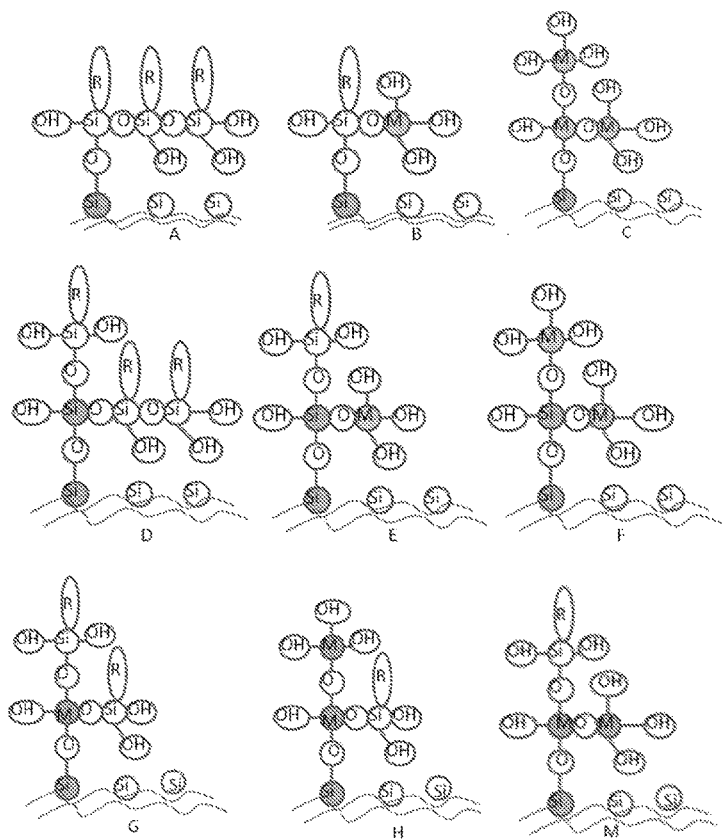
FIG. 7 is a diagram showing coupling options A, B, C, D, E, F, G, H and M. These are porous silica sorbent materials made according to the following Methods and corresponding to the following Combinations (also see Table 2):
A—Method 2, Combination 1
B—Method 2, Combination 3 or 4
C—Method 3, Combination 9, 12, 13, or 16
D—Method 1, Combination 6
E—Method 1, Combination 7 or 8 ($SiO_4$ (aminoalkyl silane+$MO_4$))
F—Method 1, Combination 7 or 8
G—Method 3, Combination 10 or 14 ($MO_4(MO_4)$)+aminoalkyl silane)
H—Method 3, Combination ($MO_4$+$MO_4$/aminoalkyl silane mixture)
M—Method 3, Combination 9, 12, 13, or 16 ($MO_4$(aminoalkyl silane)+$MO_4$)

*These coupling options are illustrated in FIG. 7.
**These combination designations are referenced in Tables 5 and 6, Calculations As the present invention relates to coupling certain functional groups to the surface of a porous silica substrate, optimising the density of OH groups on the silica surface is used, in turn, to optimise the density of functional groups on the silica surface. Performing this optimisation may lead to sorbent materials with an enhanced capacity to effect purification and concentration.

Figure 4:
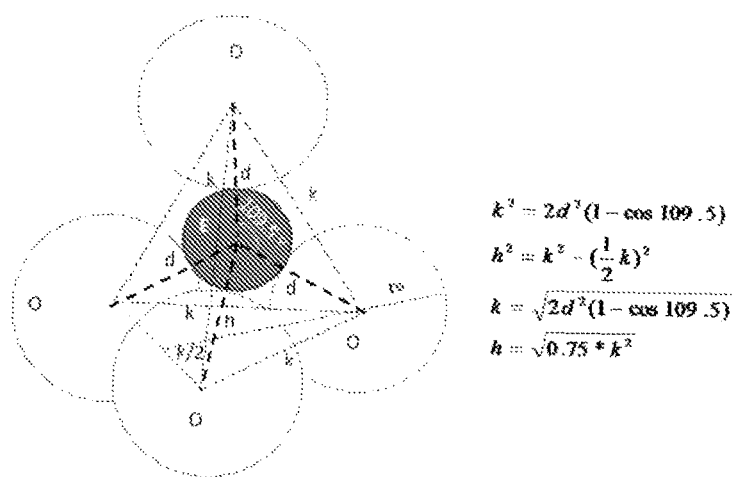
FIG. 4 is a diagram of the tetrahedral unit used to model tetravalent metal alkoxy and aminoalkyl silane groups in geometric compatibility calculations. Both units are represented by the tetrahedral $EO_4$ unit.

To assess the geometric compatibility of metal alkoxy and aminoalkylsilano groups, it has been assumed that these groups exist in tetrahedral units (EO$_4$). Further, the following calculations are based on the calculation of the maximum numbers of covalently bonded tetrahedral units (EO$_4$) able to be accommodated in a defined area of the silica surface. The tetrahedral unit used to model the tetravalent metal alkoxy and aminoalkylsilano groups is shown in FIG. 4.

The radii of the ions used for the further calculations are shown in Table 3.

TABLE 3

Radii of the ions used for geometric compatibility calculations

| Ion | $C^{4-}$ | $Si^{4-}$ | $Ti^{4-}$ | $Zr^{4-}$ | $O^{2-}$ | $OH^-$ | $H_2O$ | $Cl^-$ | $TcO_4^-$ $ReO_4^-$ | $MoO_4^{2-}$ | $WO_4^{2-}$ |
|---|---|---|---|---|---|---|---|---|---|---|---|
| Radius, Å | 0.16 | 0.41 | 0.61 | 0.72 | 1.32 | 1.37 | 1.50 | 1.81 | 3.2 | 3.23 | 3.24 |

The parameters shown in Table 3 were combined with the geometric calculations in FIG. 4, and parameters for d, h, and k calculated. The results are given in Table 4 for different central elements (E) of the tetrahedral units ($EO_4$).

TABLE 4

Geometric parameters d, h, and k calculated for different central elements (E) of the tetrahedral units ($EO_4$)

| Element, E | Si | Ti | Zr |
|---|---|---|---|
| Parameters | $d_{SiO} = r_O + r_{Si} = 1.73$ Å | $d_{TiO} = r_O + r_{Ti} = 1.93$ Å | $d_{ZrO} = r_O + r_{Zr} = 2.04$ Å |
|  | $h_{SiO} = 2.4470$ Å | $h_{TiO} = 2.7299$ Å | $h_{ZrO} = 2.8855$ Å |
|  | $k_{SiO} = 2.8256$ Å | $k_{TiO} = 3.1522$ Å | $k_{ZrO} = 3.3319$ Å |

As the silica gel sorbent is used as an inert substrate for the covalent coupling of functional groups on its surface, the following experimentally measured properties of the silica substrate are described for use in further calculations:

S ($m^2/g$) is the surface area of the silica;
s (Å$^2$/OH-group) is the surface area per a silanol group of the silica surface; and
C (mmol/g) is the ion exchange capacity of the silica (i.e., quantity of the silanol groups per gram of silica).

Assuming a silanol group occupies a square of area s on the silica surface, the side D and the diagonal L of this square are calculated using Equation 9 and Equation 10:

$$s = \frac{S \times 10^{20}}{C \times 10^{-3} \times 6.023 \times 10^{23}} = \frac{S}{6.023 \times C} \quad \text{Equation 9}$$

$$D = \sqrt{\frac{S}{6.023 \times C}} \; ; \; L = \sqrt{\frac{2 \times S}{6.023 \times C}} \quad \text{Equation 10}$$

Figures 5, 6:
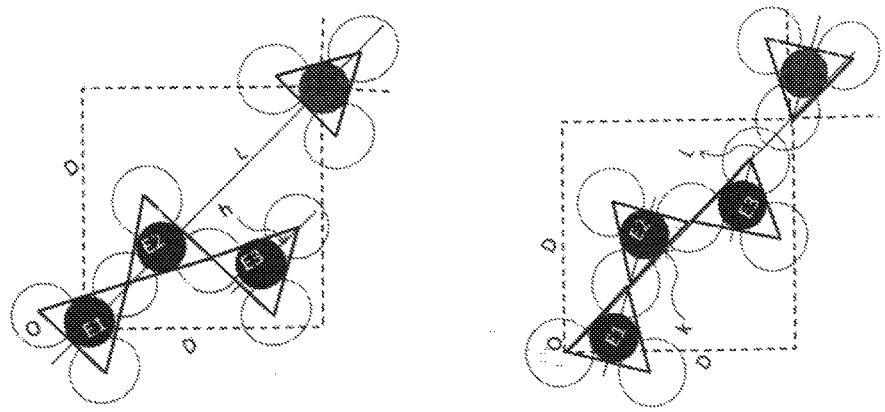
FIG. 5 shows one configuration of $EO_4$ units on the surface of the porous silica substrate used for geometric calculations (Configuration 1).
FIG. 6 shows a second configuration of $EO_4$ units on the surface of the porous silica substrate used for geometric calculations (Configuration 2).

The assessment of geometric compatibility of the metal alkoxy and silano groups for covalent coupling of functional groups on the silica surface is based on the calculation of the maximum numbers of covalently bonded tetrahedral units ($EO_4$) arranged in this square, lying along its diagonal L, as illustrated in Configuration 1 (FIG. 5) and Configuration 2 (FIG. 6).

Data for the geometric assessment of Configuration 1 is given in Table 5. Coupling options A, B, C, D, E, F, G, H and M are illustrated in FIG. 7. These coupling options refer to porous silica sorbent materials made according to the following Methods and corresponding to the following Combinations (also see Table 2):

A—Method 2, Combination 1; B—Method 2, Combination 3 or 4; C—Method 3, Combination 9, 12, 13, or 16; D—Method 1, Combination 6; E—Method 1, Combination 7 or 8 ($SiO_4$ (aminoalkylsilane)+$MO_4$); F—Method 1, Combination 7 or 8; G—Method 3, Combination 10 or 14; H—Method 3, Combination 10 or 14 ($MO_4(MO_4)$+aminoalkylsilane); M—Method 3, Combination 9, 12, 13, or 16 ($MO_4$(aminoalkylsilane)+$MO_4$).

TABLE 5

Geometric assessment of Configuration 1 (FIG. 5).

| Combination (see Table 2) | Data in Table | Coupling option* | Equations for Configuration 1 |
|---|---|---|---|
| 1 | 7 | A |  |
| 6 | 7 | D | $n_{SiO4*-Silane}(1) = \dfrac{L - r_O}{h_{SiO}} = \dfrac{\sqrt{\dfrac{2 \times S}{6.023 \times C}} - r_O}{\sqrt{2 \times d_{SiO}^2 \times (1 - \cos 109.5°) \times 0.75}}$ |

$n_{Silane*-Silane} = n_{SiO4*-Silane}$

TABLE 5-continued

Geometric assessment of Configuration 1 (FIG. 5).

| Combination (see Table 2) | Data in Table | Coupling option* | Equations for Configuration 1 |
|---|---|---|---|
| 3 | 8 | B | |
| 4 | 8 | B | |
| 7a | 9 | F | $n_{SiO4^*-TiO}(1) = \dfrac{L - (h_{SiO} + r_O)}{h_{TiO}} = \dfrac{\sqrt{\dfrac{2 \times S}{6.023 \times C}} - (h_{SiO} + r_O)}{\sqrt{2 \times d_{TiO}^2 \times (1 - \cos 109.5°) \times 0.75}}$ |
| 7b | 8 | E | |
| 8a | 9 | F | |
| 8b | 8 | E | |

$$n_{SiO4^*-ZrO}(1) = \dfrac{L - (h_{SiO} + r_O)}{h_{ZrO}} = \dfrac{\sqrt{\dfrac{2 \times S}{6.023 \times C}} - (h_{SiO} + r_O)}{\sqrt{2 \times d_{ZrO}^2 \times (1 - \cos 109.5°) \times 0.75}}$$

$n_{Silane^*-TiO} = n_{SiO4^*-TiO}$; $n_{Silane^*-ZrO} = n_{SiO4^*-ZrO}$

| | | | |
|---|---|---|---|
| 9a | 11 | C | |
| 9b | 10 | M | |
| 12a | 11 | C | $n_{SiO4^*-TiO}(1) = \dfrac{L - r_O}{h_{SiO}} = \dfrac{\sqrt{\dfrac{2 \times S}{6.023 \times C}} - r_O}{\sqrt{2 \times d_{TiO}^2 \times (1 - \cos 109.5°) \times 0.75}}$ |
| 12b | 10 | M | |
| 13a | 11 | C | |
| 13b | 10 | M | |
| 16a | 11 | C | |
| 16b | 10 | M | |

$$n_{M(TiO-SiO)}(1) = 1 + \dfrac{L - (h_{TiO} + r_O)}{h_{ZrO}} = 1 + \dfrac{\sqrt{\dfrac{2 \times S}{6.023 \times C}} - (h_{TiO} + r_O)}{\sqrt{2 \times d_{ZrO}^2 \times (1 - \cos 109.5°) \times 0.75}}$$

$$n_{ZrO4^*-ZrO}(1) = \dfrac{L - t_O}{h_{ZrO}} = \dfrac{\sqrt{\dfrac{2 \times S}{6.023 \times C}} - r_O}{\sqrt{2 \times d_{ZrO}^2 \times (1 - \cos 109.5°) \times 0.75}}$$

$$n_{M(ZrO-TiO)}(1) = 1 + \dfrac{L - (h_{ZrO} + r_O)}{h_{TiO}} = 1 + \dfrac{\sqrt{\dfrac{2 \times S}{6.023 \times C}} - (h_{ZrO} + r_O)}{\sqrt{2 \times d_{TiO}^2 \times (1 - \cos 109.5°) \times 0.75}}$$

$n_{M(TiO4-ZrO)} \approx n_{ZrO4^*-ZrO}$; $n_{M(ZrO4^*-TiO)} \approx n_{TiO4^*-TiO}$

| | | | |
|---|---|---|---|
| 10a | 12 | G | |
| 10b | 13 | H | $n_{TiO4^*-Silane}(1) = \dfrac{L - (h_{TiO} + r_O)}{h_{SiO}} = \dfrac{\sqrt{\dfrac{2 \times S}{6.023 \times C}} - (h_{TiO} + r_O)}{\sqrt{2 \times d_{SiO}^2 \times (1 - \cos 109.5°) \times 0.75}}$ |
| 14a | 12 | G | |
| 14b | 13 | H | |

$$n_{ZrO4^*-Silane}(1) = \dfrac{L - (h_{ZrO} + r_O)}{h_{SiO}} = \dfrac{\sqrt{\dfrac{2 \times S}{6.023 \times C}} - (h_{ZrO} + r_O)}{\sqrt{2 \times d_{SiO}^2 \times (1 - \cos 109.5°) \times 0.75}}$$

*These coupling options are illustrated in FIG. 7.

Data for the geometric assessment of Configuration 2 is given in Table 6.

TABLE 6

Geometric assessment of Configuration 2 (FIG. 6).

| Combination (see Table 2) | Data in Table | Coupling option* | Equations for Configuration 1 |
|---|---|---|---|
| 1 | 7 | A | |
| 6 | 7 | D | $n_{SiO4-Silane}(2) = \dfrac{L - r_O}{k_{SiO}} = \dfrac{\sqrt{\dfrac{2 \times S}{6.023 \times C}} - r_O}{\sqrt{2 \times d_{SiO}^2 \times (1 - \cos 109.5°)}}$ |

$n_{Silane^*-Silane} = n_{SiO4^*-Silane}$

TABLE 6-continued

Geometric assessment of Configuration 2 (FIG. 6).

| Combination (see Table 2) | Data in Table | Coupling option* | Equations for Configuration 1 |
|---|---|---|---|
| 3 | 8 | B | |
| 4 | 8 | B | |
| 7a | 9 | F | $n_{SiO4*-TiO}(2) = \dfrac{L-(k_{SiO}+r_O)}{k_{TiO}} = \dfrac{\sqrt{\dfrac{2\times S}{6.023\times C}} - (k_{SiO}+r_O)}{\sqrt{2\times d_{TiO}^2 \times (1-\cos 109.5°)}}$ |
| 7b | 8 | E | |
| 8a | 9 | F | |
| 8b | 8 | E | |

$$n_{SiO4*-ZrO}(2) = \dfrac{L-(k_{SiO}+r_O)}{k_{ZrO}} = \dfrac{\sqrt{\dfrac{2\times S}{6.023\times C}} - (k_{SiO}+r_O)}{\sqrt{2\times d_{ZrO}^2 \times (1-\cos 109.5°)}}$$

$$n_{Silane*-TiO} = n_{SiO4-TiO}; \; n_{Silane*-ZrO} = n_{SiO4*-ZrO}$$

| | | | |
|---|---|---|---|
| 9a | 11 | C | |
| 9b | 10 | M | |
| 12a | 11 | C | $n_{TiO4*-TiO}(2) = \dfrac{L-r_O}{k_{no}} = \dfrac{\sqrt{\dfrac{2\times S}{6.023\times C}} - r_O}{\sqrt{2\times d_{TiO}^2 \times (1-\cos 109.5°)}}$ |
| 12b | 10 | M | |
| 13a | 11 | C | |
| 13b | 10 | M | |
| 16a | 11 | C | |
| 16b | 10 | M | |

$$n_{M(TiO-SiO)}(2) = 1 + \dfrac{L-(k_{TiO}+r_O)}{k_{ZrO}} = 1 + \dfrac{\sqrt{\dfrac{2\times S}{6.023\times C}} - (k_{TiO}+r_O)}{\sqrt{2\times d_{ZrO}^2 \times (1-\cos 109.5°)}}$$

$$n_{ZrO4*-ZrO}(2) = \dfrac{L-t_O}{k_{ZrO}} = \dfrac{\sqrt{\dfrac{2\times S}{6.023\times C}} - r_O}{\sqrt{2\times d_{ZrO}^2 \times (1-\cos 109.5°)}}$$

$$n_{M(ZrO-TiO)}(2) = 1 + \dfrac{L-(k_{ZrO}+r_O)}{k_{TiO}} = 1 + \dfrac{\sqrt{\dfrac{2\times S}{6.023\times C}} - (k_{ZrO}+r_O)}{\sqrt{2\times d_{TiO}^2 \times (1-\cos 109.5°)}}$$

$$n_{M(TiO4-ZrO)} \approx n_{ZrO4*-ZrO}; \; n_{M(ZrO4*-TiO)} \approx n_{TiO4*-TiO}$$

| | | | |
|---|---|---|---|
| 10a | 12 | G | |
| 10b | 13 | H | $n_{TiO4*-Silane}(2) = \dfrac{L-(k_{TiO}+r_O)}{k_{SiO}} = \dfrac{\sqrt{\dfrac{2\times S}{6.023\times C}} - (k_{SiO}+r_O)}{\sqrt{2\times d_{SiO}^2 \times (1-\cos 109.5°)}}$ |
| 14a | 12 | G | |
| 14b | 13 | H | |

$$n_{ZrO4*-Silane}(2) = \dfrac{L-(k_{ZrO}+r_O)}{k_{SiO}} = \dfrac{\sqrt{\dfrac{2\times S}{6.023\times C}} - (k_{ZrO}+r_O)}{\sqrt{2\times d_{SiO}^2 \times (1-\cos 109.5°)}}$$

*These coupling options are illustrated in FIG. 7.

Results of the geometric assessment using equations presented in Table 5 and Table 6 are given for each different porous silica sorbent material combination (i.e., combinations 1, 3-4, 6-10, 12-14 and 16 as described in Table 2) in the following Tables 7 to 13.

TABLE 7

Assessment of silicon-oxide ($SiO_4$)-and silane-mediated covalent coupling with aminoalkyl silane compounds. See also FIG. 7 coupling options A and D.

| S (m²/g) | C (mmol/g) | s (Å²/OH) | D (Å) | L (Å) | $n_{1,SiO}$ | $n_{2,SiO}$ | $n_{SiO}$ | $C_{SiO}$ (mmol/g) |
|---|---|---|---|---|---|---|---|---|
| Variable density of silanol groups on the silica surface ||||||||||
| 500 | 0.66 | 125.02 | 11.18 | 15.81 | 5.92 | 5.13 | 5 | 3.32 |
| 500 | 1.50 | 55.34 | 7.44 | 10.52 | 3.76 | 3.26 | 3 | 4.50 |
| 500 | 2.00 | 41.51 | 6.44 | 9.11 | 3.18 | 2.76 | 3 | 6.00 |

TABLE 7-continued

Assessment of silicon-oxide (SiO$_4$)-and silane-mediated covalent coupling with aminoalkyl silane compounds. See also FIG. 7 coupling options A and D.

| S (m$^2$/g) | C (mmol/g) | s (Å$^2$/OH) | D (Å) | L (Å) | n$_{1,SiO}$ | n$_{2,SiO}$ | n$_{SiO}$ | C$_{SiO}$ (mmol/g) |
|---|---|---|---|---|---|---|---|---|
| 500 | 2.50 | 33.21 | 5.76 | 8.15 | 2.79 | 2.42 | 2 | 5.00 |
| 500 | 3.20 | 25.94 | 5.09 | 7.20 | 2.40 | 2.08 | 2 | 6.40 |
| Constant density of silanol groups on the silica surface ||||||||| 
| 300 | 1.2 | 41.51 | 6.44 | 9.11 | 3.18 | 2.76 | 3 | 3.60 |
| 375 | 1.5 | 41.51 | 6.44 | 9.11 | 3.18 | 2.76 | 3 | 4.50 |
| 500 | 2 | 41.51 | 6.44 | 9.11 | 3.18 | 2.76 | 3 | 6.00 |
| 625 | 2.5 | 41.51 | 6.44 | 9.11 | 3.18 | 2.76 | 3 | 7.50 |
| 800 | 3.2 | 41.51 | 6.44 | 9.11 | 3.18 | 2.76 | 3 | 9.60 | n$_{SiO}$ is the maximum number of accommodated tetrahedral SiO$_4$ units after balancing between n$_{1,SiO}$ of configuration 1 and n$_{2,SiO}$ of configuration 2.
C$_{SiO}$ is the maximum loading capacity of the SiO$_4$ units and/or the maximum loading capacity of the alkyl amino group of the silane compounds. This amount is calculated as C$_{SiO}$ = n$_{SiO}$ × C.

TABLE 8

Assessment of silicon-oxide (SiO$_4$)- and silane-mediated covalent coupling with the covalent attachment of tetravalent metal oxide (MO$_4$) and aminoalkyl silane compounds. See also FIG. 7 coupling options E and B.

| S (m$^2$/g) | C (mmol/g) | s (Å$^2$/OH) | n$_{Silane}$ | n$_{1,TiO}$ | n$_{2,TiO}$ | n$_{1,ZrO}$ | n$_{2,ZrO}$ | n$_{MO}$ | C$_{MO}$ (mmol/g) | C$_{M-OH}$ (mmol/g) |
|---|---|---|---|---|---|---|---|---|---|---|
| Variable density of silanol groups on the silica surface |||||||||||
| 500 | 0.66 | 125.02 | 1 | 4.41 | 3.70 | 4.17 | 3.50 | 3 | 1.98 | 4.62 |
| 500 | 1.50 | 55.34 | 1 | 2.47 | 2.02 | 2.34 | 1.91 | 2 | 3.00 | 7.50 |
| 500 | 2.00 | 41.51 | 1 | 1.95 | 1.57 | 1.85 | 1.49 | 1 | 2.00 | 6.00 |
| 500 | 2.50 | 33.21 | 1 | 1.60 | 1.27 | 1.51 | 1.20 | 1 | 2.50 | 7.50 |
| 500 | 3.20 | 25.94 | 1 | 1.25 | 0.96 | 1.19 | 0.91 | 1 | 3.20 | 9.60 |
| Constant density of silanol groups on the silica surface |||||||||||
| 300 | 1.2 | 41.51 | 1 | 1.95 | 1.57 | 1.85 | 1.49 | 1 | 1.20 | 3.60 |
| 375 | 1.5 | 41.51 | 1 | 1.95 | 1.57 | 1.85 | 1.49 | 1 | 1.50 | 4.50 |
| 500 | 2 | 41.51 | 1 | 1.95 | 1.57 | 1.85 | 1.49 | 1 | 2.00 | 6.00 |
| 625 | 2.5 | 41.51 | 1 | 1.95 | 1.57 | 1.85 | 1.49 | 1 | 2.50 | 7.50 |
| 800 | 3.2 | 41.51 | 1 | 1.95 | 1.57 | 1.85 | 1.49 | 1 | 3.20 | 9.60 | n$_{MO}$ is the maximum number of accommodated tetrahedral MO$_4$ units after balancing between n$_{1,MO}$ of Configuration 1 and n$_{2,MO}$ of Configuration 2.
C$_{MO}$ is the maximum loading capacity of the MO$_4$ units. This amount is calculated as C$_{MO}$ = n$_{MO}$ × C.
C$_{OH}$ is the maximum loading capacity of the hydroxyl groups available for covalent adsorption of MoO$_4^{2-}$ or WO$_4^{2-}$ ions. This amount is calculated as C$_{M-OH}$ = [(n$_{MO}$ × 2) + 1] × C.
M is either one of the tetravalent metals, Ti or Zr.

TABLE 9

Assessment of silicon-oxide (SiO$_4$)-mediated covalent coupling with the covalent attachment of tetravalent metal oxide (MO$_4$). See also FIG. 7 coupling option F.

| S (m$^2$/g) | C (mmol/g) | s (Å$^2$/OH) | n$_{1,TiO}$ | n$_{2,TiO}$ | n$_{1,ZrO}$ | n$_{2,ZrO}$ | n$_{MO}$ | C$_{MO}$ (mmol/g) | C$_{M-OH}$ (mmol/g) |
|---|---|---|---|---|---|---|---|---|---|
| Variable density of silanol groups on the silica surface ||||||||||
| 500 | 0.66 | 125.02 | 4.41 | 3.70 | 4.17 | 3.50 | 3 | 2.64 | 6.60 |
| 500 | 1.50 | 55.34 | 2.47 | 2.02 | 2.34 | 1.91 | 2 | 4.50 | 12.00 |
| 500 | 2.00 | 41.51 | 1.95 | 1.57 | 1.85 | 1.49 | 1 | 4.00 | 12.00 |
| 500 | 2.50 | 33.21 | 1.60 | 1.27 | 1.51 | 1.20 | 1 | 5.00 | 15.00 |
| 500 | 3.20 | 25.94 | 1.25 | 0.96 | 1.19 | 0.91 | 1 | 6.40 | 19.20! |
| Constant density of silanol groups on the silica surface ||||||||||
| 300 | 1.2 | 41.51 | 1.95 | 1.57 | 1.85 | 1.49 | 1 | 2.40 | 7.20 |
| 375 | 1.5 | 41.51 | 1.95 | 1.57 | 1.85 | 1.49 | 1 | 3.00 | 9.00 |
| 500 | 2 | 41.51 | 1.95 | 1.57 | 1.85 | 1.49 | 1 | 4.00 | 12.00 |

TABLE 9-continued

Assessment of silicon-oxide (SiO$_4$)-mediated covalent coupling with the covalent attachment of tetravalent metal oxide (MO$_4$). See also FIG. 7 coupling option F.

| S (m$^2$/g) | C (mmol/g) | s (Å$^2$/OH) | $n_{1,TiO}$ | $n_{2,TiO}$ | $n_{1,ZrO}$ | $n_{2,ZrO}$ | $n_{MO}$ | $C_{MO}$ (mmol/g) | $C_{M-OH}$ (mmol/g) |
|---|---|---|---|---|---|---|---|---|---|
| 625 | 2.5 | 41.51 | 1.95 | 1.57 | 1.85 | 1.49 | 1 | 5.00 | 15.00 |
| 800 | 3.2 | 41.51 | 1.95 | 1.57 | 1.85 | 1.49 | 1 | 6.40 | 19.20 |

$n_{MO}$ is the maximum number of accommodated tetrahedral MO$_4$ units after balancing between the values of $n_{1,ZrO}$ and $n_{1,TiO}$ of Configuration 1 and the values of $n_{2,ZrO}$ and $n_{2,TiO}$ of Configuration 2.
$C_{MO}$ is the maximum loading capacity of the MO$_4$ units. This amount is calculated as $C_{MO} = n_{MO} + 1) \times C$.
$C_{OH}$ is the maximum loading capacity of the hydroxyl groups available for covalent adsorption of MoO$_4^{2-}$ or WO$_4^{2-}$ ions. This amount is calculated as $C_{M-OH} = [(n_{MO} + 1) \times 2 + 2] \times C$.
M is either one of the tetravalent metals, Ti or Zr.

TABLE 10

Assessment of tetravalent metal oxide (MO$_4$)-mediated covalent coupling with the covalent attachment of tetravalent metal oxide (MO$_4$) and aminoalkyl silane compounds. See also FIG. 7 coupling option M.

| S (m$^2$/g) | C (mmol/g) | s (Å$^2$/OH) | $n_{1,TiO}$ | $n_{2,TiO}$ | $n_{1,ZrO}$ | $n_{2,ZrO}$ | $n_{MO}$ | $C_{MO}$ (mmol/g) | $C_{M-OH}$ (mmol/g) |
|---|---|---|---|---|---|---|---|---|---|
| Variable density of silanol groups on the silica surface ||||||||||
| 500 | 0.66 | 125.02 | 5.31 | 4.59 | 5.02 | 4.35 | 4 | 2.64 | 5.28 |
| 500 | 1.50 | 55.34 | 3.37 | 2.92 | 3.19 | 2.76 | 3 | 4.50 | 9.00 |
| 500 | 2.00 | 41.51 | 2.85 | 2.47 | 2.70 | 2.34 | 2 | 4.00 | 8.00 |
| 500 | 2.50 | 33.21 | 2.50 | 2.16 | 2.37 | 2.05 | 2 | 5.00 | 10.00 |
| 500 | 3.20 | 25.94 | 2.15 | 1.86 | 2.04 | 1.76 | 1 | 3.20 | 6.40 |
| Constant density of silanol groups on the silica surface ||||||||||
| 300 | 1.2 | 41.51 | 2.85 | 2.47 | 2.70 | 2.34 | 2 | 2.40 | 4.80 |
| 375 | 1.5 | 41.51 | 2.85 | 2.47 | 2.70 | 2.34 | 2 | 3.00 | 6.00 |
| 500 | 2 | 41.51 | 2.85 | 2.47 | 2.70 | 2.34 | 2 | 4.00 | 8.00 |
| 625 | 2.5 | 41.51 | 2.85 | 2.47 | 2.70 | 2.34 | 2 | 5.50 | 10.00 |
| 800 | 3.2 | 41.51 | 2.85 | 2.47 | 2.70 | 2.34 | 2 | 6.40 | 12.80 |

$n_{MO}$ is the maximum number of accommodated tetrahedral MO$_4$ units after balancing between the values of $n_{1,TiO}$ and $n_{1,ZrO}$ of Configuration 1 and the values of $n_{2,TiO}$ and $n_{2,ZrO}$ of Configuration 2.
$C_{MO}$ is the maximum loading capacity of the MO$_4$ units. This amount is calculated as $C_{MO} = n_{MO} \times C$.
$C_{OH}$ is the maximum loading capacity of the hydroxyl groups available for covalent adsorption of MoO$_4^{2-}$ or WO$_4^{2-}$ ions. This amount is calculated as $C_{M-OH} = [(n_{MO} - 1) \times 2 + 2] \times C$.
M is either one of the tetravalent metals, Ti or Zr.

TABLE 11

Assessment of tetravalent metal oxide (MO$_4$)-mediated covalent coupling with the covalent attachment of more tetravalent metal oxides (MO$_4$). See also FIG. 7 coupling option C.

| S (m$^2$/g) | C mmol/g) | s (Å$^2$/OH) | $n_{1,TiO}$ | $n_{2,TiO}$ | $n_{1,ZrO}$ | $n_{2,ZrO}$ | $n_{MO}$ | $C_{MO}$ (mmol/g) | $C_{M-OH}$ (mmol/g) |
|---|---|---|---|---|---|---|---|---|---|
| Variable density of silanol groups on the silica surface ||||||||||
| 500 | 0.66 | 125.02 | 5.31 | 4.59 | 5.02 | 4.35 | 4 | 3.30 | 7.26 |
| 500 | 1.50 | 55.34 | 3.37 | 2.92 | 3.19 | 2.76 | 3 | 6.00 | 13.50 |
| 500 | 2.00 | 41.51 | 2.85 | 2.47 | 2.70 | 2.34 | 2 | 6.00 | 14.00 |
| 500 | 2.50 | 33.21 | 2.50 | 2.16 | 2.37 | 2.05 | 2 | 7.50 | 17.50 |
| 500 | 3.20 | 25.94 | 2.15 | 1.86 | 2.04 | 1.76 | 1 | 6.40 | 16.00 |
| Constant density of silanol groups on the silica surface ||||||||||
| 300 | 1.2 | 41.51 | 2.85 | 2.47 | 2.70 | 2.34 | 2 | 3.60 | 8.40 |
| 375 | 1.5 | 41.51 | 2.85 | 2.47 | 2.70 | 2.34 | 2 | 4.50 | 10.50 |
| 500 | 2 | 41.51 | 2.85 | 2.47 | 2.70 | 2.34 | 2 | 6.00 | 14.00 |
| 625 | 2.5 | 41.51 | 2.85 | 2.47 | 2.70 | 2.34 | 2 | 7.50 | 17.50 |
| 800 | 3.2 | 41.51 | 2.85 | 2.47 | 2.70 | 2.34 | 2 | 9.60 | 22.40 |

$n_{MO}$ is the maximum number of accommodated tetrahedral MO$_4$ units after balancing between the values of $n_{1,TiO}$ and $n_{1,ZrO}$ of Configuration 1 and the values of $n_{2,TiO}$ and $n_{2,ZrO}$ of Configuration 2.
$C_{MO}$ is the maximum loading capacity of the MO$_4$ units. This amount is calculated as $C_{MO} = n_{MO} + 1) \times C$.
$C_{OH}$ is the maximum loading capacity of the hydroxyl groups available for covalent adsorption of MoO$_4^{2-}$ or WO$_4^{2-}$ ions. This amount is calculated as $C_{M-OH} = [(n_{MO} - 1) \times 2 + 5] \times C$.
M is either one of the tetravalent metals, Ti or Zr.

TABLE 12

Assessment of tetravalent metal oxide (MO$_4$)-mediated covalent coupling with the covalent attachment of aminoalkyl silane compounds. See also FIG. 7 coupling option G.

Variable density of silanol groups on the silica surface

| S (m$^2$/g) | C (mmol/g) | s (Å$^2$/OH) | $n_{1,SiO}$ (TiO) | $n_{2,SiO}$ (TiO) | $n_{1,SiO}$ (ZrO) | $n_{2,SiO}$ (ZrO) | $n_{Silane}$ | $C_{Silane}$ (mmol/g) | $C_{MO}$ (mmol/g) | $C_{M-OH}$ (mmol/g) |
|---|---|---|---|---|---|---|---|---|---|---|
| 500 | 0.66 | 125.02 | 4.80 | 4.01 | 4.74 | 3.94 | 4 | 3.30 | 0.66 | 0.66 |
| 500 | 1.50 | 55.34 | 2.64 | 2.14 | 2.58 | 2.07 | 2 | 4.50 | 1.50 | 1.50 |
| 500 | 2.00 | 41.51 | 2.06 | 1.64 | 2.00 | 1.57 | 1 | 4.00 | 2.00 | 2.00 |
| 500 | 2.50 | 33.21 | 1.67 | 1.30 | 1.61 | 1.23 | 1 | 5.00 | 2.50 | 2.50 |
| 500 | 3.20 | 25.94 | 1.28 | 0.96 | 1.22 | 0.90 | 1 | 6.40 | 3.20 | 3.20 |

Constant density of silanol groups on the silica surface

| S (m$^2$/g) | C (mmol/g) | s (Å$^2$/OH) | $n_{1,SiO}$ (TiO) | $n_{2,SiO}$ (TiO) | $n_{1,SiO}$ (ZrO) | $n_{2,SiO}$ (ZrO) | $n_{SiO}$ | $C_{Silane}$ (mmol/g) | $C_{MO}$ (mmol/g) | $C_{M-OH}$ (mmol/g) |
|---|---|---|---|---|---|---|---|---|---|---|
| 300 | 1.2 | 41.51 | 2.06 | 1.64 | 2.00 | 1.57 | 1 | 2.40 | 1.20 | 1.20 |
| 375 | 1.5 | 41.51 | 2.06 | 1.64 | 2.00 | 1.57 | 1 | 3.00 | 1.50 | 1.50 |
| 500 | 2 | 41.51 | 2.06 | 1.64 | 2.00 | 1.57 | 1 | 4.00 | 2.00 | 2.00 |
| 625 | 2.5 | 41.51 | 2.06 | 1.64 | 2.00 | 1.57 | 1 | 5.00 | 2.50 | 2.50 |
| 800 | 3.2 | 41.51 | 2.06 | 1.64 | 2.00 | 1.57 | 1 | 6.40 | 3.20 | 3.20 |

$n_{SiO}$ is the maximum number of accommodated tetrahedral SiO$_4$ units after balancing between the values of $n_{1,SiO(TiO)}$ and $n_{1,SiO(ZrO)}$ of Configuration 1 and the values of $n_{2,SiO(TiO)}$ and $n_{2,SiO(ZrO)}$ of Configuration 2.
$C_{MO}$ is the maximum loading capacity of the MO$_4$ units. This amount is calculated as $C_{MO} = n_{MO} \times C$.
$C_{OH}$ is the maximum loading capacity of the hydroxyl groups available for covalent adsorption of MoO$_4^{2-}$ or WO$_4^{2-}$ ions. This amount is calculated as $C_{M-OH} = n_{MO} \times C$. $C_{Silane} = (n_{SiO} + 1) \times C$.
M is either one of the tetravalent metals, Ti or Zr.

TABLE 13

Assessment of tetravalent metal oxide (MO$_4$)-mediated covalent coupling with the covalent attachment of aminoalkyl silane compounds and MO$_4$ groups. See also FIG. 7 coupling option H.

Variable density of silanol groups on the silica surface

| S (m$^2$/g) | C (mmol/g) | s (Å$^2$/OH) | $n_{1,SiO}$ (TiO) | $n_{2,SiO}$ (TiO) | $n_{1,SiO}$ (ZrO) | $n_{2,SiO}$ (ZrO) | $n_{Silane}$ | $C_{Silane}$ (mmol/g) | $C_{MO}$ (mmol/g) | $C_{M-OH}$ (mmol/g) |
|---|---|---|---|---|---|---|---|---|---|---|
| 500 | 0.66 | 125.02 | 4.80 | 4.01 | 4.74 | 3.94 | 4 | 2.64 | 0.66 | 0.66 |
| 500 | 1.50 | 55.34 | 2.64 | 2.14 | 2.58 | 2.07 | 2 | 3.00 | 1.50 | 1.50 |
| 500 | 2.00 | 41.51 | 2.06 | 1.64 | 2.00 | 1.57 | 1 | 2.00 | 2.00 | 2.00 |
| 500 | 2.50 | 33.21 | 1.67 | 1.30 | 1.61 | 1.23 | 1 | 2.50 | 2.50 | 2.50 |
| 500 | 3.20 | 25.94 | 1.28 | 0.96 | 1.22 | 0.90 | 1 | 3.2 | 3.20 | 3.20 |

Constant density of silanol groups on the silica surface

| S (m$^2$/g) | C (mmol/g) | s (Å$^2$/OH) | $n_{1,SiO}$ (TiO) | $n_{2,SiO}$ (TiO) | $n_{1,SiO}$ (ZrO) | $n_{2,SiO}$ (ZrO) | $n_{SiO}$ | $C_{Silane}$ (mmol/g) | $C_{MO}$ (mmol/g) | $C_{M-OH}$ (mmol/g) |
|---|---|---|---|---|---|---|---|---|---|---|
| 300 | 1.2 | 41.51 | 2.06 | 1.64 | 2.00 | 1.57 | 1 | 1.2 | 2.40 | 4.80 |
| 375 | 1.5 | 41.51 | 2.06 | 1.64 | 2.00 | 1.57 | 1 | 1.5 | 3.00 | 6.00 |
| 500 | 2 | 41.51 | 2.06 | 1.64 | 2.00 | 1.57 | 1 | 2 | 4.00 | 8.00 |
| 625 | 2.5 | 41.51 | 2.06 | 1.64 | 2.00 | 1.57 | 1 | 2.5 | 5.00 | 10.00 |
| 800 | 3.2 | 41.51 | 2.06 | 1.64 | 2.00 | 1.57 | 1 | 3.2 | 6.40 | 12.80 |

$n_{SiO}$ is the maximum number of accommodated tetrahedral SiO$_4$ units after balancing between the values of $n_{1,SiO(TiO)}$ and $n_{1,SiO(ZrO)}$ of Configuration 1 and the values of $n_{2,SiO(TiO)}$ and $n_{2,SiO(ZrO)}$ of Configuration 2.
$C_{MO}$ is the maximum loading capacity of the MO$_4$ units. This amount is calculated as $C_{MO} = n_{MO} \times C$.
$C_{OH}$ is the maximum loading capacity of the hydroxyl groups available for covalent adsorption of MoO$_4^{2-}$ or WO$_4^{2-}$ ions. This amount is calculated as $C_{M-OH} = (n_{MO} \times 2 \times C)$. $C_{silane} = n_{Silane} \times C$.
M is either one of the tetravalent metals, Ti or Zr.

Based on the results shown in the Tables 7 to 13, values of the density of silanol groups from s=55.34 (Å$^2$/OH) to s=33.21 (Å$^2$/OH) are suitable for an effective covalent coating of the functional groups with the silica. The preferable value of 41.51 (Å$^2$/OH) is used for the synthesis of the sorbents. As shown in Tables 7 to 13, the surface area S of the silica (when investigated at a constant silanol density) has a strong effect on the adsorption capacity or functional group loading of the synthesised sorbents. The silica sorbents with a surface area 600 to 1000 m$^2$/g, with an ion exchange capacity C>2 mmol/g and a silanol density s>41.51 (Å$^2$/OH), are optimised parameters for the covalent coupling of the aminoalkyl silanes and tetravalent metal hydroxides to the silica surface.

Sorbents synthesised using a silica substrate having a constant silanol density (41.51 Å$^2$/OH) and variable surface areas S are listed in the bottom parts of the Tables 7 to 10. As shown, the combination of using a large specific surface area silica substrate and a properly chosen mediator-based covalent coupling method produces a high performance sorbent material.

Separation, Concentration and Purification Performance

Figure 8:
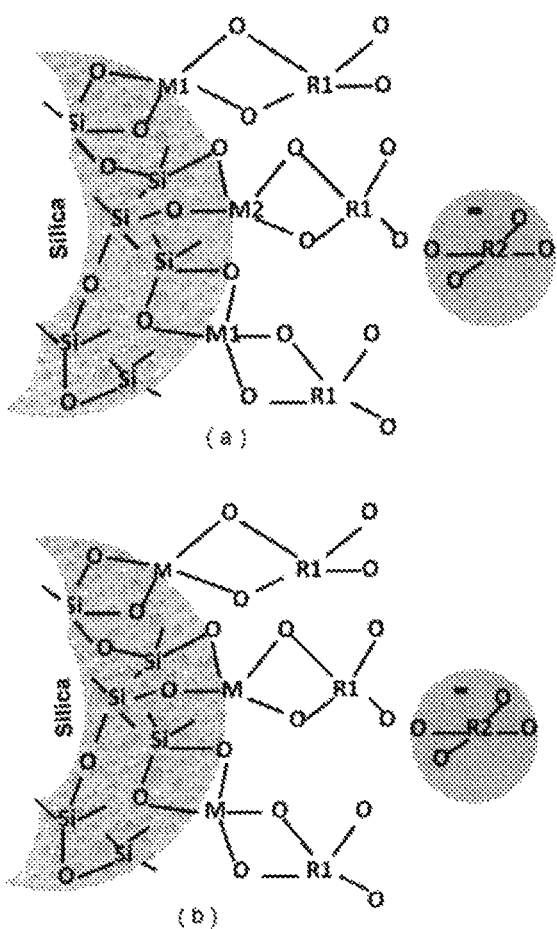
FIG. 8 is a diagram showing the adsorption of radioisotopes on multifunctional sorbent materials in radioisotope generator production and radioisotope purification/concentration processes:
(a) adsorption of a parent nuclide (R1) on, and desorption/exclusion of a daughter radioisotope (R2) from, a mixed-metal oxide functionalised silica in a radioisotope generator; M1 and M2 are, for example, independently either Zr or Ti; and, (b) adsorption of a parent nuclide (R1) on, and desorption of a daughter radioisotope (R2) from, a metal oxide functionalised silica in a radioisotope generator; M is, for example, either Zr or Ti.
Figure 9:
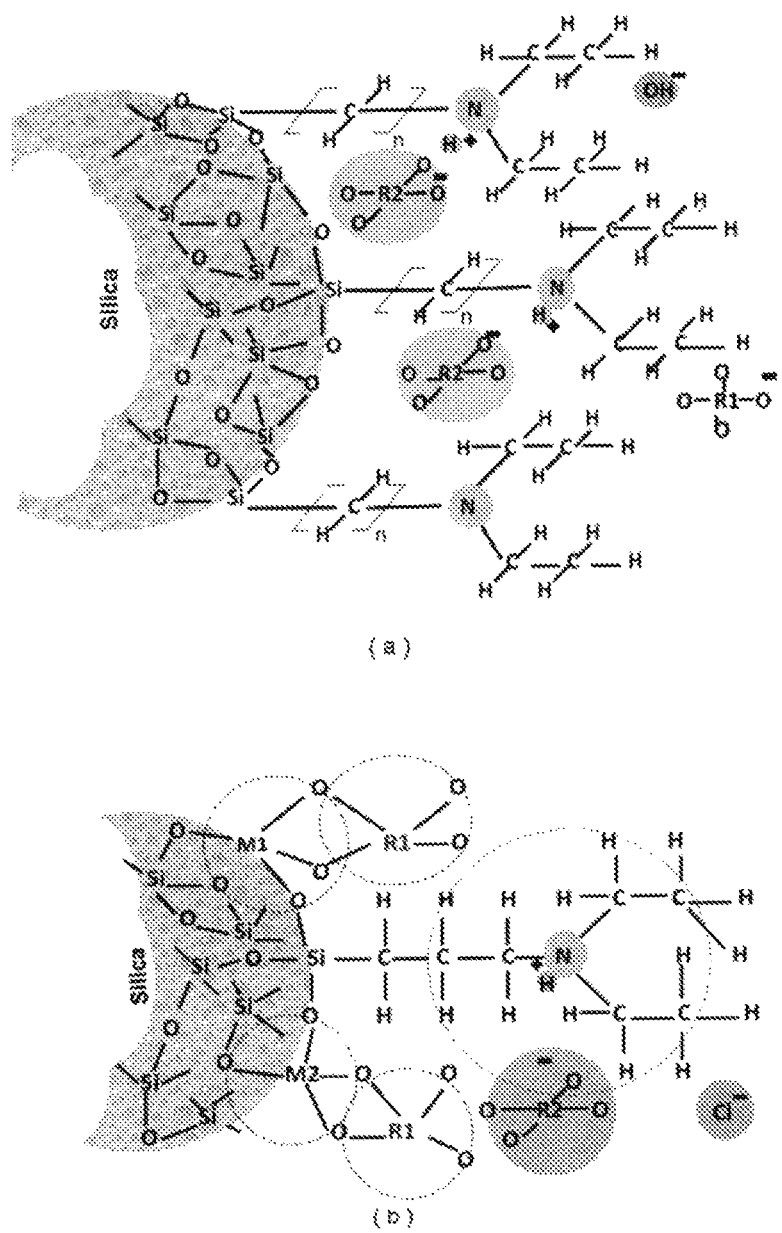
FIG. 9 is a diagram showing adsorption of radioisotopes on multifunctional sorbent materials: (a) reversible adsorption (catch-and-release) of a daughter radioisotope (R2) on, and exclusion of a parent nuclide (R1) from, an aminoalkyl functionalised silica in a radioisotope generator production and radioisotope purification/concentration process, and (b) the irreversible adsorption of a parent nuclide (R1) and reversible adsorption of a daughter radioisotope (R2) on a mixed-metal oxide and aminoalkyl functionalised silica; M1 and M2 are, for example, independently either Zr or Ti in a radioisotope purification/concentration process.

The following examples describe the experimental performance of the above synthesised sorbent materials in separating, concentrating and purifying mixtures comprising anionic contaminant species of formula $[Z^1O_4]^{2-}$ and at least one target species of formula $[Z^2O_4]^-$, wherein $Z^1$=Mo or W and $Z^2$=Tc or Re. FIGS. 8(*a*) and (*b*) illustrate the separation and purification functionalities of the sorbent materials of the present invention, where anionic contaminant species are irreversibly bound to the sorbent material surface (i.e., R1 in FIGS. 8(*a*) and (*b*)) and the target species (R2O$_4^-$ in FIGS. 8(*a*) and (*b*)) pass through the sorbent without interaction to be collected in the eluent. FIG. 9 illustrates the separation, concentration and purification functionalities of the sorbent materials of the present invention, where anionic contaminant species are irreversibly bound to the sorbent material surface (i.e., R1 in FIG. 9) and the target species (R2O$_4^-$ in FIG. 9) reversibly binds to the charged aminoalkyl group via an ionic interaction, before a new eluting solution is provided to release the target species for recovery in the eluent.

Example 4: Comparative Adsorption Capacity

The molybdenum and tungsten adsorption capacity of selected sorbent materials according to the present invention are shown in Table 14 compared to the adsorption capacity of selected non-inventive materials PZC (polymeric zirconium compound), nanocrystalline zirconia, sulfated alumina/alumina sulfated zirconia and alumina. The selected multifunctional sorbents in Table 14 are silica functionalised with ZrO$_4$. The silica gel used in the synthesis of the sorbent materials had a silanol group density of 40.21 Å$^2$/OH and a specific area of 308-958 m$^2$/g silica. The synthesis method used was as described above for Method 3: Self-mediated covalent coupling (S-MCC) using zirconium-ethoxide as a mediator. The Zr metal content of the sorbents analysed by ICP-EOS are from 378.6 to 565 mg Zr/g sorbent material.

First, the generator column is packed with the sorbent material. A typical column may contain between about 2 g and about 4 g of the sorbent. Before loading with $^{99}$Mo/$^{188}$W solution, the generator column is washed with about 30 mL water. The stock $^{99}$Mo and $^{188}$W solution of pH 5.0-6.0 may be produced from low specific activity $^{99}$Mo or $^{188}$W targets, respectively, in a nuclear reactor or in a particle accelerator facility. In this example, the Mo concentration is about 100-110 mg Mo/mL and has a specific activity of >1.5 Ci/g Mo. The Mo-adsorption capacity of the tetravalent metal hydroxide-functionalised silica sorbent used in this example is about 675 mg Mo/g. The solution comprising [MoO$_4$]$^{2-}$ and/or [WO$_4$]$^{2-}$ is then contacted with the column. In this example, the $^{99}$Mo solution volume applied to the sorbent column is about 65 mL. The $^{99}$Mo activity loaded on the sorbent column is about 3 Ci. The stock $^{99}$Mo solution is loaded onto a sorbent column using a peristaltic pump, with a flow rate of 1-2 mL/minute. Following the loading, the column is washed with 30 mL 0.9% saline.

As described in the section entitled 'Purification and/or concentration methods' the $^{99}$Mo and/or $^{188}$W may then decay and produce [$^{99m}$TcO$_4$]$^-$ and/or [$^{188}$ReO$_4$]$^-$ ions, respectively, which may then be eluted from the sorbent column with between about 3 and about 5 mL of saline solution. If more than 4 g of the sorbent material is used in the generator column, the volume of the saline used for elution may be proportionally increased to more than 5 mL. The resulting saline eluate may contain the $^{99m}$Tc/$^{188}$Re as pertechnetate or perrhenate ions, with sodium as the counterbalancing cation.

A suitable apparatus (generator) for separating and purifying the target species $^{99m}$Tc or $^{188}$Re is shown in FIGS. 10 and 11. The $^{99m}$Tc/$^{99}$Mo and $^{188}$Re/$^{188}$W generator may

TABLE 14

Mo and W-adsorption/loading capacity of inventive sorbent materials synthesised using the silica substrates of specific surface area 300-1000 m$^2$/g compared to non-inventive materials PZC, nanocrystalline zirconia, sulfated alumina/alumina sulfated zirconia and alumina.

| Sorbent | Mo-adsorption capacity of sorbent, mg Mo/g sorbent | Mo-loading capacity of sorbent column, mg Mo/g column | W-adsorption capacity of sorbent, mg W/g sorbent | W-loading capacity of sorbent column, mg W/g column |
|---|---|---|---|---|
| Multifunctional sorbent materials of this invention | 456.1-692.0 | 313.2-445.6 | 874.0-1366.1 | 446.4-643.6 |
| PZC | 290.0 | 224.8 | 500.0 | 333.0 |
| Nanocrystalline zirconia | 250.0 | 200.0 | 312.0 | 327.8 |
| Sulfated alumina/alumina sulfated zirconia | 230 | 187 | 445 | 308 |
| Alumina | 10 | 9.9 | 20 | 19.6 |

Figure 14:
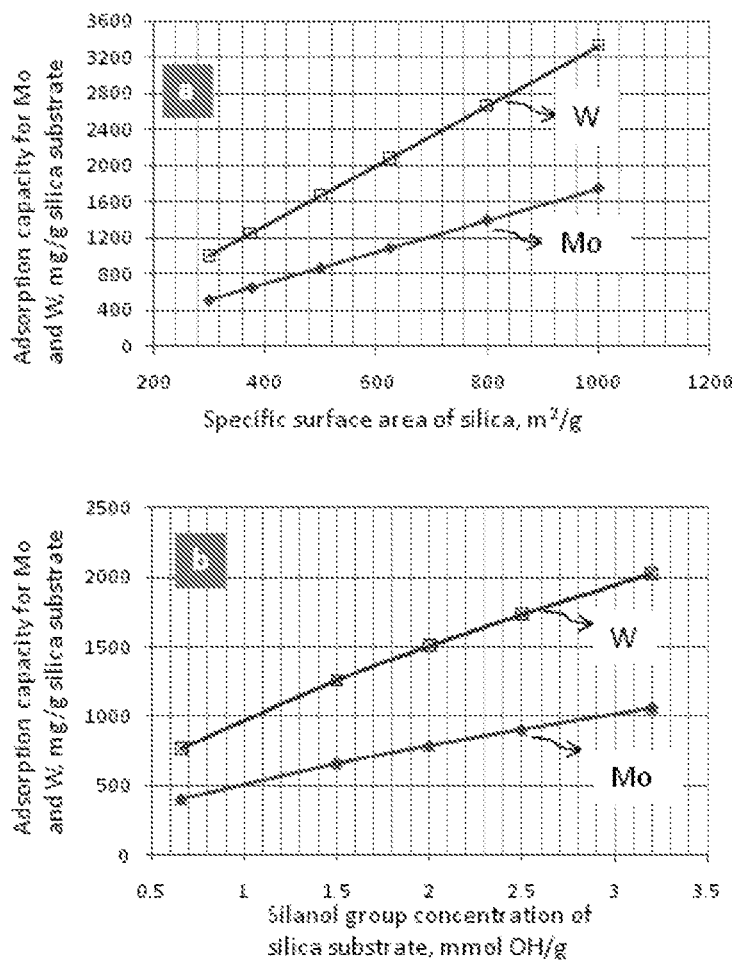
FIG. 14 is a graph showing the W- and Mo-adsorption capacity of $MO_4$-functionalised sorbents as a function of (a) the specific surface area; and, (b) silanol group concentration of the silica substrate used during synthesis.
Figure 15:
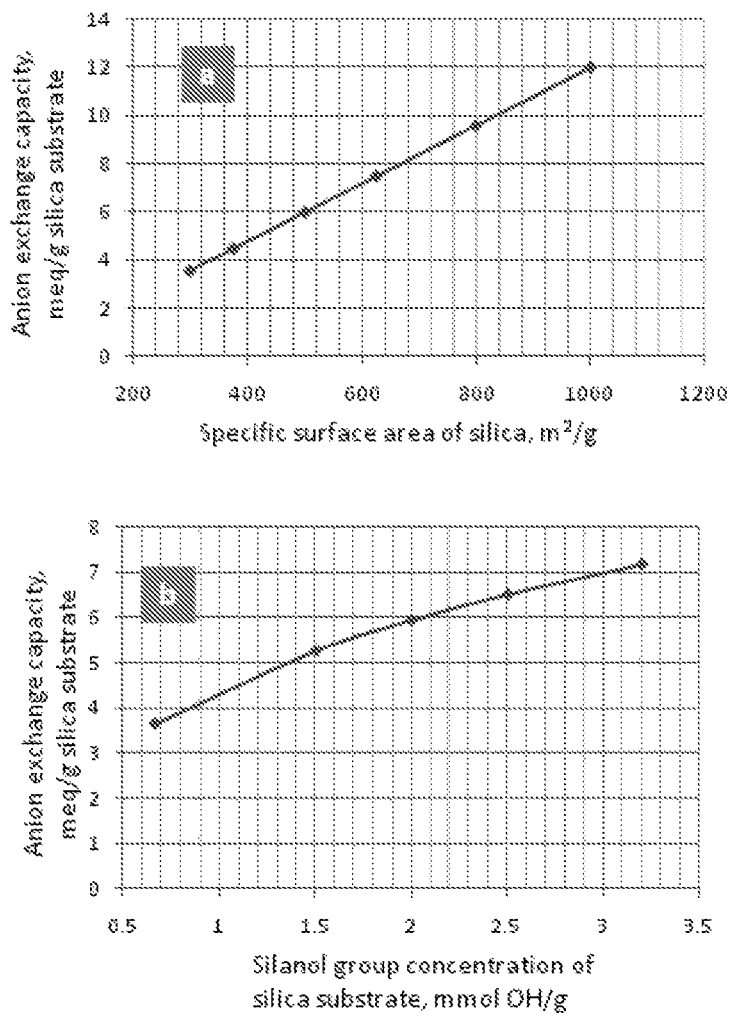
FIG. 15 is a graph showing anion exchange capacity of R"-functionalised sorbents as a function of (a) the specific surface area; and, (b) silanol group concentration of the silica substrate used during synthesis.

The adsorption capacity for Mo and W calculated based on data in Table 11 is given in FIG. 14 as a function of specific surface area of the silica and the silanol group concentration. The anion exchange capacity calculated for the same sorbent materials is given in FIG. 15 as a function of specific surface area of the silica and the silanol group concentration.

Example 5: Use of Sorbent Materials in a Generator Column

Sorbent materials as described in the section entitled 'Generator' may be used as described below.

comprise a generator column loaded with about 10 g of a tetravalent metal hydroxide-functionalised sorbent material. The generator column, which may be made from glass or thermoplastic material (e.g., polyetheretherketone (PEEK), polypropylene, polyethylene, cellulose acetate etc.) and may comprise fritted sintered quartz or fritted polypropylene filter disks at both its ends, may be filled with dry sorbent. The fritted filter disks may be of 20 μm porosity. The ends may be closed by polypropylene plastic septa together with neoprene and silicon rubber gaskets. The column may then be capped by aluminum clamping lids. The generator column may then be housed in a radiation protection shielding lead container, which may comprise both an outlet and inlet port for tubing. An eluent supply system comprising an eluent container may then be coupled to the generator column inlet for supplying an eluent to the sorbent column.

The eluent flow rate through columns may be controlled within a range of about 1.0 mL/minute to 5 mL/minute. Due to the irreversible binding of molybdate and tungstate ions on the tetravalent metal hydroxide-functionalised silica sorbent, the affinity of the sorbent in the generator column for the parent species $^{99}$Mo or $^{188}$W may be high, and therefore negligible quantities of the parent species may be eluted from the sorbent. However, as the affinity of the sorbent in generator and purification columns for $^{99m}$Tc or $^{188}$Re species may be relatively lower, these species may be readily eluted, resulting in an eluate that comprises a solution of $^{99m}$Tc or $^{188}$Re substantially free of contaminant ions. The $^{99m}$Tc concentration of the eluate in this example is about 1.0 Ci $^{99m}$Tc/mL. The recovery yield of the daughter nuclide $^{99m}$Tc or $^{188}$Re is greater than 95%.

Example 6: Use of Sorbent Materials in a Purification and/or Concentration Column Sorbent materials as described in the sections entitled 'Purification "catch without release"', 'Purification and concentration "catch and release" (I)' or 'Purification and concentration "catch and release" (II)' may additionally or alternatively be used as described below.

The generator column in Example 4 may be used in conjunction with a purification and/or concentration column as described below. The combined generator/purification column system may be referred to as an 'integrated generator system'. Alternatively, the purification and/or concentration column may be used in combination with an existing generator column or generator column not comprising any inventive sorbent material.

The purification process illustrated in FIG. 11 may be the 'integrated generator system' used for the purification of $^{99m}$Tc and/or $^{188}$Re eluates produced from $^{99m}$Tc/$^{99}$Mo and/or $^{188}$Re/$^{188}$W generators when eluted with normal saline. The purification column may comprise about 1.0 g of a sorbent material as described in the section entitled 'Purification "catch without release"'. Additionally, the process may comprise a peristaltic pump for pumping liquids through the generator and purification and/or concentration columns. The pump may be separately installed or may be shared with a pump located in a purification module. The pump may be located downstream of generator column or purification and/or concentration column so as to cause the liquids to pass through said columns by way of suction from the pump. Inlet and outlet valves may be coupled to the generator column. A controller or computer may be provided for controlling the operation of the generator. It may, for example, be capable of operating the valves and the pump. In the process of FIG. 11, 0.9% NaCl solution may be used to elute $^{99m}$Tc or $^{188}$Re when required, and the valves may be opened and pump may be turned on. This may cause eluent of 10 mL volume to flow from eluent supply system through generator column via the purification and/or concentration column so as to elute and purify the $^{99m}$Tc or $^{188}$Re before collection.

To avoid any spoiling effect on the purification and/or concentration column, which may be caused by radiolysis products of the eluent and/or breakthrough of contaminant ions, the purification and/or concentration column may be cleaned up after each elution performed. In this example, the clean-up process is performed by first washing with 3 mL of 0.5 M NaOH and then washing with 5 mL water. The clean-up effluent is collected in a waste container. By regenerating the column in this way, the lifetime of the purification column is increased. This feature also represents a significant benefit of the purification and/or concentration columns using sorbents materials as described herein over shorter life spans of sorbent columns presently available.

The purification and/or concentration column may alternatively comprise a sorbent material as described in the section entitled 'Purification and concentration "catch and release" (I)'. A process using such a column is described below with reference to FIG. 12, and the performance of this system is shown in FIG. 20(c).

The integrated generator system may comprise the generator column preparation, apparatus setup and loading of stock solution as described in Example 4; however, in this example, the $^{99}$Mo-loaded generator column is washed with 30 mL of 0.5 M acetic acid/0.05% (w/v) NaCl solution mixture or with 50 mL of <0.05% (w/v) NaCl solution before coupling with the purification and/or concentration column as follows: 10 g of a tetravalent metal hydroxide-functionalised silica sorbent is loaded in the generator column. The sorbent in generator column is fully loaded with parent species $^{99}$Mo or $^{188}$W of 4-7 Ci activity. A mixture of 0.5 M acetic acid/0.05% (w/v) NaCl solution or a <0.05/(w/v) NaCl solution is used as an eluent for elution of $^{99m}$Tc or $^{188}$Re. Once loaded in the generator column, the $^{99}$Mo or $^{188}$W gradually decays to form $^{99m}$Tc or $^{188}$Re, respectively. When a solution of daughter nuclide is required, valves are opened and the pump is turned on. This causes 20-30 mL of eluent to flow from eluent circulation system through generator column, optionally via the purification and/or concentration column and back to the eluent reservoir. The eluent flow rate through the columns is controlled within a range of about 1.0 mL/minute to 5 mL/minute.

The purification and/or concentration column may be smaller than generator column, and may be additionally or alternatively packed with a sorbent material according to the invention. A typical purification and/or concentration column may contain between about 0.1 g and about 0.3 g of the sorbent material. The $^{99m}$Tc/$^{188}$Re eluate containing $^{99m}$Tc/$^{188}$Re as pertechnetate or perrhenate ions and $^{99}$Mo/$^{188}$W contaminant eluted from the generator column may be passed, in line, through the purification column.

Figure 17:
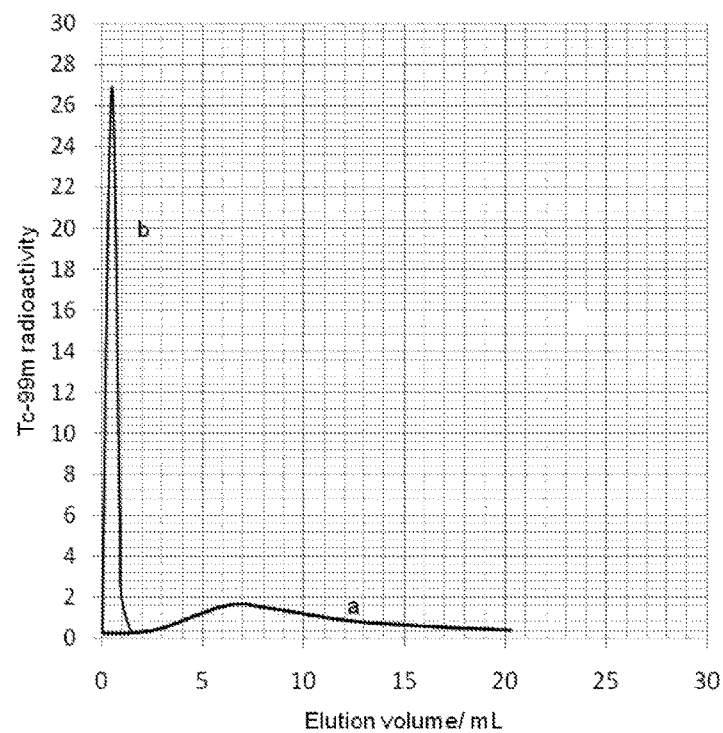
FIG. 17 shows $^{99}$Tc-elution profiles for: a, the eluate of the $^{99m}$Tc-generator column (used in Example 6 without coupling with a concentration column) containing MO$_4$-functionalised sorbents of the invention; b, the concentrated eluate eluted from the concentration column (used in Example 6 in combination with a generator column) containing R"-functionalised sorbents of the invention.
Figure 18:
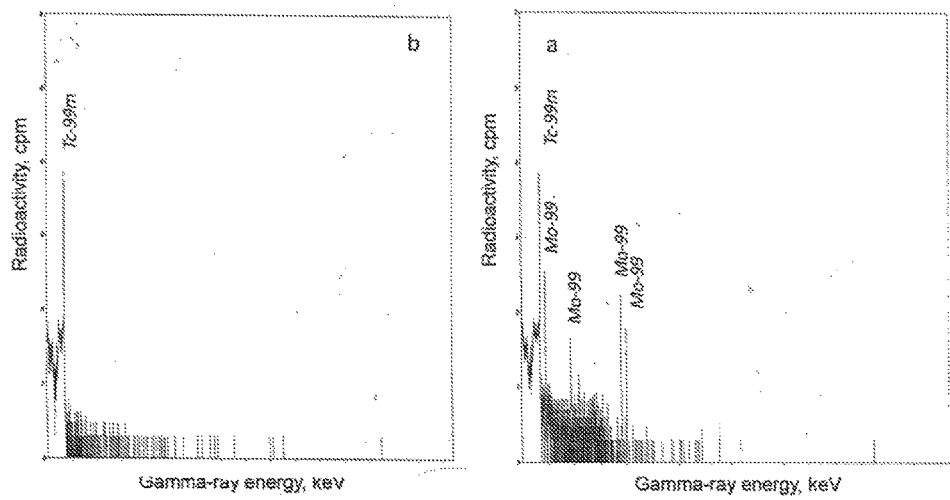
FIG. 18 shows gamma-ray spectrometric measurement of $^{99m}$Tc-eluates before and after concentration: a, the eluate of the $^{99m}$Tc-generator column containing MO$_4$-functionalised sorbents of the invention before performing a subsequent $^{99m}$Tc-concentration/purification process; b, the concentrated/purified eluate after using a concentration/purification column containing MO$_4$- and R"-functionalised sorbents of the invention.

When the generator eluate is passed through a purification and/or concentration column comprising 0.1-0.3 g of the aminoalkyl silane and tetravalent metal hydroxide functionalised sorbent, the contaminant ions may be irreversibly bound on the sorbent and the target ions may be reversibly bound on the sorbent. A small volume (around 1.5 mL) of the normal saline (eluting solution) may then be contacted with the sorbent material to release more than 90% of the $^{99m}$TcO$_4^-$ and/or $^{188}$ReO$_4^-$ ions from the purification and/or concentration column. The $^{99m}$Tc concentration of the eluate in this example is about 4-7 Ci $^{99m}$Tc/mL. The concentration factor of this concentration process is around 20. To remove the irreversibly bound contaminants from the sorbent, a clean-up process is performed by washing first with 3 mL of 0.5 M NaOH and then with 5 mL water. The clean-up effluent is collected in a waste container. The non-saline aqueous eluent (acetate solution) may be recycled for further elution of $^{99m}$Tc and $^{188}$Re from the generators. An optimal design of self-shielded device is based on a new sorbent which selectively retains $^{99m}$Tc from >20 mL $^{99m}$Tc eluate of the generator. The injectable $^{99m}$Tc is then eluted from the sorbent with 1.0 mL saline into an evacuated vial through a millipore filter. The $^{99m}$Tc eluate was concentrated around 20-fold with a $^{99m}$Tc recovery yield of >90% using this device. FIG. 17 shows $^{99m}$Tc-elution profiles for: a, the eluate of the $^{99m}$Tc-generator column (without coupling with concentration column) of MO$_4$-functionalised sorbents of the invention; and b, the concentrated eluate eluted from the concentration column (coupled with the generator column) of R"-functionalised sorbents of the invention. The $^{99}$Mo impurity in the $^{99m}$Tc eluate was totally eliminated. FIG. 18 shows the gamma-ray spectrometric measurement of $^{99m}$Tc-eluates before and after purification/concentration: a, the eluate of the $^{99m}$Tc-generator column containing MO$_4$-functionalised sorbents of the invention before performing a subsequent $^{99m}$Tc-concentration/purification process; and b, the concentrated/purified eluate after using a concentration/purification column containing MO$_4$- and R"-functionalised sorbents of the invention.

Figure 16:
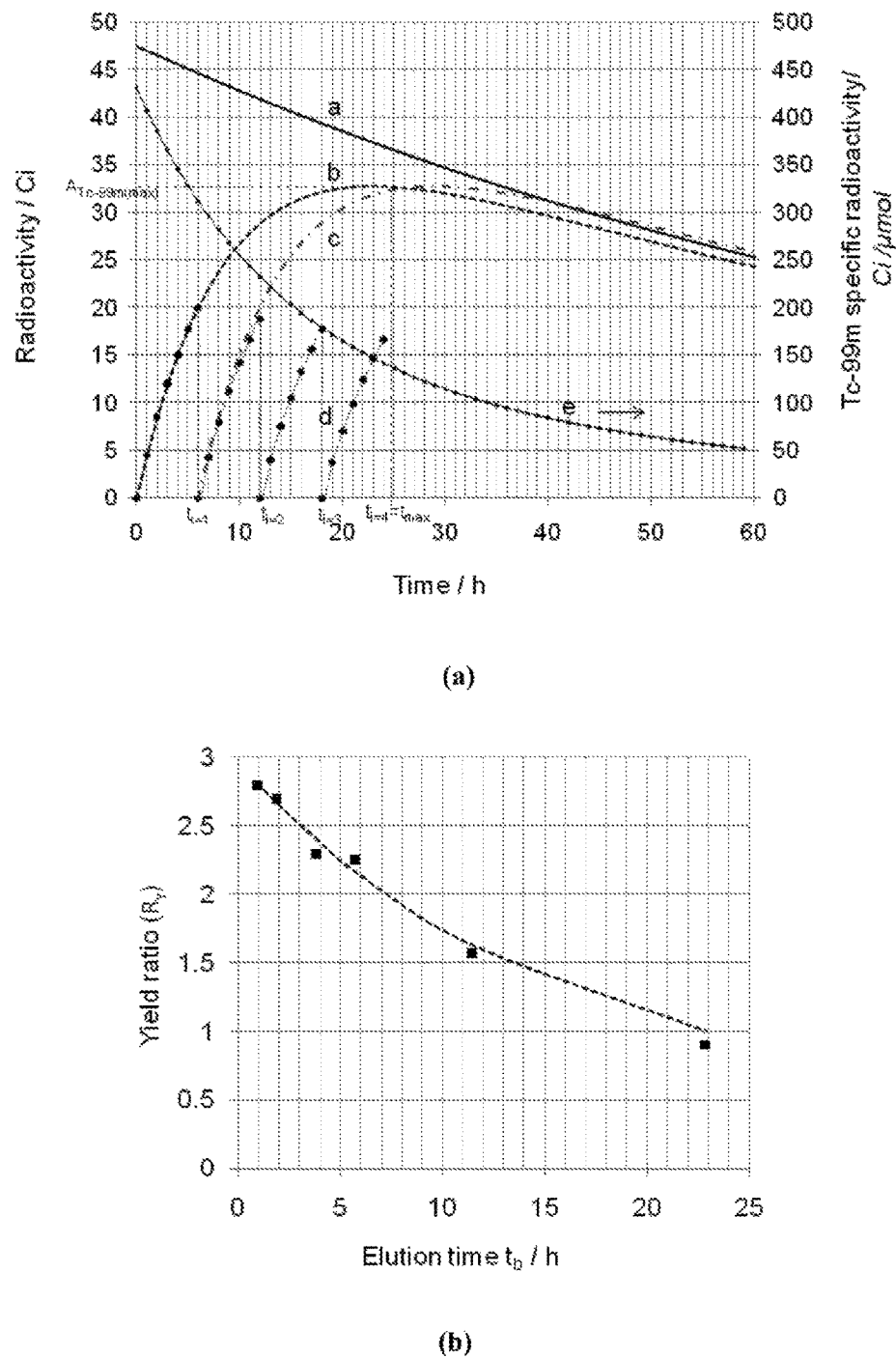
FIG. 16(a) is a graph illustrating the concept of the early elution method and $^{99m}Tc$-radioactivity build-up in a generator eluted with an early elution regime: a, Radioactivity of $^{99}Mo$; b, $^{99m}Tc$-radioactivity build-up from beginning; c, $^{99m}Tc$-radioactivity build-up after first elution; d, $^{99m}Tc$ radioactivity built-up/eluted at 6-hour elutions; e, Specific activity of $^{99m}$Tc in the system of $^{99m}$Tc-radioactivity build-up (from beginning); (b) is a graph showing the effectiveness of $^{99m}$Tc production yield increase for the generator eluted with an early elution regime compared with that normally eluted at the time point of maximal $^{99m}$Tc build-up. The square marks are experimental data and the dashed line is theoretical calculation results.

The use of multifunctional sorbents of the present invention in concentration processes offers economic benefits for users of generators, as the quality/specific activity (SA) of the eluted $^{99m}$Tc-solution in radiopharmaceutical preparations is improved, the residual radiation dose of $^{99m}$Tc for patients is reduced, and the costs of scans for patients are lowered. The $^{99m}$Tc/$^{99}$Mo is also more effectively utilised. Generally, the $^{99m}$Tc eluate produced from generators is eluted in fixed volumes, and the $^{99m}$Tc concentration of the eluate decreases with the lifetime of the generator due to radioactive decay of parent $^{99}$Mo nuclides. Moreover, the $^{99m}$Tc also decays to $^{99m}$Tc. This process not only reduces the $^{99m}$Tc-production yield or the effective utilisation of $^{99m}$Tc/$^{99}$Mo activity (i.e., a large quantity of $^{99m}$Tc activity is lost and the generator is non-economically exploited), but it also causes the specific activity (SA) of $^{99m}$Tc (SA is defined as ($^{99m}$Tc-atom numbers)/($^{99m}$Tc+$^{99}$Tc atom numbers)) to decrease continuously as shown in FIG. 16(a). This means that the elutions of the generator at a shorter build-up time of the daughter nuclide (target species) will give a higher accumulative $^{99m}$Tc-production yield (accumulative yield is the sum of all the yields achieved in each early elution performed before the maximal build-up time) and higher SA (i.e., a $^{99m}$Tc solution of better quality). However, each early $^{99m}$Tc-elution at shorter build-up time will result in a lower $^{99m}$Tc-production yield as shown in FIG. 16(a) and thus an eluate of lower $^{99m}$Tc-concentration.

The multifunctional sorbents of the present invention are capable of increasing the $^{99m}$Tc-production yield in radio-isotope concentration processes in combination with an 'early' elution regime. In the said 'early' elution regime, several consecutive elutions are carried out at any time before the time point ($t_{Max}$) of maximal $^{99m}$Tc build-up in the generator as described in FIG. 16(a). The sum of all $^{99m}$Tc-activity amounts obtained in consecutive elutions (Equation 11):

$$\sum_{i=1}^{i=n} A_{Tc-99m(E_i)} \qquad \text{Equation 11}$$

where $E_i$ is indexed for the i$^{th}$ elution, will be much higher than the $^{99m}$Tc-activity obtained in a currently used single elution performed at the time of maximal $^{99m}$Tc build-up ($A_{Tc-99m(Max)}$). The experimental (square marks) and theoretical calculated (dashed line) $^{99m}$Tc-yield ratio (Equation 12) shown in FIG. 16(b) confirm the usefulness of multifunctional sorbents of the present invention in concentration processes.

$$R_y = \sum_{i=1}^{i=n} A_{Tc-99m(E_i)} / A_{Tc-99m(Max)} \qquad \text{Equation 12}$$

As shown in FIG. 16(b), this early elution regime may increase both the $^{99m}$Tc-production yield (evaluated using $^{99m}$Tc-yield ratio, $R_y$) and the specific activity of the $^{99m}$Tc eluate by a factor of >2 for elutions performed at <6 hours build-up time compared with that of a $^{99m}$Tc-solution obtained in a currently used single elution performed at the time of maximal $^{99m}$Tc build-up.

The specific activity of carrier-included $^{99m}$Tc in the $^{99m}$Tc-eluate of the generator system eluted with an early elution regime is evaluated by Equation 13:

$$SA_{Tc-99m} = \frac{A_{Tc-99m}}{N_{Tc}} = \frac{\lambda_{Tc-99m} \cdot b \cdot \left(e^{-\lambda_{Mo} \cdot t} - e^{-\lambda_{Tc-99m} \cdot t}\right)}{0.6144 \times 10^{-7} \times \left(\frac{\lambda_{Tc-99m}}{\lambda_{Mo}} - 1\right) \times (1 - e^{-\lambda_{Mo} \cdot t})} (Ci/\mu mol) \qquad \text{Equation 13}$$

As also shown in FIG. 16a, SA values are increased by a factor of >2 for elutions performed at <6 hours build-up time compared with that of a $^{99m}$Tc-solution obtained in a currently used single elution performed at the time of maximal $^{99m}$Tc build-up.

The concentration process described above also benefits other radionuclide generators. For example, the multifunctional sorbents of the present invention may be used in generator systems including $^{99m}$Tc/$^{99}$Mo, $^{188}$Re/$^{188}$W, $^{44}$Sc/$^{44}$Ti, $^{68}$Ga/$^{68}$Ge, $^{89m}$Y/$^{89}$Zr, $^{110m}$In/$^{110}$Sn, $^{113m}$In/$^{113}$Sn, and $^{172}$Lu/$^{172}$Hf.

A general method for the evaluating the effectiveness of an early elution regime is detailed below in the format of a mathematical equation for calculation of $R_y$, which is derived for the calculation of $R_y$ values for different radionuclide generator systems. In this formula, the daughter nuclide-yield ratio ($R_y$) is defined as a quotient of the total of daughter nuclide-elution yields eluted in all i 'early' elutions divided by the maximal daughter nuclide-activity or elution yield ($A_{d(Max)}$) which would be eluted from the generator at maximal build-up time $t_{Max}$ (Equation 14):

$$\left(\sum_{i=1}^{i=n} A_{d(E_i)} / A_{d(Max)}\right)\left(\sum_{i=1}^{i=n} A_{d(E_i)}\right) \qquad \text{Equation 14}$$

where $E_i$ is indexed for the i$^{th}$ elution. The build-up time ($t_b$) for each 'early' elution is $t_b=(t_{Max}/i)$, where i is the number (integer) of the 'early' elutions. Starting from the radioactivity equation ($A_d$) of daughter nuclide in the generator (Equation 15):

$$A_d = \lambda_d \times N_{0,p} \times b \times \left(\frac{\lambda_p}{\lambda_d - \lambda_p}\right) \times (e^{-\lambda_p \cdot t} - e^{-\lambda_d \cdot t}) \qquad \text{Equation 15}$$

and from the maximal build-up time $t_{Max}$ at which time the maximal daughter nuclide activity accumulated in radionuclide generator is available (Equation 16):

$$t_{max} = [\ln(\lambda_d/\lambda_p)]/(\lambda_d - \lambda_p) \qquad \text{Equation 16}$$

the equation for the evaluation of $R_y$ value is derived by inserting the relevant time values ($t_b$ and $t_{Max}$) into the $A_d$ equation (Equation 17):

$$R_y = \frac{\sum_{i=1}^{i=n} A_{d(E_i)}}{A_{d(Max)}} = \frac{\lambda_d \times N_{0,p} \times b \times \left(\frac{\lambda_p}{\lambda_d - \lambda_p}\right) \times \sum_{x=0}^{x=i-1}[e^{-\lambda_p \cdot x \cdot t_b} \times (e^{-\lambda_p \cdot t_b} - e^{-\lambda_d \cdot t_b})]}{\lambda_d \times N_{0,p} \times b \times \left(\frac{\lambda_p}{\lambda_d - \lambda_p}\right) \times (e^{-\lambda_p \cdot t_{Max}} - e^{-\lambda_d \cdot t_{Max}})}$$

$$R_y = \frac{\sum_{x=0}^{x=i-1}[e^{-\lambda_p \cdot x \cdot t_b} \times (e^{-\lambda_p \cdot t_b} - e^{-\lambda_d \cdot t_b})]}{(e^{-\lambda_p \cdot t_{Max}} - e^{-\lambda_d \cdot t_{Max}})}$$

Equation 17 where, A is the radioactivity; b is the daughter nuclide-branch decay factor; λ is the decay constant; the subscripts p and d describe the parent and daughter nuclide, respectively; x is the number of the elution performed before starting a daughter nuclide-build-up process for each consecutive elution. At this starting time point, it is assumed that there are no residual daughter nuclide atoms left in the generator from a preceding elution (i.e., a daughter nuclide-elution yield of 100% for the preceding elution is assumed). The theoretical calculation result (in comparison with experimental one) shown in FIG. 16b is an example of the use of above mentioned general $R_y$-equation in the evaluation of the effectiveness of an 'early' elution regime in the case of a $^{99m}$Tc/$^{99}$Mo generator system.

Example 7: Performance of Sorbent Materials in "Catch without Release" and "Catch and Release" Processes Table 15 shows the performance of the sorbents used in the radioisotope generators as a generator column and/or purification/concentration column and in the "catch-and-release"/"catch-without-release" processes.

Columns SG-1 and SG-2 were fully loaded with low specific radioactivity [$^{99}$MoO$_4$]$^-$ ions produced from $^{98}$Mo (n,γ)$^{99}$Mo reaction, and a molybdenum adsorption capacity of >315.0 mg Mo/g column was applied. The alumina (comparative example) column was loaded with high specific radioactivity [$^{99}$MoO$_4$]$^-$ ions produced from $^{235}$U fission, and a molybdenum adsorption capacity of <0.5 mg Mo/g column was applied.

TABLE 15

Performance of the sorbent materials used in radioisotope generators as a generator column and/or purification/concentration column.

| | | Chemical adsorption/desorption process with the sorbent "Catch without Release" Application of sorbents described in this invention | | | | | |
|---|---|---|---|---|---|---|---|
| | | For both generator column and purification column (Refer to FIG. 10) | | | For purification column (with purification column recovering process: Refer to FIG. 11) | | |
| | | Final solution nuclidic purity, % | | | Final solution nuclidic purity, % | | |
| Performance parameter | | WP | P | Fc | WP | P | Fc |
| SYS-1 | SG-1 | 98.54 | — | 1.0 | 98.47 | — | 1.0 |
| | SP-1 | — | >99.903 | 0.9 | — | >99.901 | 0.9 |
| SYS-2 | SG-2 | 99.53 | — | 1.0 | 99.45 | — | 1.0 |
| | SP-2 | — | >99.954 | 0.8 | — | >99.945 | 0.8 |

| | | Chemical adsorption/desorpt-ion process with the sorbent "Catch and Release" Application of sorbents described in this invention | | | | | |
|---|---|---|---|---|---|---|---|
| | | For both generator column and purification/concentration (PC) column (Refer to FIG. 12) | | | For purification/ concentration column (Refer to FIG. 13) | | |
| | | Final solution nuclidic purity, % | | | Final solution nuclidic purity, % | | |
| Performance parameter | | WPC | PC | Fc | WPC | PC | Fc |
| SYS-3 | SG-2 | 99.5 | — | 1.0 | 99.5 | — | 1.0 |
| | SPC-1 | — | >99.91 | >15 | — | >99.91 | >20 |
| SYS-4 | SG-2 | 99.5 | — | 1.0 | 99.5 | — | 1.0 |
| | SPC-2 | — | >99.96 | >15 | — | >99.96 | >20 |
| SYS-5 | SG-2 | 99.5 | — | 1.0 | 99.5 | — | 1.0 |
| | SPC-3 | — | >99.92 | >15 | — | >99.92 | >15 |
| SYS-6 | SG-2 | 99.5 | — | 1.0 | 99.5 | — | 1.0 |
| | SPC-4 | — | >99.96 | >15 | — | >99.96 | >15 |
| SYS-7 | Alumina* | — | — | — | 99.9 | — | 1.0 |
| | SPC-1 | — | — | — | — | >99.91 | >15 |
| SYS-8 | Alumina* | — | — | — | 99.9 | — | 1.0 |
| | SPC-2 | — | — | — | — | >99.96 | >15 |

TABLE 15-continued

Performance of the sorbent materials used in radioisotope generators as a generator column and/or purification/concentration column.

| SYS-9  | Alumina* | — | — | — | 99.9 | —       | 1.0 |
|--------|----------|---|---|---|------|---------|-----|
|        | SPC-3    | — | — | — | —    | >99.92  | >10 |
| SYS-10 | Alumina* | — | — | — | 99.9 | —       | 1.0 |
|        | SPC-4    | — | — | — | —    | >99.96  | >10 |

*Comparative example

Legend for Table 15:
SYS: Integrated generator system (Radioisotope generator column combined with purification/concentration column);
WP: Without purification column;
P: With purification column;
WPC: Without purification/concentration column;
PC: With purification/concentration column;
Fc: Eluate concentration factor (defined as the concentration of $^{99m}$Tc experimentally obtained in the final concentrated eluate divided by the $^{99m}$Tc concentration experimentally obtained in the eluate eluted from the generator column before passing through the purification/concentration column);
SG-1: Generator column SiTiO—Mo-99 (TiOH-functionalised silica sorbent loaded with $^{99}$Mo radionuclide);
SG-2: Generator column SiZrTiO—Mo-99 (ZrTiOH-functionalised silica sorbent loaded with $^{99}$Mo radionuclide);
SP-1: TiOH-functionalised silica sorbent purification column;
SP-2: ZrTiOH-functionalised silica sorbent purification column;
SPC-1: Purification/concentration column Si-DEAP (Diethylaminopropyl-functionalised silica sorbent);
SPC-2: Purification/concentration column Si-DEAPTi (Diethylaminopropyl/TiOH-functionalised silica sorbent);
SPC-3: Purification/concentration column Si-DEAM (Diethylaminomethyl-functionalised silica sorbent);
SPC-4: Purification/concentration column Si-DEAMTi (Diethylaminomethyl/TiOH-functionalised silica sorbent).

Discussion

As shown in Table 15, the sorbent materials of present invention are advantageous in both generator production and purification/concentration processes. In the 'catch without release' process, the sorbent materials of the present invention achieve purities of eluted $^{99m}$Tc of >98.45% when used in a radioisotope generator, and purities of eluted $^{99m}$Tc of >99.901% when used in a purification column. Further, the eluate concentration factors (Fc) of $^{99m}$Tc in the eluate after purification with sorbent materials according to the present invention are at least >0.8. In the 'catch and release' process, the sorbent materials of the present invention achieve purities of eluted $^{99m}$Tc of 99.5% when used in a radioisotope generator, and purities of eluted $^{99m}$Tc of >99.91% when used in purification/concentration columns. Further, the eluate concentration factors (Fc) of Tc in the eluate after purification/concentration with sorbent materials according to the present invention are at least >10.

Figure 19:
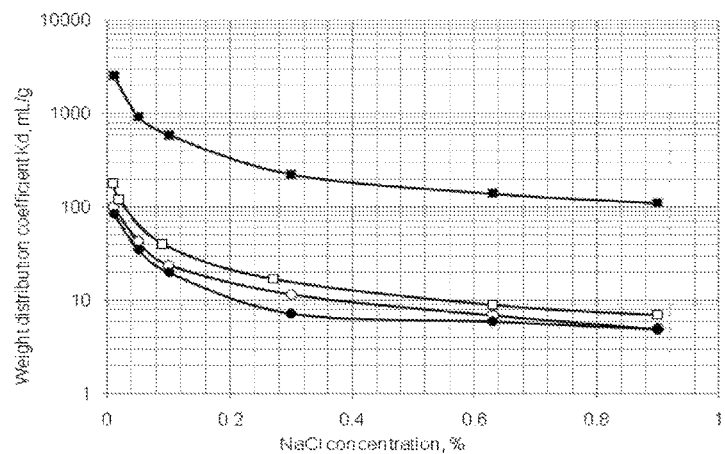
FIG. 19 shows the distribution coefficient ($K_d$) values of [$^{99m}$TcO$_4$]$^-$ ions in NaCl solutions of acidity pH=8.5 for multifunctional sorbents used in radioisotope purification/concentration processes. Key: Sorbent A: Tertiary aminoalkyl (3-diethyl aminoalkyl)-functionalised silica according to the present invention (open circle); Sorbent B: Mixed tertiary aminoalkyl (3-diethyl aminoalkyl)/TiOH-functionalised silica according to the present invention (open square); Comparative Sorbent C: Quaternary aminoalkyl-functionalised silica Accell QMA SePak® not according to the present invention (solid circle); Comparative Sorbent D: Tertiary aminoalkyl-functionalised cellulose DEAE (diethyl aminoethyl)-cellulose not according to the present invention (solid square).

Example 8: Elation Performance of Sorbent Materials in Concentration ('Catch and Release') Processes FIG. 19 shows that Sorbents A and B of the present invention and Comparative Sorbents C and D, which are all functionalised with aminoalkyl groups, have large Kd values (i.e., high adsorption capability) for $[^{99m}TcO_4]^-$ ions in NaCl solutions when the NaCl concentration is low (<0.01% NaCl), and have smaller Kd values (or lower adsorption capability) at higher concentrations (from 0.01% to >0.9% NaCl). This demonstrates that $^{99m}$Tc-concentration processes can be performed by first catching/adsorbing $^{99m}$Tc onto these sorbents from a larger volume of $^{99m}$Tc solution in water (or in a dilute NaCl solution, e.g., <0.01% NaCl, as shown in FIG. 20(a)) and then releasing $^{99m}$Tc from the sorbent with a much smaller volume of physiological (e.g., 0.9%) NaCl solution to receive a $^{99m}$Tc solution of relatively higher $^{99m}$Tc radioactivity concentration (as shown in FIG. 20(b)).

Figure 20:
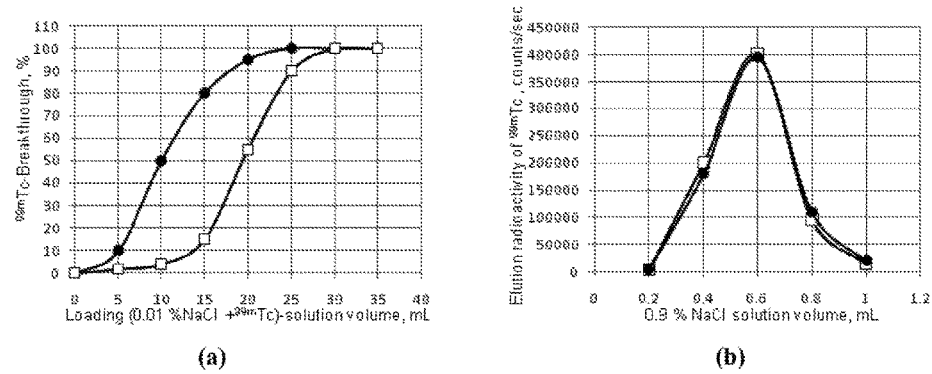
FIG. 20 shows (a) a graph of loading $^{99m}$Tc from a 0.01% NaCl+Na[$^{99m}$TcO$_4$] solution of acidity pH=6 (which is simulated based on a $^{99m}$Tc eluate from a $^{99m}$Tc generator after passing through an ion-exchange resin column (DOWEX® AG-50W-X8 in silver form) to remove Cl$^-$ ions from the 0.9% NaCl solution used in the generator elution) onto a purification/concentration column packed with 100 mg Sorbent B (mixed tertiary aminoalkyl (3-diethyl aminoalkyl)/TiOH-functionalised silica synthesised in this invention) [open square] compared to a purification/concentration column packed with 100 mg Comparative Sorbent C (quaternary aminoalkyl-functionalized silica Accell QMA SePak®) [solid circle]; (b) a graph of eluting $^{99m}$Tc with 0.9% NaCl solution (pH=5) from a purification/concentration column packed with 100 mg Sorbent B [open square] compared to a purification/concentration column packed with 100 mg Comparative Sorbent C [solid circle]; (c) a graph of the $^{99m}$Tc-activity build-up and elution profile for a purification/concentration process based on the "catch-and-release" concept used in a radioisotope concentrator ULTRALUTE® process (for example, as described above for FIG. 13) using a purification/concentration column (K3 in FIG. 13) packed with 100 mg Sorbent B synthesised according to this invention. Chloride removing column (K2 in FIG. 13) is composed of the cation exchange resin DOWEX® AG-50W-X8 in silver form.
Figure 20:
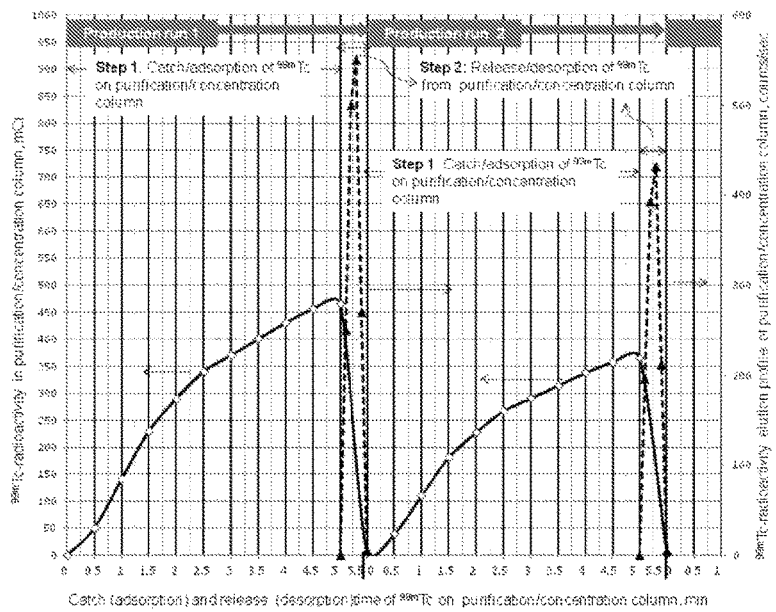

FIG. 19 also shows that, compared to a Comparative Sorbent C, Sorbents A and B of the present invention have a larger Kd values for $[^{99m}TcO_4]^-$ ions in NaCl solutions of low concentration (<0.01% NaCl) and approximately equal Kd values to Comparative Sorbent C at the useful physiological concentration value (0.9% NaCl). This fact makes Sorbent A and B better suited to absorbing $^{99m}$Tc from a larger volume of $^{99m}$Tc solution in water or in dilute NaCl solution (<0.01% NaCl) compared with Sorbent C (see FIG. 20(a)), but still allows release of $^{99m}$Tc from Sorbents A, B and C with an approximately equal volume of physiological 0.9% NaCl solution (see FIG. 20(b)). As shown in FIG. 20(a), for an equal breakthrough of 10%, about 13 mL $^{99m}$Tc-solution can be loaded onto a column comprising 100 mg Sorbent B but only 5 mL $^{99m}$Tc-solution can be loaded onto a column of 100 mg Comparative Sorbent C. Subsequently eluting the $^{99m}$Tc from both the sorbent columns with 1.0 mL 0.9% NaCl solution (FIG. 20(b)) gives a concentration factor (Fc) of 13 for Sorbent B (present invention) compared to Fc=5 for Sorbent C (non-inventive sorbent). Hence, it is evident from FIG. 20 and Table 15 that Sorbents A and B according to the present invention result in higher concentration factors, and hence outperform Comparative Sorbent C, in concentration processes.

Further, although the adsorption of $^{99m}$Tc on Comparative Sorbent D is very high with a Kd value>1000 mL/g in low NaCl concentration (<0.01% NaCl) solution (see FIG. 19), desorption of $^{99m}$Tc from this sorbent is more difficult because of the high adsorption capability of Tc (Kd>100 mL/g) in physiological (0.9%) NaCl solution. This may reduce the concentration factor of solutions eluted through this material, and/or result in a final $^{99m}$Tc-solution having a large volume, which is not an optimal choice for end users.

In relation to the concentration process detailed in this Example, where all the steps are performed with different NaCl solutions of approximately unchanged pH values, the 'catch-and-release' concept applied in this example is also demonstrated by the comparative ion exchange property of the sorbents. The ion exchange capacity value of Sorbents A and B (present invention) of >1.3 meq/g demonstrates the superior adsorption property of these sorbent materials compared to the ion exchange capacity of Comparative Sorbent C of 0.23 meq/g.

A further superior property of inventive Sorbents A and B is their pH-controlled adsorption/desorption ('catch and release' controlled by changing the pH of the solutions). The ionisation of tertiary aminoalkyl functional groups on Sorbents A and B (e.g., Si(OH)(R)(NR'$_2$)) with their ionisation constant values pKa≈11.2 are strongly affected by the pH variation of the solution during concentration/purification. The tertiary aminoalkyl functional groups of Sorbents A and B are partly ionised in the pH range pH>11.2 and fully ionised at pH<11.2. This ionisation property enhances the solute selectivity of these sorbents in the separation media/solutions of variable pH values. By contrast, as Comparative Sorbent C is functionalised with quaternary aminoalkyl groups (Si(R')(NR$_3$)$^+$), this sorbent lacks the pH-controllable property due to being fully ionised across almost the full pH range of the solution. As a result, Comparative Sorbent C may lose solute selectivity in the separation media/solutions of variable pH values.

Figure 21:
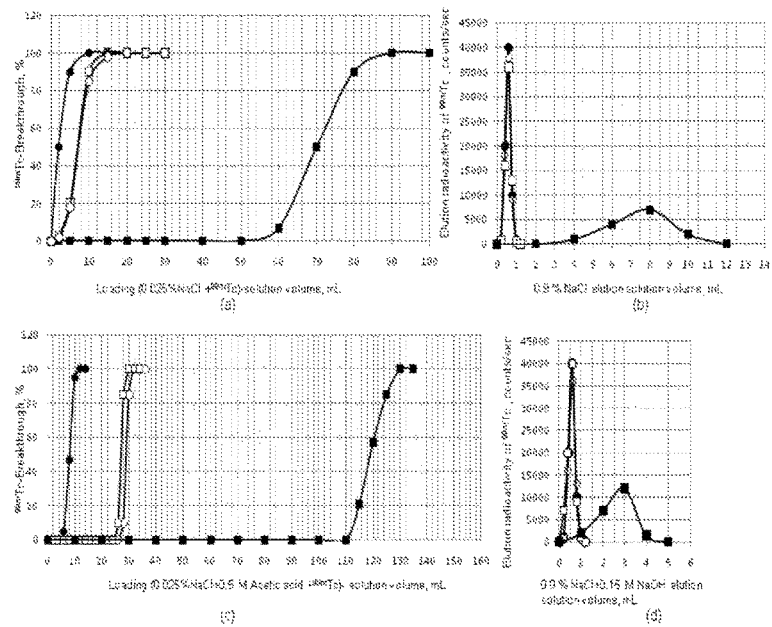
FIG. 21 shows (a) a graph of loading $^{99m}$Tc from a 0.025% NaCl+Na[$^{99m}$TcO$_4$] solution of acidity pH=6 onto a purification/concentration column packed with 100 mg each of: Sorbent A: Tertiary aminoalkyl (3-diethyl aminoalkyl)-functionalised silica according to the present invention (open circle); Sorbent B: Mixed tertiary aminoalkyl (3-diethyl aminoalkyl)/TiOH-functionalised silica according to the present invention (open square)] compared to Comparative Sorbent C: Quaternary aminoalkyl-functionalized silica Accell QMA SePak® (solid circle) and/or Comparative Sorbent D: Tertiary aminoalkyl-functionalized cellulose DEAE (diethyl aminoethyl)-cellulose (solid square); (b) a graph of eluting $^{99m}$Tc with 0.9% NaCl solution (pH=5) from a purification/concentration column packed with 100 mg of Sorbent A (open circle) and/or Sorbent B (open square) compared to Comparative Sorbent C (solid circle) and/or Comparative Sorbent D (solid square); (c) a graph of loading $^{99m}$Tc from a 0.025% NaCl+0.5 M acetic acid+Na[$^{99m}$TcO$_4$] solution of acidity pH=2.35-2.46 onto a purification/concentration columns packed with 100 mg of Sorbent A (open circle) and/or Sorbent B (open square) compared to Comparative Sorbent C (solid circle) and/or Comparative Sorbent D (solid square)]; (d) a graph of eluting $^{99m}$Tc with 0.9% NaCl+0.15M NaOH solution (pH=13) from the purification/concentration column packed with 100 mg of Sorbent A (open circle) and/or Sorbent B (open square)] compared to Comparative Sorbent C (solid circle) and/or Comparative Sorbent D (solid square)].

As shown in FIG. 21(c), the loadings of $^{99m}$Tc onto the Sorbents A and B and Comparative Sorbent D in a more acidic solution (0.025% NaCl+0.5 M Acetic acid, pH=2.35) are much higher than the case of loading performed in a less acidic solution (0.025% NaCl, pH=6) as shown in FIG. 21(a). The loading of $^{99m}$Tc onto Comparative Sorbent C does not change substantially in different pH conditions.

Releasing/eluting $^{99m}$Tc from Sorbents A and B and Comparative Sorbent D with a more basic solution (0.9% NaCl+0.15 M NaOH, pH≈13) is much easier (i.e., requires a much smaller solution volume; see FIG. 21(d)) than eluting $^{99m}$Tc in a less basic solution (0.9% NaCl, pH≈6; see FIG. 21(b)). Eluting $^{99m}$Tc from Comparative Sorbent C requires larger volumes than Sorbents A, B, and D under different pH conditions.

Although the loading of $^{99m}$Tc on Comparative Sorbent D is high in all pH solutions (FIGS. 21(a) and (c)), the desorption of $^{99m}$Tc from this sorbent is more difficult because of the high adsorption of $^{99m}$Tc in physiological (0.9%) NaCl solution (see FIG. 21(b)) and even in basic 0.9% NaCl solution (see FIG. 21(d)). This fact may reduce the concentration factor and/or result in the final $^{99m}$Tc-solution having a large volume. Without being bound by theory, this drawback of Sorbent D may result from a specific interaction between [TcO$_4$]$^-$ ions and the cellulose matrix, and demonstrates the comparatively advantageous properties of the multifunctional sorbent materials of this invention.

In summary, a concentrated $^{99m}$Tc-solution may be obtained using inventive Sorbents A and B by first catching/adsorbing $^{99m}$Tc onto Sorbents A and B from a larger volume of acidic $^{99m}$Tc-solution (0.025% NaCl+0.5 M Acetic acid, pH=2.35) as shown in FIG. 21(c) and then releasing $^{99m}$Tc from the sorbents with a much smaller volume of physiological 0.9% NaCl solution (pH=6-8) to receive a $^{99m}$Tc solution of high $^{99m}$Tc radioactivity concentration.

Without being bound by theory, the pH control of adsorption on/desorption from inventive Sorbents A and B may be explained by the following example equations:

1. Catching/adsorption process for $^{99m}$Tc loading on Sorbent A or Sorbent B in acetic acid solution:

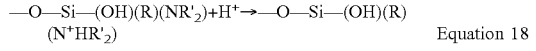

Equation 18

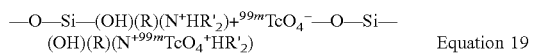

Equation 19

2. Releasing process for $^{99m}$Tc elution from Sorbent A or Sorbent B with a basic solution:

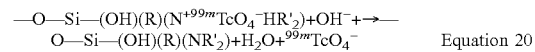

Equation 20

The invention claimed is:

1. A method for producing a sorbent material comprising particulate porous silica having a plurality of oligomeric chains on a surface thereof, said oligomeric chains having a backbone consisting of alternating oxygen and M atoms, wherein each M is independently selected from the group consisting of tetravalent Si, Zr, Ti, Hf, Sn, Th, Pb, and Ge, and wherein each of said chains comprises a plurality of M-OH moieties, said method, comprising:
   a) providing a particulate porous silica substrate, said substrate comprising a plurality of silanol groups on a surface thereof,
   b) reacting said silanol groups with
      i) a silicon compound of formula R$_n$Si(OR')$_{4-n}$, where R is an alkyl group and n is 0 or 1; or
      ii) an aminoalkyl silane of formula R"$_m$R$_n$Si(OR')$_{4-n-m}$ having at least two hydrolysable groups attached to silicon, where R" is an aminoalkyl group, m is 1 or 2 and n is 0 or 1; or,
      iii) a compound of formula M(OR')$_4$; or
      iv) a mixture of any two or more of i) to iii);
   c) hydrolysing the product of b) to generate hydroxyl groups;
   d) reacting the hydroxyl groups generated in step c) with one or more reagents, wherein each reagent is independently selected from the group consisting of an aminoalkyl silane having at least two hydrolysable groups attached to the silicon and a compound of formula M(OR')$_4$; and
   e) hydrolysing the product of d);
wherein each OR' is a hydrolysable group wherein each R' may be the same or may be different, and each M is, independently, Zr, Ti, Hf, Sn, Th, Pb or Ge.

2. The method of claim 1, wherein steps d) and e) are repeated between 1 and 10 times.

3. The method of claim 1, wherein the porous silica substrate used in step a) has a surface area per silanol group of between about 20 and about 150 Å$^2$/OH.

4. The method of claim 1, wherein the porous silica substrate of step a) has a specific surface area of between about 300 and about 1000 m$^2$/g.

5. The method of claim 1, wherein the hydrolysing in step c) comprises reacting the hydrolysable groups formed in step b) with an approximately stoichiometric amount of water.

6. The method of claim 1, wherein the hydrolysing in step e) comprises reacting the hydrolysable groups formed in step d) with an approximately stoichiometric amount of water.

7. The method of claim 1, wherein the silicon compound of step b) i) is a tetraalkoxysilane.

8. The method of claim 1, wherein step a) comprises
   A) providing a suspension of a nanoparticulate substance in an aqueous solution of a silicate salt;
   B) acidifying said aqueous solution so as to form a gel;
   C) heating said gel to form a monolith;
   D) forming a particulate material from said monolith; and,
   E) treating said particulate material with an extracting solution so as to extract the nanoparticulate substance from the particulate material.

9. A sorbent material comprising particulate porous silica having a plurality of oligomeric chains on a surface thereof, said oligomeric chains having a backbone consisting of alternating oxygen and M atoms, where each M is independently selected from the group consisting of tetravalent Si, Zr, Ti, Hf, Sn, Th, Pb, and Ge, and wherein each of said chains comprises a plurality of M-OH moieties.

10. The sorbent material of claim 9, wherein the oligomeric chains have backbones having a maximum length of 18 MO units.

11. The sorbent material of claim 9, wherein at least one M per oligomeric chain is not Si.

12. The sorbent material of claim 9, wherein each oligomeric chain comprises at least one aminoalkyl group bonded to an Si atom.

13. The sorbent material of claim 9, wherein the sorbent material has a specific surface area of between about 300 and about 1000 m$^2$/g.

14. A method for purifying and/or concentrating a solution comprising a mixture of metal ions, said method comprising:
   a) providing a solution comprising one or more contaminant species and one or more target species;
   b) contacting the solution of step a) with a sorbent material comprising particulate porous silica having a plurality of oligomeric chains on a surface thereof, said oligomeric chains having a backbone consisting of alternating oxygen and tetravalent M atoms, wherein each of said chains comprises a plurality of M-OH moieties,
and wherein each M is independently selected from the group consisting of Si, Zr, Ti, Hf, Sn, Th, Pb, and Ge; and,
   c) separating the solution from the sorbent material as an eluate following step b).

15. The method of claim 14, additionally comprising d) extracting the sorbent material from step c) with an extracting solution so as to produce an extract, said extracting solution being capable of extracting the target species from the sorbent material.

16. The method of claim 14, additionally comprising step d) recycling the solution of step c) through additional column of sorbent material used prior to step a).

17. The method of claim 14, wherein the contaminant species is of formula $[Z^1O_4]^{2-}$ and the target species is of formula $[Z^2O_4]^-$, wherein $Z^1$=Mo or W and $Z^2$=Tc or Re.

18. The method of claim 14, wherein the contaminant species is a $D^{4+}$ ion, wherein D is selected from the group consisting of Ti, Ge, Zr, Sn and Hf and the target species is an $X^{3+}$ ion, wherein X is selected from the group consisting of Sc, Ga, Y, In or Lu.

19. The method of claim 14, wherein the oligomeric chains of the sorbent material comprise at least one M that is not Si.

20. The method of claim 14, wherein the sorbent material of step b) comprises at least one aminoalkyl group bonded to an M centre, and wherein each M is Si.

21. The method of claim 14, wherein the oligomeric chains of the sorbent material further comprise at least one aminoalkyl group bonded to an Si atom.

22. The method of claim 14, wherein the method further comprises step d) regenerating the sorbent material; wherein said regenerating comprises adding a regenerating solution to the sorbent material.

23. The method of claim 22, wherein the regenerating solution comprises a solution of sodium hydroxide, potassium hydroxide, or ammonium hydroxide, or a mixture of any two or more of these.

24. The method of claim 14, wherein the method additionally comprises the following steps A) to C) prior to step a);
   A) providing a solution comprising one or more target species and one or more contaminant species;
   B) contacting the solution of step A) with a sorbent material comprising porous silica having a plurality of oligomeric chains on a surface thereof, said oligomeric chains having a backbone consisting of alternating oxygen and tetravalent M atoms, and wherein each of said chains comprises a plurality of M-OH moieties;
wherein the oligomeric chains of the sorbent material comprise at least one M that is not Si; and, wherein the affinity of the sorbent material for the target species is lower than that for the contaminant species; and
   C) extracting the sorbent material from step B) with an extracting solution so as to produce an extract, said extracting solution being capable of extracting the target species from the sorbent material and said extract being the solution of step a).

25. The method of step 24, additionally comprising step D), after step C) and before step a), step D) being recycling the extract of step C) through the sorbent material.

26. The method of claim 24, wherein the solution of step A) comprises a parent species that decays over time to form the target species, whereby the parent species is the contaminant species.

27. The method of claim 25, wherein the parent species is of formula $[Z^1O_4]^{2-}$ and the target species is of formula $[Z^2O_4]^-$, wherein when $Z^1$=Mo, $Z^2$=Tc, or when $Z^1$=W, $Z^2$=Re or wherein the contaminant species is a $D^{4+}$ ion, wherein D is selected from the group consisting of Ti, Ge, Zr, Sn and Hf and the target species is an $X^{3+}$ ion, wherein X is selected from the group consisting of Sc, Ga, Y, In or Lu.

* * * * *